United States Patent
Harewood et al.

(10) Patent No.: US 11,969,343 B2
(45) Date of Patent: Apr. 30, 2024

(54) TRANSCATHETER HEART VALVE PROSTHESIS SYSTEMS AND METHODS FOR ROTATIONAL ALIGNMENT

(71) Applicant: Medtronic, Inc., Minneapolis, MN (US)

(72) Inventors: Frank Harewood, Galway (IE); Taylor Winters, Santa Ana, CA (US); Evelyn Birmingham, Ballybrit (IE); Sara Saul, Minneapolis, MN (US); Victor Kimball, Minneapolis, MN (US); Eric Pierce, Mission Viejo, CA (US); Radhika Bhargav, Mountain View, CA (US); Jeffrey Sandstrom, Scandia, MN (US); Caitlin Dorff, Santa Rosa, CA (US)

(73) Assignee: Medtronic, Inc., Minneapolis, MN (US)

(*) Notice: Subject to any disclaimer, the term of this patent is extended or adjusted under 35 U.S.C. 154(b) by 71 days.

(21) Appl. No.: 17/543,611

(22) Filed: Dec. 6, 2021

(65) Prior Publication Data
US 2022/0175524 A1 Jun. 9, 2022

Related U.S. Application Data

(60) Provisional application No. 63/193,779, filed on May 27, 2021, provisional application No. 63/132,927, (Continued)

(51) Int. Cl.
*A61F 2/24* (2006.01)
*A61B 34/20* (2016.01)

(52) U.S. Cl.
CPC ............ *A61F 2/2427* (2013.01); *A61B 34/20* (2016.02); *A61F 2/2418* (2013.01); (Continued)

(58) Field of Classification Search
CPC .................. A61F 2/2427; A61F 2/2418; A61F 220/0075; A61F 2250/0098; A61B 34/20; A61B 2034/2065
See application file for complete search history.

(56) References Cited

U.S. PATENT DOCUMENTS

| | | | |
|---|---|---|---|
| 6,361,557 | B1 | 3/2002 | Gittings et al. |
| 6,574,497 | B1 | 6/2003 | Pacetti |

(Continued)

FOREIGN PATENT DOCUMENTS

| | | |
|---|---|---|
| CN | 104644288 A | 5/2015 |
| CN | 108882980 A | 11/2018 |

(Continued)

OTHER PUBLICATIONS

Gada, Hemal. "TAVI Implantation Optimisation—Practical Aspects of Cusp Overlap Technique—PCR e-Course 2020." YouTube, Jun. 29, 2020, www.youtube.com/watch?v=wqc1-7dQ9Wg. (Year: 2020).*

(Continued)

*Primary Examiner* — Suba Ganesan
(74) *Attorney, Agent, or Firm* — Medler Ferro Woodhouse Mills PLLC

(57) ABSTRACT

Methods for rotationally aligning transcatheter heart valve prosthesis within a native heart valve include percutaneously delivering the transcatheter heart valve prosthesis to the native heart valve, wherein the transcatheter heart valve prosthesis includes at least one imaging marker, receiving a cusp overlap viewing angle image and/or a coronary overlap viewing angle image of the transcatheter heart valve prosthesis within the native heart valve, determining, based on the cusp overlap viewing angle image and/or the coronary overlap viewing angle image and the at least one imaging marker, whether the transcatheter heart valve prosthesis is in a desired rotational orientation, if the at least one imaging marker in the cusp overlap viewing angle image and/or the (Continued)

coronary overlap viewing angle indicates that the transcatheter heart valve prosthesis is not in the desired rotational orientation, rotating the transcatheter heart valve prosthesis until the transcatheter heart valve prosthesis is in the desired rotational orientation.

17 Claims, 51 Drawing Sheets

Related U.S. Application Data filed on Dec. 31, 2020, provisional application No. 63/122,404, filed on Dec. 7, 2020.

(52) U.S. Cl.
CPC ............ *A61B 2034/2065* (2016.02); *A61F 2220/0075* (2013.01); *A61F 2250/0098* (2013.01)

(56) References Cited

U.S. PATENT DOCUMENTS

| | | | |
|---|---|---|---|
| 6,935,404 | B2 | 8/2005 | Duerig et al. |
| 7,972,378 | B2 | 7/2011 | Tabor et al. |
| 8,673,000 | B2 | 3/2014 | Tabor et al. |
| 8,998,981 | B2 | 4/2015 | Tuval et al. |
| 9,744,034 | B2 | 8/2017 | Braido et al. |
| 9,839,513 | B2 | 12/2017 | Essinger et al. |
| 2003/0114913 | A1 | 6/2003 | Spenser et al. |
| 2006/0235505 | A1 | 10/2006 | Oepen |
| 2008/0147118 | A1 | 6/2008 | Ghione et al. |
| 2008/0275540 | A1 | 11/2008 | Wen |
| 2009/0076594 | A1 | 3/2009 | Sabaria |
| 2009/0192591 | A1 | 7/2009 | Ryan et al. |
| 2010/0198346 | A1 | 8/2010 | Keogh et al. |
| 2010/0249908 | A1 | 9/2010 | Chau et al. |
| 2011/0022157 | A1 | 1/2011 | Essinger |
| 2013/0058556 | A1 | 3/2013 | Ohishi et al. |
| 2013/0325107 | A1 | 12/2013 | Wu |
| 2014/0188219 | A1 | 7/2014 | Conklin et al. |
| 2014/0277389 | A1 | 9/2014 | Braido et al. |
| 2015/0230923 | A1 | 8/2015 | Levi |
| 2016/0296324 | A1 | 10/2016 | Bapat et al. |
| 2018/0221181 | A1 | 8/2018 | Fischer et al. |
| 2018/0289471 | A1 | 10/2018 | Schreck et al. |
| 2018/0344458 | A1 | 12/2018 | Spenser et al. |
| 2019/0117424 | A1 | 4/2019 | Berra |
| 2019/0192275 | A1 | 6/2019 | Kim et al. |
| 2019/0247177 | A1 | 8/2019 | Kim |
| 2019/0262507 | A1 | 8/2019 | Adamek-Bowers et al. |
| 2019/0307589 | A1 | 10/2019 | Goldberg et al. |
| 2019/0365957 | A1 | 12/2019 | Paquin |
| 2020/0268535 | A1 | 8/2020 | Carpenter et al. |
| 2020/0390575 | A1 | 12/2020 | Guo et al. |
| 2023/0190466 | A1* | 6/2023 | Bialas .................. A61F 2/24 623/2.11 |

FOREIGN PATENT DOCUMENTS

| | | |
|---|---|---|
| CN | 109906099 A | 6/2019 |
| EP | 2301617 A1 | 9/2010 |
| EP | 2055266 B1 | 2/2012 |
| EP | 3205308 A1 | 8/2017 |
| JP | 2012081136 A | 4/2012 |
| WO | 2010031060 A1 | 3/2010 |
| WO | 2011137531 A1 | 11/2011 |
| WO | 2014171183 A1 | 10/2014 |
| WO | 2016100806 A1 | 6/2016 |
| WO | 2017103830 A1 | 6/2017 |
| WO | 2017167857 A1 | 10/2017 |
| WO | 2021040547 A1 | 3/2021 |
| WO | 2021/178543 A1 | 9/2021 |
| WO | 2021/178550 A1 | 9/2021 |

OTHER PUBLICATIONS

Tang et al., Alignment of Transcatheter Aortic-Valve Neo-Commissures (ALIGN TAVR). J Am Coll Cardiol Intv. May 2020, 13 (9) 1030-1042 (Year: 2020).*

Redondo et al., "Accurate commissural alignment during Acurate neo TAVI procedure", Rev Esp Cardiol, available online Mar. 26, 2021.

De Backer et al., "Redo-TAVR, What About the Coronary Arteries?", JACC: Cardiovascular Interventions, vol. 13, No. 22, pp. 2628-2630, Nov. 23, 2020.

Ochiai et al., "Risk of Coronary Obstruction Due to Sinus Sequestration in Redo Transcatheter Aortic Valve Replacement", JACC: Cardiovascular Interventions, col. 13, No. 22, pp. 2617-2627, Nov. 23, 2020.

Takamatsu et al., "Lateral Approach for Modifying Hat-Marker Orientation to Minimize Neo-Commissual Overlap During Transcatheter Aortic Valve Replacement", JACC: Cardiovascular Interventions, vol. 13, No. 22, pp. e199-e201, Nov. 23, 2020.

Tang et al. "Alignment of Transcatheter Aortic-Valve Neo-Commissures (ALIGN TAVR)", JACC: Cardiovascular Interventions, vol. 13, No. 9, pp. 1031-1042, May 11, 2020.

Tang et al., "Commissural Alignment in Evolut TAVR: Results from the Low Risk CT Sub-Study", PCR London Valves, e-poster, Nov. 2020.

Tang et al., "Feasibility of repeat TAVR After SAPIEN 3 TAVR: a novel classification scheme and pilot angiographic study", JACC Cardiovasc Interventions, vol. 12, No. 13, pp. 1290-1292, Jul. 8, 2019.

Tagliari et al., "Tanscatheter Aortic Valve Neo-Commissure Alignment with the Portico System" EuroIntervention 2020, 13 pages, Dec. 22, 2020.

Redondo et al. "How to Perform Accurate Commissural Alignment with All TAVR Devices Webinar", Wondr Medical video, https://wondrmedical.net/ch/vall-academy/videos/How-To-Perform-Accurate-Commissural-Align-DCC8A9FD5, Feb. 11, 2021.

International Search Report and Written Opinion, International Application No. PCT/US2021/062141, dated Apr. 14, 2022.

* cited by examiner

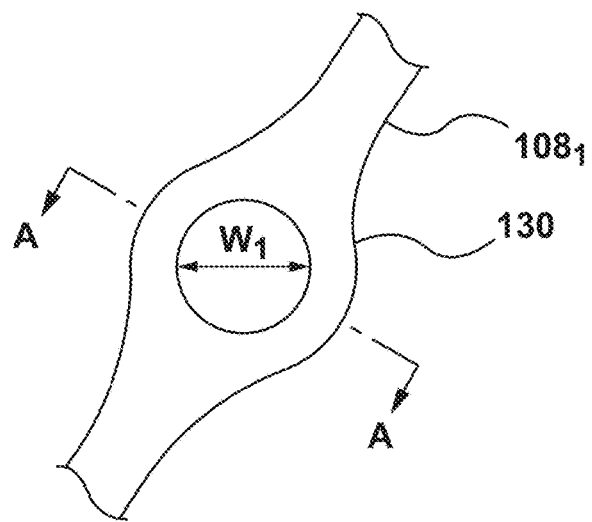
FIG. 1E
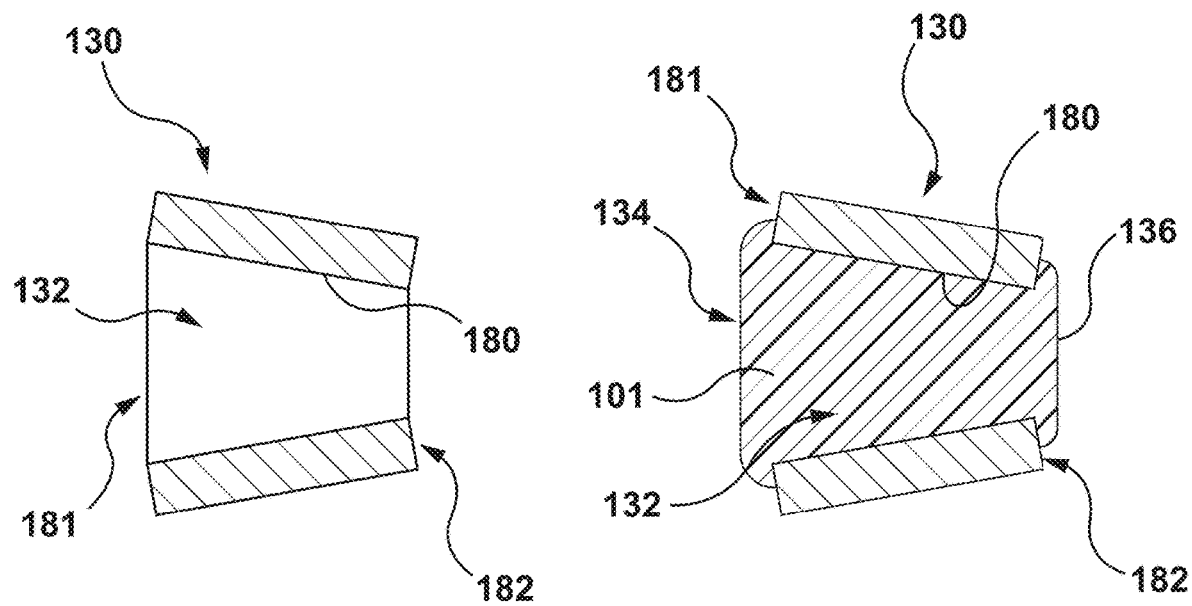
FIG. 1F
FIG. 1G

The corridor of confidence

Cusp overlap view
(NCC isolated)

Simplified representation of the ideal.

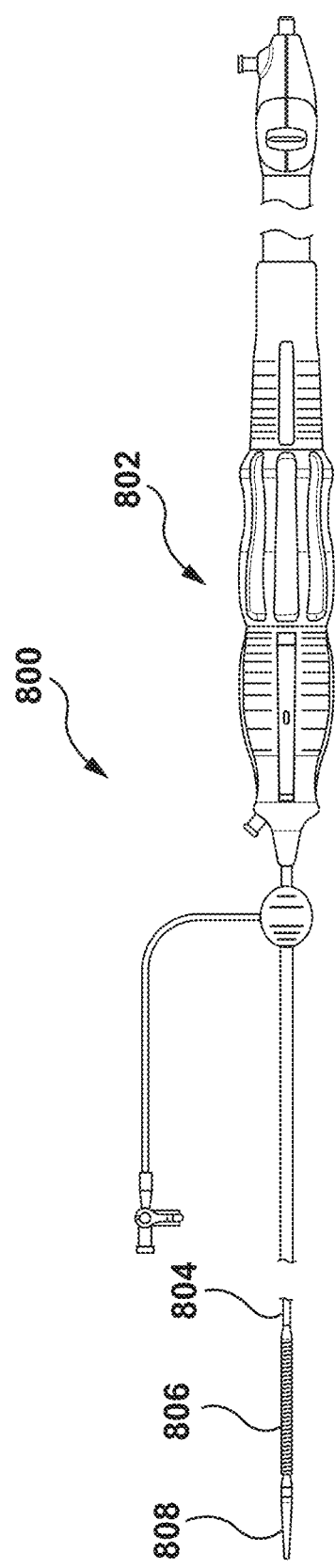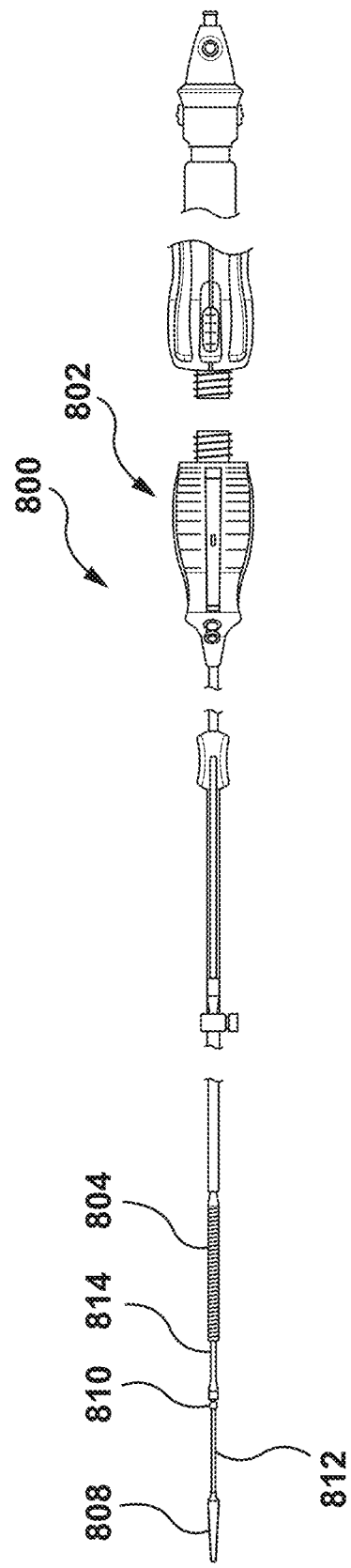
FIG. 13
FIG. 14

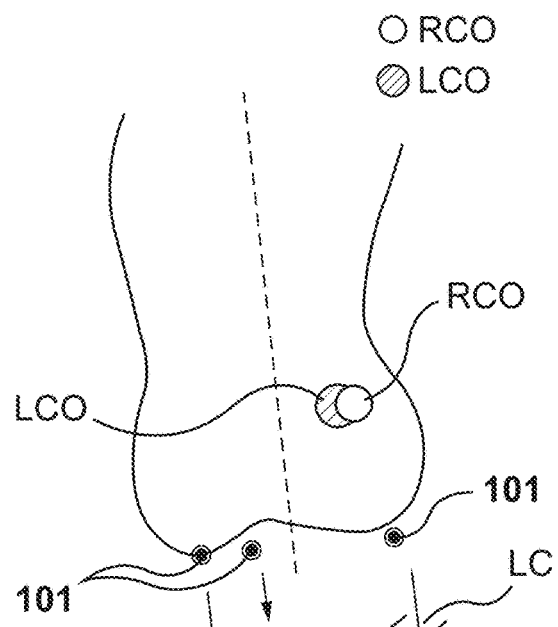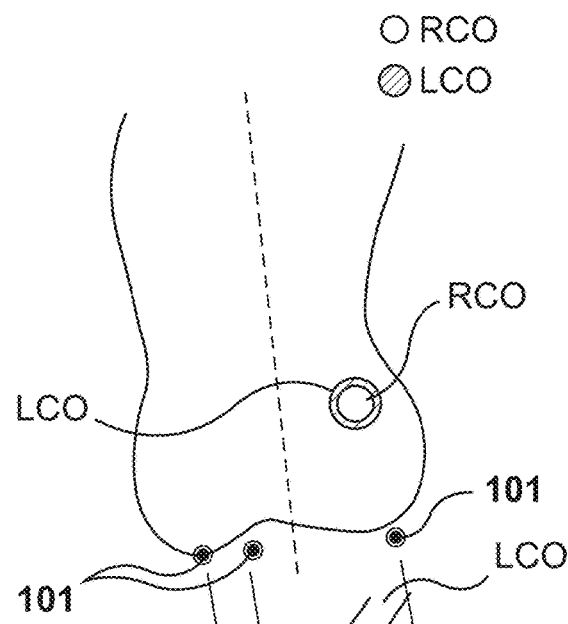
Cusp overlap
Coronary overlap
FIG. 16C
FIG. 16D

TRANSCATHETER HEART VALVE PROSTHESIS SYSTEMS AND METHODS FOR ROTATIONAL ALIGNMENT

CROSS-REFERENCE TO RELATED APPLICATIONS

This application claims the benefit under 35 U.S.C. § 119(e) of the filing date of: U.S. Provisional Application No. 63/122,404, filed Dec. 7, 2020; U.S. Provisional Application No. 63/132,927, filed Dec. 31, 2020; and U.S. Provisional Application No. 63/193,779, filed May 27, 2021, the contents of each of which are incorporated by reference herein in their entirety.

FIELD

The present technology is generally related to medical devices. More particularly, the present technology is related to frames or stents for transcatheter heart valve prostheses that include imaging markers, and systems and methods for rotationally aligning such transcatheter heart valve prostheses.

BACKGROUND

Patients suffering from various medical conditions or diseases may require surgery to install an implantable medical device. For example, valve regurgitation or stenotic calcification of leaflets of a heart valve may be treated with a heart valve replacement procedure. A traditional surgical valve replacement procedure requires a sternotomy and a cardiopulmonary bypass, which creates significant patient trauma and discomfort. Traditional surgical valve procedures may also require extensive recuperation times and may result in life-threatening complications.

One alternative to a traditional surgical valve replacement procedure is delivering implantable medical devices using minimally-invasive techniques. For example, a transcatheter heart valve prosthesis can be percutaneously and transluminally delivered to an implant location. In such methods, the transcatheter heart valve prosthesis can be compressed or crimped on a delivery catheter for insertion within a patient's vasculature; advanced to the implant location; and re-expanded to be deployed at the implant location. In many cases, such as those involving cardiovascular vessels, the route to the treatment/deployment site may be tortuous and may present conflicting design considerations requiring compromises between dimensions, flexibilities, material selection, operational controls and the like. Typically, advancement of a delivery catheter within a patient is monitored fluoroscopically to enable a clinician to manipulate the catheter to steer and guide its distal end through the patient's vasculature to the target treatment/deployment site. This tracking requires a distal end of the delivery catheter to be able to navigate safely to the target treatment/deployment site through manipulation of a proximal end by the clinician.

A need in the art still generally exists for improved devices and methods for monitoring and tracking the positioning and deployment of the implantable medical device during navigation through or within a patient's anatomy and positioning at the implant site.

SUMMARY

The techniques of this disclosure generally relate to frames or stents for implantable medical devices that include markers.

In one aspect, the present disclosure is directed to a stent for supporting a valve structure. The stent includes a plurality of struts forming cells, and a containment member configured to house an imaging marker. The containment member is positioned on a first strut of the plurality of struts positioned adjacent an inflow end of the stent. The containment member is substantially axially aligned with a first commissure of valve leaflets of the valve structure supported by the stent.

In another aspect, and in combination with any of the other aspects, the containment member comprises a first containment member, and the stent further includes a second containment member and a third containment member.

In another aspect, and in combination with any of the other aspects, the first containment member, the second containment member, and third containment member are circumferentially aligned such that the first, second, and third containment members are located an equal longitudinal distance from the inflow end of the stent.

In another aspect, and in combination with any of the other aspects, the first containment member, the second containment member, and the third containment member are circumferentially offset by approximately 120 degrees around the circumference of the stent.

In another aspect, and in combination with any of the other aspects, the second containment member is substantially axially aligned with a second commissure of valve leaflets of the valve structure supported by the stent and the third containment member is substantially axially aligned with a third commissure of valve leaflets of the valve structure supported by the stent.

In another aspect, and in combination with any of the other aspects, the containment member comprises an exterior surface, an interior surface, and a sidewall forming a circular shaped cavity.

In another aspect, and in combination with any of the other aspects, the stent further includes a first radiopaque marker press fit into the cavity to fill the cavity and form a first cap on the exterior surface of the containment member and a second cap on the interior surface of the one containment member.

In another aspect, and in combination with any of the other aspects, the containment member is located on the strut so at to be mechanically isolated.

In another aspect, and in combination with any of the other aspects, the present disclosure is directed to a transcatheter heart valve prosthesis including an annular stent, valve structure including a plurality of leaflets structure positioned within the stent and coupled to the stent, and a radiopaque marker positioned on the stent adjacent to the inflow end. The annular stent includes a longitudinal axis extending between an inflow end of the stent and an outflow end of the stent and defining an axial direction, the inflow end of the frame being configured to receive antegrade blood flow into the transcatheter heart valve prosthesis when implanted. The plurality of leaflets of the valve structure are joined at commissures. The radiopaque marker is configured to longitudinally align the stent with an annulus of a native heart valve.

In another aspect, and in combination with any of the other aspects, the radiopaque marker is positioned on the stent such that the radiopaque marker is substantially axially aligned with one of the commissures.

In another aspect, and in combination with any of the other aspects, the radiopaque marker is secured to a containment member of the stent, wherein the containment member is located on a strut of the stent.

In another aspect, and in combination with any of the other aspects, the stent includes a plurality of rows formed of a plurality of struts and crowns connecting adjacent struts, wherein crowns of adjacent rows are connected to form nodes, wherein the strut on which the containment member is located is one strut of the plurality of struts and crowns of a first row of the plurality of rows.

In another aspect, and in combination with any of the other aspects, the first row of struts and crowns on which the containment member is located is adjacent the inflow end of the stent such that there are no other rows of struts and crowns proximal of the first row.

In another aspect, and in combination with any of the other aspects, the transcatheter heart valve prosthesis further includes an interior skirt coupled to an interior surface of the stent, and an exterior skirt coupled to an exterior of the stent. In another aspect, the radiopaque marker is secured between the interior skirt and the exterior skirt and substantially axially aligned with one of the commissures.

In another aspect, in combination with any of the other aspects, the valve structure may be attached to the interior skirt or to the interior skirt and struts of the stent.

In another aspect, and in combination with any of the other aspects, the radiopaque marker is a solid circular shape and attached between the interior skirt and the exterior skirt with sutures.

In another aspect, and in combination with any of the other aspects, the radiopaque marker is a hollow ring shape.

In another aspect, and in combination with any of the other aspects, the radiopaque marker is a bar including an opening therethrough, wherein the radiopaque marker is attached to the stent with a suture extending through the opening and wrapped around a portion of the stent.

In another aspect, and in combination with any of the other aspects, the containment member is located on the strut so as to be mechanically isolated.

In another aspect of the present disclosure, and in combination with any of the other aspects, a method of securing a marker to a stent of a transcatheter heart valve prosthesis includes positioning an interior press plate adjacent to an interior surface of a containment member of the stent, wherein the containment member defines a hollow cavity, positioning a solid cylinder of radiopaque material within the hollow cavity, a first end of the solid cylinder of radiopaque material abutting the interior press plate, positioning an exterior press plate adjacent to a second end of the solid cylinder of radiopaque material, and applying a force to the interior press plate and/or the exterior press plate, wherein the force causes the solid cylinder of radiopaque material to fill the hollow cavity and form a first cap on an exterior surface of the containment member and a second cap on an interior surface of the containment member.

In another aspect, and in combination with any of the other aspects, the interior press plate includes a recess that causes formation of the second cap.

Aspects of the present disclosure are also directed to a method for rotationally aligning a transcatheter heart valve prosthesis within a native heart valve including: percutaneously delivering the transcatheter heart valve prosthesis to the native heart valve, wherein the transcatheter heart valve prosthesis includes at least one imaging marker substantially aligned with a commissure of the transcatheter heart valve prosthesis; receiving a cusp overlap viewing angle image of the transcatheter heart valve prosthesis within the native heart valve; determining, based on the cusp overlap viewing angle image and the at least one imaging marker, whether the transcatheter heart valve prosthesis is in a desired rotational orientation; and if the at least one imaging marker in the cusp overlap viewing angle image indicates that the transcatheter heart valve prosthesis is not in the desired rotational orientation, rotating the transcatheter heart valve prosthesis until the transcatheter heart valve prosthesis is in the desired rotational orientation.

In another aspect, and in combination with any of the other aspects, the at least one imaging marker is disposed adjacent an inflow end of the transcatheter heart valve prosthesis.

In another aspect, and in combination with any of the other aspects, percutaneously delivering the transcatheter heart valve prosthesis comprises percutaneously delivering a delivery system including the transcatheter heart valve prosthesis to the native heart valve.

In another aspect, and in combination with any of the other aspects, rotating the transcatheter heart valve prosthesis comprises rotating a handle of the delivery system.

In another aspect, and in combination with any of the other aspects, the at least one imaging marker is substantially aligned with a commissure of a valve structure of the transcatheter heart valve prosthesis.

In another aspect, and in combination with any of the other aspects, the at least one imaging marker comprises three markers with each imaging marker aligned with a commissure of a valve structure of the transcatheter valve prosthesis, and determining whether the transcatheter heart valve prosthesis is in the desired rotational orientation comprises determining, based on the cusp overlap viewing angle image and the three imaging markers, whether two of the imaging markers are substantially aligned on a left side of the cusp overlap viewing angle image.

In another aspect, and in combination with any of the other aspects, the method further includes determining an anterior marker and a posterior marker of the two markers on the left side of the cusp overlap view image.

In another aspect, and in combination with any of the other aspects, determining the anterior marker and the posterior marker comprises moving a viewing angle of an imaging system from the cusp overlap view to a left anterior oblique viewing angle and determining direction of movement of the two markers.

In another aspect, and in combination with any of the other aspects, determining the anterior marker and the posterior marker comprises moving a viewing angle of an imaging system from the cusp overlap view to a right anterior oblique viewing angle and determining direction of movement of the two markers.

In another aspect, and in combination with any of the other aspects, determining the anterior marker and the posterior marker comprises moving a viewing angle of an imaging system from the cusp overlap view to a caudal viewing angle and determining direction of movement of the two markers.

In another aspect, and in combination with any of the other aspects, the at least one imaging marker comprises two imaging markers with each imaging marker aligned with a commissure of a valve structure of the transcatheter valve prosthesis, and determining whether the transcatheter heart valve prosthesis in in the desired rotational orientation comprises determining, based on the cusp overlap viewing angle image and the two imaging markers, whether two of the imaging markers are substantially aligned on a left side of the cusp overlap viewing angle image.

In another aspect, and in combination with any of the other aspects, the at least one imaging marker comprises a single imaging marker substantially aligned with a commissure of a valve structure of the transcatheter valve prosthesis, determining whether the transcatheter heart valve prosthesis is in the desired rotational orientation comprises determining, based on the cusp overlap viewing angle image and the single imaging marker, whether the single imaging marker is on a right side of the cusp overlap viewing angle image and within a zone of confidence.

Aspects of the present disclosure are also directed to a method for rotationally aligning a transcatheter heart valve prosthesis within a native heart valve including: percutaneously delivering the transcatheter heart valve prosthesis to the native heart valve, wherein the transcatheter heart valve prosthesis includes at least one imaging marker substantially aligned with a commissure of the transcatheter heart valve prosthesis; receiving a coronary overlap viewing angle image of the transcatheter heart valve prosthesis within the native heart valve; determining, based on the coronary overlap viewing angle image and the at least one imaging marker, whether the transcatheter heart valve prosthesis is in a desired rotational orientation; and if the at least one imaging marker in the coronary overlap angle image indicates that the transcatheter heart valve prosthesis is not in the desired rotational orientation, rotating the transcatheter heart valve prosthesis until the transcatheter heart valve prosthesis is in the desired rotational orientation.

In another aspect, and in combination with any of the other aspects, the at least one imaging marker is disposed adjacent an inflow end of the transcatheter heart valve prosthesis.

In another aspect, and in combination with any of the other aspects, percutaneously delivering the transcatheter heart valve prosthesis comprises percutaneously delivering a delivery system including the transcatheter heart valve prosthesis to the native heart valve.

In another aspect, and in combination with any of the other aspects, rotating the transcatheter heart valve prosthesis comprises rotating a handle of the delivery system.

In another aspect, and in combination with any of the other aspects, the at least one imaging marker is substantially aligned with a commissure of a valve structure of the transcatheter heart valve prosthesis.

In another aspect, and in combination with any of the other aspects, wherein the at least one imaging marker comprises three markers with each imaging marker aligned with a commissure of a valve structure of the transcatheter valve prosthesis, and determining whether the transcatheter heart valve prosthesis is in the desired rotational orientation comprises determining, based on the coronary overlap viewing angle image and the three imaging markers, whether any of the imaging markers are substantially aligned within an overlap area of the coronary artery ostia of the coronary overlap viewing angle image.

In another aspect, and in combination with any of the other aspects, the at least one imaging marker comprises a single imaging marker substantially aligned with a commissure of a valve structure of the transcatheter valve prosthesis, and determining whether the transcatheter heart valve prosthesis is in the desired rotational orientation comprises determining, based on the coronary overlap viewing angle image and the single imaging marker, whether the single imaging marker is on a right side of the coronary overlap viewing angle image and outside of an overlap area of the coronary artery ostia of the coronary overlap viewing angle image.

In another aspect, and in combination with any of the other aspects, the at least one imaging marker comprises three imaging markers, each of the three imaging substantially aligned with a nadir of a valve structure of the transcatheter valve prosthesis, and determining whether the transcatheter heart valve prosthesis is in the desired rotational orientation comprises determining, based on the coronary overlap viewing angle image and the three imaging markers, whether two of the imaging markers are on a right side of the coronary overlap viewing angle and at least one of the imaging markers is within an overlap area of the coronary artery ostia of the coronary overlap viewing angle image.

In another aspect, and in combination with any of the other aspects, the at least one imaging marker comprises a single imaging marker substantially aligned with a nadir of a valve structure of the transcatheter valve prosthesis, and determining whether the transcatheter heart valve prosthesis is in the desired rotational orientation comprises determining, based on the coronary overlap viewing angle image and the single imaging marker, whether the single imaging marker is within an overlap area of the coronary artery ostia of the coronary overlap viewing angle image.

Other aspects of the present disclosure are directed to a system for delivering a transcatheter heart valve prosthesis, the system including a delivery system including a transcatheter heart valve prosthesis, the transcatheter heart valve prosthesis including a stent, a valve structure positioned within the stent, and at least one imaging marker, and instructions for use including instructions according to any of the aspects of the methods and stents.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings are not to scale.

FIGS. 1A-1G depict illustrations of a transcatheter heart valve prosthesis which includes markers, according to an embodiment hereof.

FIGS. 13-14 depict illustrations of an example delivery system for a transcatheter heart valve prosthesis.

FIG. 16C depicts the cusp overlap view as described above with respect to FIGS. 9A-9B with an illustration of a fluoroscopic image of a native aortic valve in a cusp overlap view and a projection of the markers onto an illustration of the native aortic valve as viewed from the aorta.

FIG. 16D depicts the coronary overlap view as described above with respect to FIGS. 16A-16B with an illustration of a fluoroscopic image of a native aortic valve in a coronary overlap view and a projection of the markers onto an illustration of the native aortic valve as viewed from the aorta.

DETAILED DESCRIPTION

Specific embodiments of the present disclosure are now described with reference to the figures. The following detailed description describes examples of embodiments and is not intended to limit the present technology or the application and uses of the present technology. Although the description of embodiments hereof is in the context of an implantable medical device, e.g., prosthetic heart valve, the present technology may also be used in other devices. Furthermore, there is no intention to be bound by any expressed or implied theory presented in the preceding technical field, background, brief summary or the following detailed description.

The terms "distal" and "proximal", when used in the following description to refer to a delivery system or catheter are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. When the terms "distal" and "proximal" are used herein to refer to a device to be implanted into a patient, such as a heart valve prosthesis, it is in relation to the direct of blood flow. Accordingly, "proximal" means upstream or in the upstream direction and "distal" means downstream or in the downstream direction.

FIGS. 1A-1G depict an example of a transcatheter heart valve prosthesis 100 that includes one or more imaging markers 101 in accordance with an embodiment hereof. One skilled in the art will realize that FIGS. 1A-1G illustrate one example of a transcatheter heart valve prosthesis and that existing components illustrated in FIGS. 1A-1G may be removed and/or additional components may be added to the transcatheter heart valve prosthesis 100.

Figure 1A:
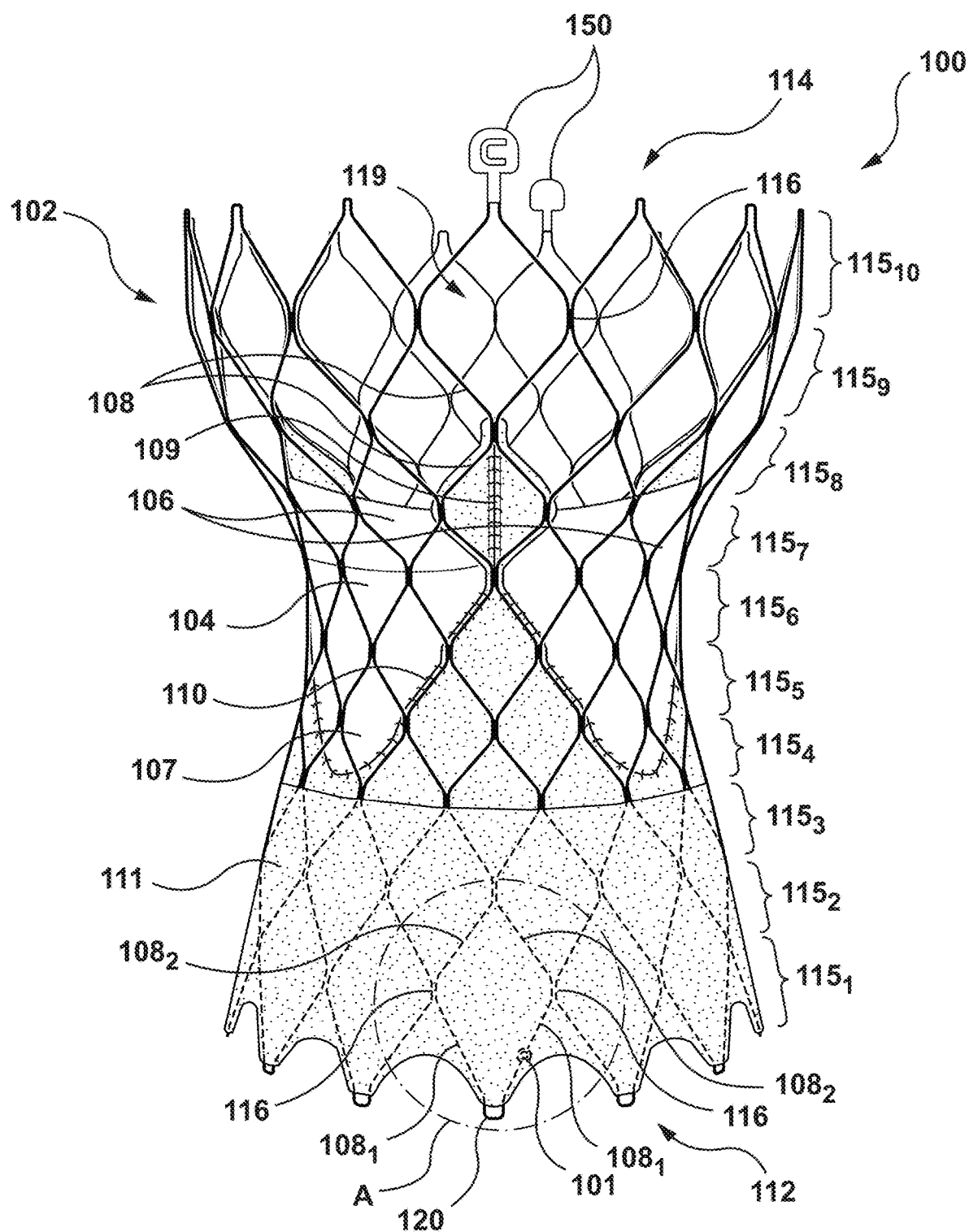
Figure 1B:
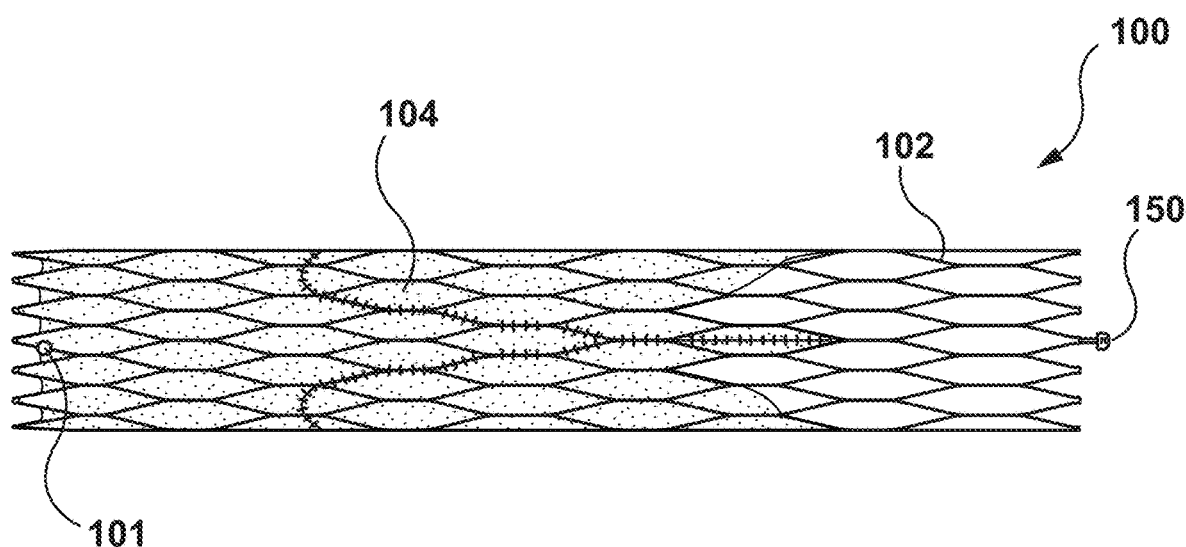
Figure 1C:
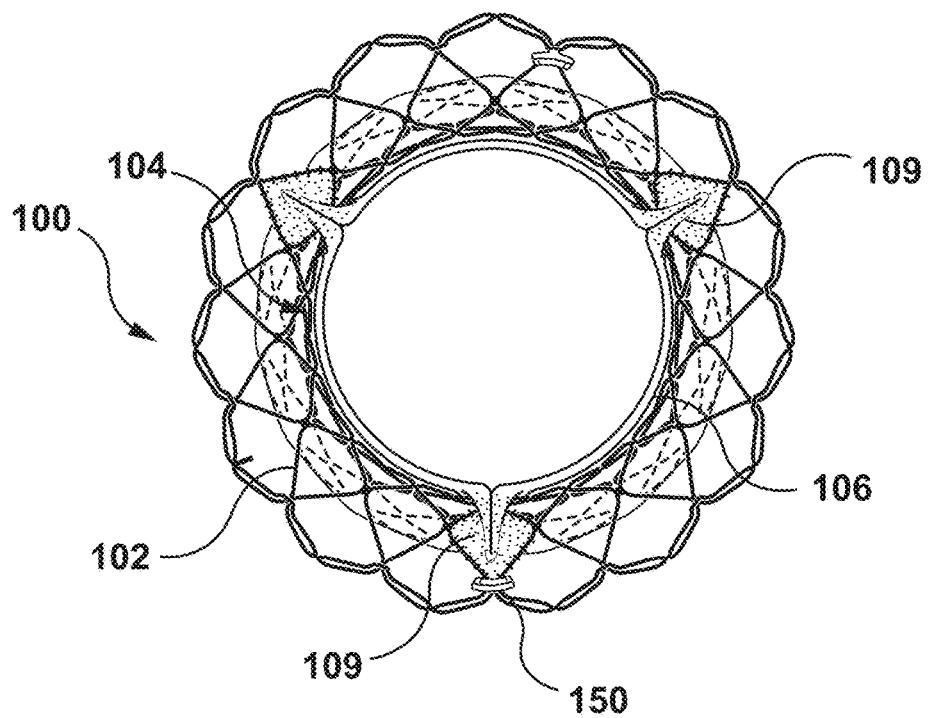
Figure 2A:
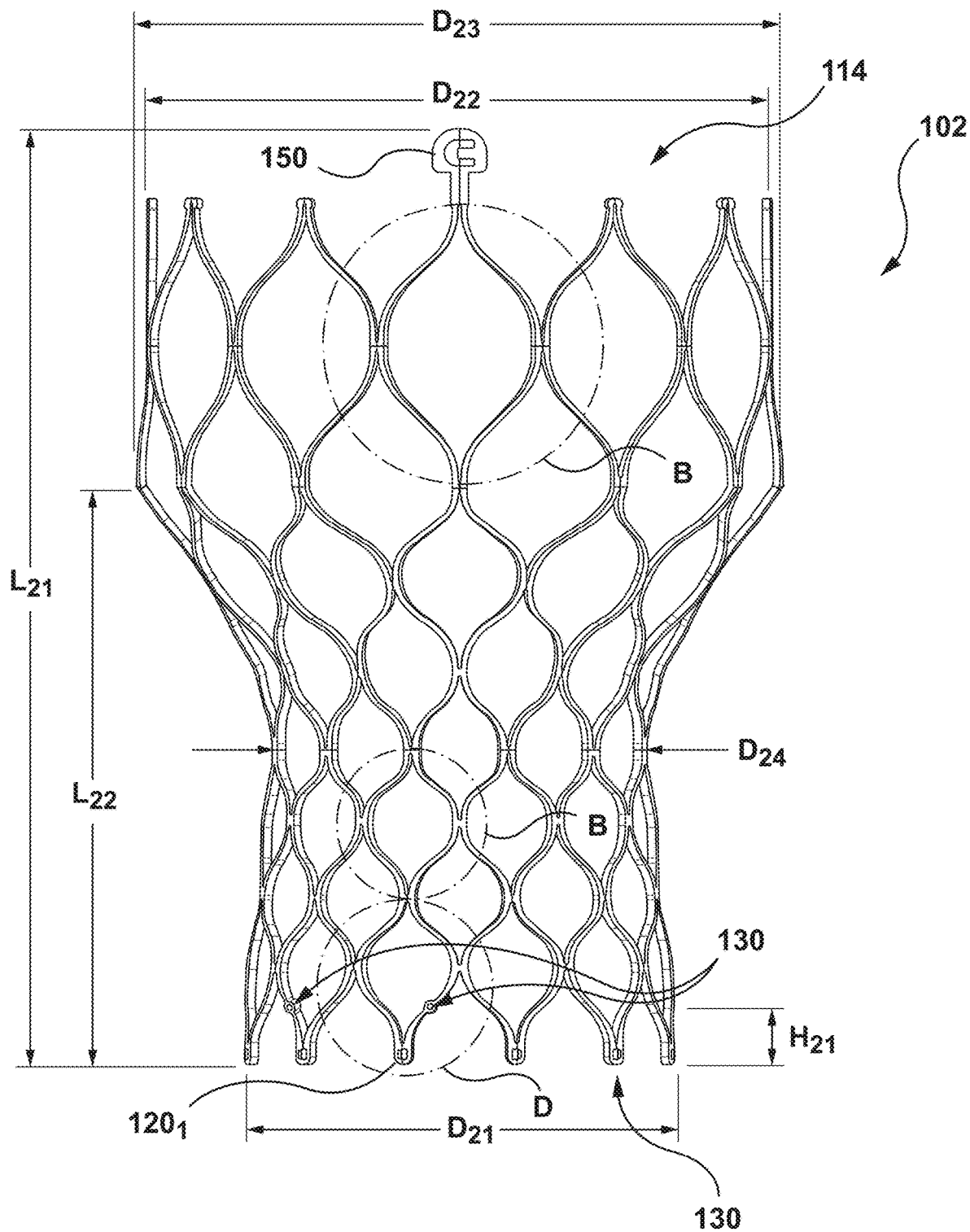
FIGS. 2A-2D depict illustrations of dimensions of the stent of the transcatheter heart valve prosthesis of FIGS. 1A-1G, according to an embodiment hereof.

FIG. 1A illustrates a side view of a transcatheter heart valve prosthesis 100 in a normal or expanded (uncompressed) configuration. FIG. 1B illustrates the transcatheter heart valve prosthesis 100 in a compressed configuration (e.g., when compressively retained within a delivery system such as a distal portion of a delivery system, as known to those skilled in the art). The transcatheter heart valve prosthesis 100 includes a stent or frame 102 (hereinafter "stent") and a valve structure 104. The stent 102 can assume any of the forms described herein and variations thereof, and is generally constructed so as to be expandable from the compressed configuration (FIGS. 1B and 3) to the uncompressed, normal, or expanded configuration (FIGS. 1A and 2A). In some embodiments, the stent 102 is self-expanding. The valve structure 104 is assembled to the stent 102 and provides two or more (typically three) leaflets 106, as illustrated in further detail below with reference to FIG. 1C.

In embodiments, the valve structure 104 can be assembled to the stent 102 in various manners, such as by sewing the valve structure 104 to one or more of the struts 108 or commissure posts defined by the stent 102 using sutures 110. The valve structure 104 is capable of blocking flow in one direction to regulate flow there-through via valve leaflets 106 that may form a bicuspid or tricuspid replacement valve. The valve leaflets 106 are attached to an interior skirt or graft material 107 which encloses or lines a portion of the stent 102 as would be known to one of ordinary skill in the art of prosthetic tissue valve construction. The valve leaflets 106 are sutured or otherwise securely and sealingly attached along their bases with the sutures 110 to the interior surface of the interior skirt 107. Adjoining pairs of leaflets are attached to one another at their lateral ends to form commissures 109, with the free edges of the leaflets forming coaptation edges that meet in an area of the coaptation. In the embodiment shown, the commissures 109 are configured to span a cell of the stent 102, so that force is evenly distributed within the commissures and the stent 102, as described in U.S. Patent Application Publication No. 2006/0265056 A1, which is incorporated by reference herein in its entirety.

The transcatheter heart valve prosthesis 100 of FIGS. 1A-1D can be configured to replace or repair an aortic valve. Alternatively, other shapes are also envisioned, adapted to the specific anatomy of the valve to be repaired (e.g., stented prosthetic heart valves in accordance with the present disclosure can be shaped and/or sized for replacing a native mitral, pulmonic, or tricuspid valve). With the example of FIG. 1A, the valve structure 104 extends less than the entire length of the stent 102, but in other embodiments can extend along an entirety, or a near entirety, of a length of the stent 102. A wide variety of other constructions are also acceptable and within the scope of the present disclosure. For example, the stent 102 can have a more cylindrical shape in the normal, expanded arrangement.

Figure 3:
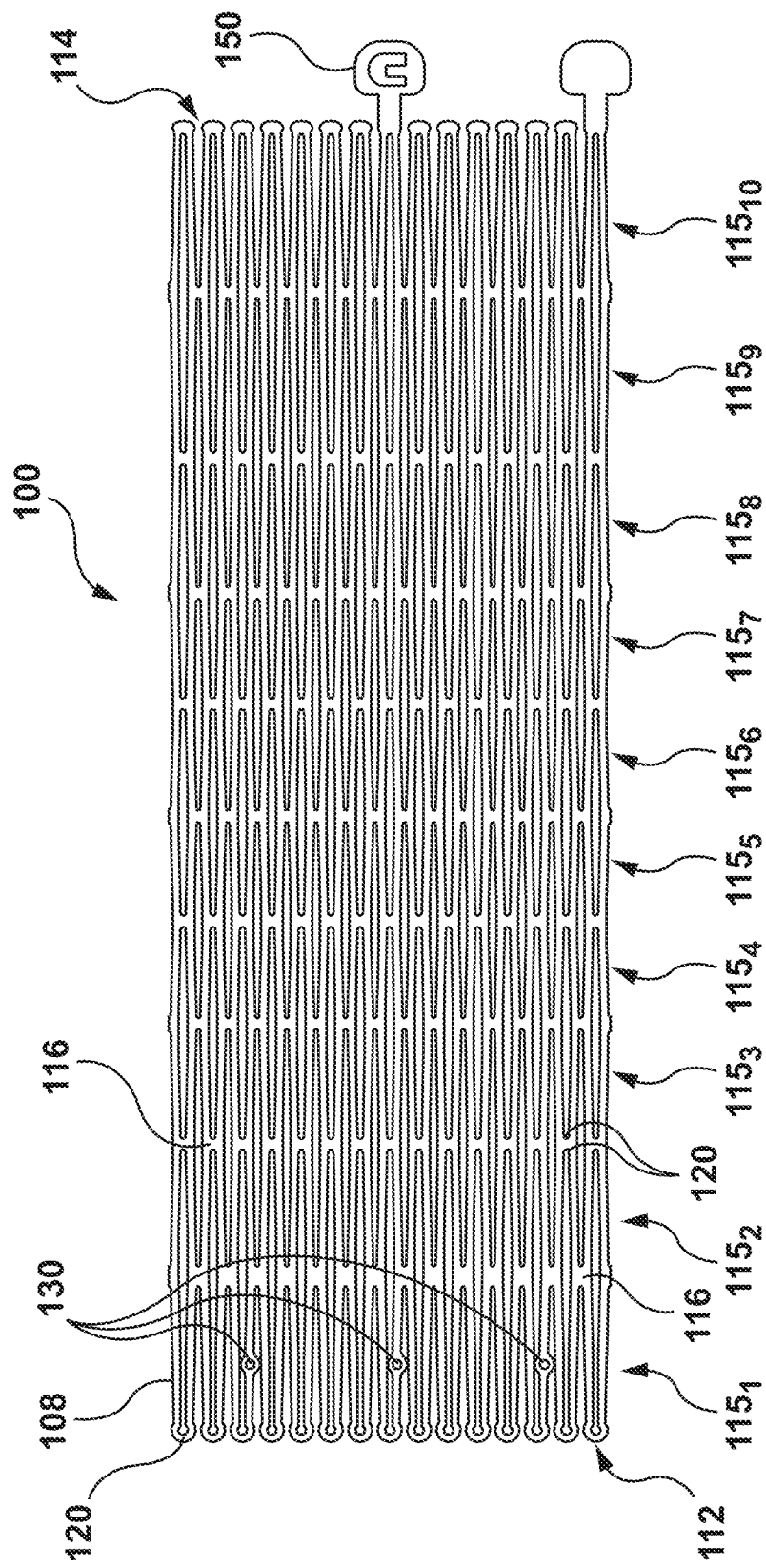
FIG. 3 depicts an illustration of the stent of the transcatheter heart valve prosthesis of FIG. 1A laid out flat and in an "as-cut" configuration, according to an embodiment hereof.

The stent 102 includes struts 108 that operate as support structures arranged relative to each other to provide a desired compressibility and strength to the transcatheter heart valve prosthesis 100. For example, as best illustrated in FIGS. 1A and 2A, the struts 108 are arranged in such a manner as to form cells 119 around the circumference and along the length of the stent 102. The struts 108 can also be described being disposed in rows around the circumference of the stent 102 with crowns 120 joining adjacent struts 108 together to form a zig-zag structure of each row of struts 108 and crowns 120, as best seen in FIG. 3. Longitudinally adjacent rows of struts 108 and crowns 120 are joined together at the crowns 120, thereby forming nodes 116. The arrangement of struts 108 and crowns 120 forming rows of cells 119 forms a central lumen or passageway and can have an inflow end 112 and an outflow end 114. As illustrated, in embodiments, the overall structure formed by the struts 108 and crowns 120 can form the stent 102 having a generally hourglass shape in which the inflow end 112 and the outflow end 114 have a diameter that is larger than a middle portion of the stent 102. The stent 102 can be formed by a laser-cut manufacturing method and/or another conventional stent forming method as would be understood by one of ordinary skill in the art. A lateral cross-section of the stent 102 can be trapezoidal, circular, ellipsoidal, rectangular, hexagonal, square, or other polygonal shape, although at present it is believed that trapezoidal, circular or ellipsoidal may be preferable when utilized with the replacement of an aortic valve.

Figure 1D:
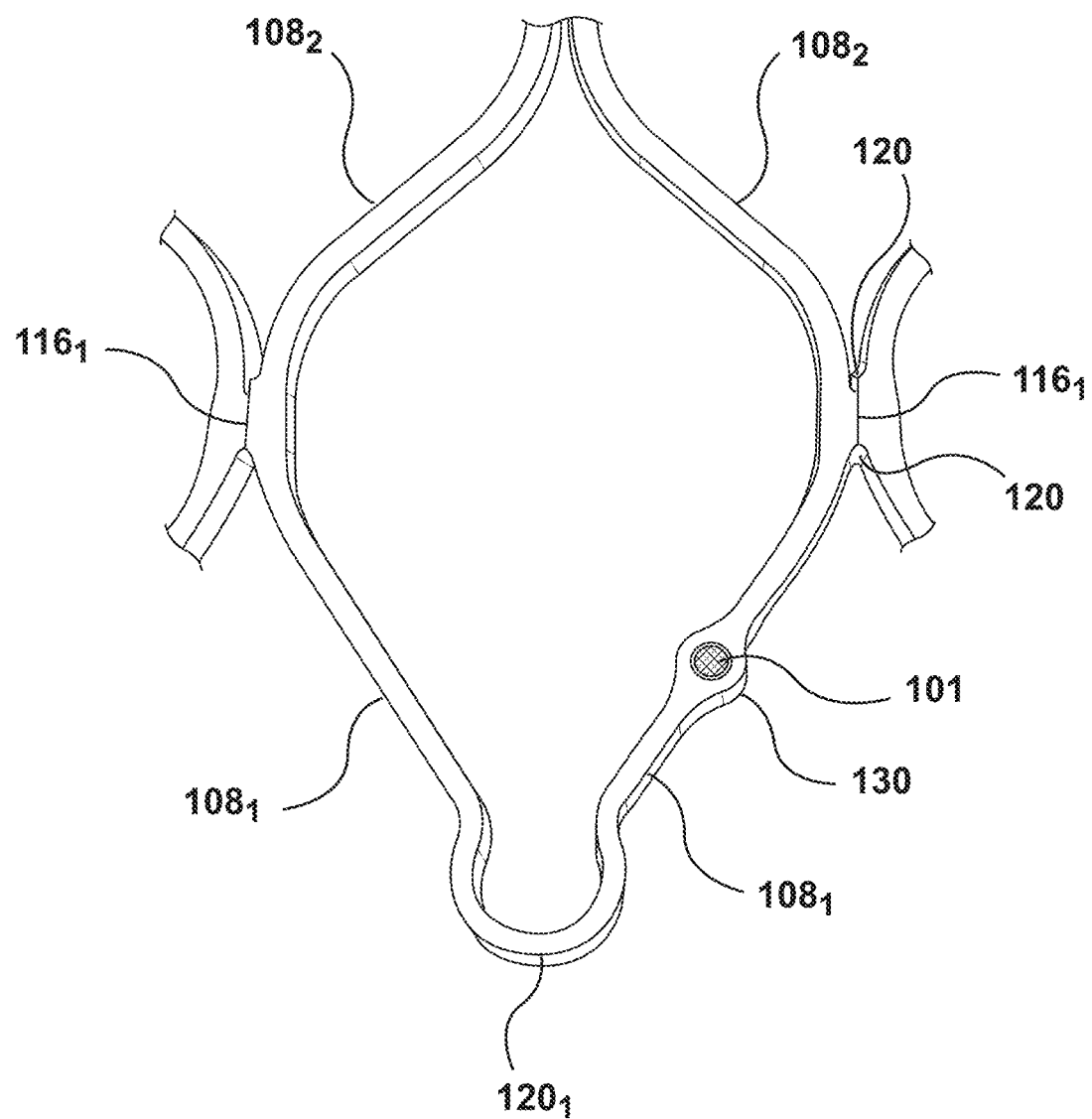

In describing the stent 102 as rows 115 of struts 108, crowns 120, and nodes 116, an example of the stent 102 as shown in FIGS. 1A, 2A, and 3, can include ten (10) rows $115_1$-$115_{10}$, of the struts $108_1$-$108_{10}$ and crowns 120. The struts 108 are arranged in the rows $115_1$-$115_{10}$ around the circumference of the stent 102. The rows $115_1$-$115_{10}$ are arranged axially extended with the row $115_1$ being located at the inflow end 112 and the row 115 to being located at the outflow end 114. The crowns 120 of pairs of the struts 108 in adjacent rows are coupled at the nodes 116. For example, second ends of a pair of struts $108_1$ from the row $115_1$ are joined at a crown 120 that is coupled at a node $116_1$ to an adjacent crown 120 joining first ends of a pair of struts $108_2$ from the row $115_2$, as illustrated in FIG. 1D, which is an enlarged view of region A of FIG. 1A. Similarly, pairs of crowns 120 of struts 108 from adjacent rows 115 are coupled at nodes $116_1$-$116_9$. Further, crowns 120 at the inflow end 112 and the outflow end 114 are not joined to adjacent rows 115 such that the crowns $120_1$ at the inflow end 112 and the crowns $120_{10}$ at the outflow end 114 do not form nodes. While FIGS. 1A, 2A, and 3 illustrate the stent 102 as including 10 rows of struts 108 and crowns 120, one skilled in the art will realize that the stent 102 can include any number of rows of struts and crowns as required by the design of the stent 102. In particular, the examples below for the nominal 23 mm and 26 mm transcatheter heart valve prostheses may include nine (9) rows of struts and crowns.

As illustrated in FIG. 1A, and more clearly in FIGS. 2A and 3, one or more of the struts $108_1$ of the stent 102 includes a containment member 130 that houses the marker 101. As illustrated in FIGS. 1D, 2A, and 3, the containment member 130 is positioned on the strut $108_1$ in the row $115_1$ between a crown $120_1$ and a node $116_1$. The containment member 130 can be configured as a hollow structure or opening having an approximate ring shape, which can receive the marker 101. In any embodiment, the containment member 130 can be configured in a shape that matches a shape of the marker 101. For example, as illustrated in FIG. 1E, which is an enlarged top view of the containment member 130 with the marker 101 removed, the containment member 130 can define a cavity 132 that is circular, e.g., a hollow ring. In an embodiment, as shown in FIG. 1F, which illustrates a cross-sectional view of the containment member 130 of FIG. 1E taken along line A-A, the hollow ring structure of the containment member 130 can include an interior sidewall 180 that reduces in diameter from an exterior surface 181 of the strut $108_1$ to an interior surface 182 of the strut $108_1$. The tapered shape of the interior sidewall 180 may assist in increasing the push out force required to dislodge the marker 101 from the containment member 130 towards the interior surface 182 of the containment member 130. However, as would be understood by those skilled in the art, this tapered shape is not required, and the caps described below with respect to FIG. 1G, or other mechanisms, can provide the necessary prevention against the marker 101 being pushed out of the containment member 130 (i.e., the required force to push out the marker is sufficiently high to prevent the marker from being pushed out of the containment member during crimping into the compressed configuration and subsequent expansion to the radially expanded configuration).

As noted above, the containment member 130 is positioned on the strut $108_1$ in the row $115_1$ between a crown $120_1$ and a node $116_1$. It is desirable that the containment member 130 has a minimal effect on the overall performance of the stent 102. Therefore, it is desirable to locate the containment member 130 where it is "mechanically isolated". The term "mechanically isolated" as used herein means that the containment member 130 is located in an area of low stress on the strut, or, in other words, the containment member 130 is not co-located with the regions of peak tensile or compressive stress during in-service loading. In particular, the struts 108 of the stent 102 are designed such that, during crimping, deployment and in-vivo loading, the peak stresses are at the distal and proximal ends of the strut 108, whereas there is nearly zero stress in the mid-span of the strut. Thus, the containment member 130, and hence the marker 101 located therein, is ideally located in this low stress region. Thus, a stent 102 with a containment member 130 (and a marker 101 located therein) mechanically isolated, i.e., located at a low stress region, has the same mechanical performance as a stent without the containment member 130 in terms of stent stiffness and deformation. The stress distribution at the proximal and distal ends of the strut are unaffected by the introduction of the containment member/marker. Therefore, the stent 102 with the containment member 130 will have the same stiffness and deformation as a stent that is the same in all other aspects expect for the containment member(s) 130.

Explaining in further detail with respect to the present embodiment, stresses are induced in the containment region of the stent 102 during manufacturing and insertion of the marker 101 but they are isolated from the distal and proximal ends of the strut 108 such that the stresses do not interact and cause an increase in one region due to the stress in the other region. Computational modelling to simulate the in-service loading of the stent may be used to identify which region is suitable for placement of the containment members 130. While in this particular embodiment the containment members are located at a mid-span of a strut 108, that is not universal, and is dependent on the strut geometry. In the embodiment shown herein, the struts 108 are tapered from being narrow in the mid-span to being wider at the proximal and distal ends. The width at proximal and distal end is not always the same. Therefore, the stress distribution is not symmetric around the mid span. Computational analysis (or some other method for quantifying the stress distribution) may be used to identify the optimum mechanically isolated position for the containment member 130.

In embodiments, the marker 101 can be attached to, positioned in, and/or formed in the containment member 130 utilizing any type of processes and/or procedure. In some embodiments, the marker 101 is placed in the containment member 130 by press fitting, as described below in further detail with reference to FIGS. 5 and 6A-6E. FIG. 1G is an enlarged view of the containment member 130 in which the marker 101 has been press fit. As illustrated, the marker 101 can be press fit into the containment member 130 such that the marker 101 fills the cavity 132 and forms a cap 134 on the exterior surface 181 of the strut $108_1$ and a cap 136 on the interior surface 182 of the strut $108_1$.

In embodiments, the containment member 130 can be formed to dimensions that secure a marker 101 that is visible during implantation using, for example, a fluoroscope. For example, as illustrated in FIG. 1E, the containment member 130 can be constructed having a width $W_1$. The width $W_1$ can be any width that is required by a particular application and stent 102. For example, the containment member 130 can be formed having a width $W_1$ of approximately 0.3 mm to 0.5 mm. In an embodiment, the width $W_1$ may be 0.41 mm+/−0.03 mm.

In embodiments, the transcatheter heart valve prosthesis 100 can include three (3) markers 101. FIG. 2A, which is an illustration of the stent 102 without the valve structure 104 and the skirts 107, 111, shows three (3) containment members 130 configured to receive markers 101. Similarly, FIG. 3, which is an illustration of the stent 102 without the valve structure 104 and the skirts 107, 111, and shown in a laid out and "as-cut" configuration, shows three (3) containment members 130 to receive markers 101. While FIGS. 1A-1D, 2A, and 3 illustrate one example of the positioning and number of the markers 101, one skilled in the art will realize that the stent 102 can include more or fewer markers 101. In the embodiment shown, each of the markers 101 can be positioned on a strut $108_1$ that is substantially axially aligned with corresponding commissure 109 of the valve leaflets 106. In the present application, the term "substantially axially aligned with a commissure" means that the cell 119 including one of the commissures 109 is axially aligned with a cell 119 including one of the markers 101, including the struts 108 forming the cell. In other embodiments, for example, embodiments wherein the commissures are attached to a commissure post, "substantially axially aligned with a commissure" means that the marker is directly axially aligned with a commissure or within one cell of the commissure. Axially aligning one or more of the markers 101 with one or more of the commissures 109 enables a user to rotationally align the transcatheter heart valve prosthesis 100 in situ such that the commissures 109 do not block access to the coronary ostia.

Further, the markers 101 in the embodiments shown are preferably located at a lengthwise location of the stent 102 that is desired to be aligned with the annulus of the native heart valve when the transcatheter heart valve prosthesis 100 is deployed at the native heart valve. Thus, during implantation, the markers 101 can be used to align the markers 101 with the annulus of the native heart valve to enable better depth positioning of the transcatheter heart valve prosthesis 100 such that it can be more accurately deployed and reduce the incidence rate of requiring a permanent pacemaker (PPM) post-implantation. As shown in the charts below, in the embodiment shown in FIG. 1, depending on the size of the transcatheter heart valve prosthesis, the markers 101 are spaced from the inflow end 112 of the stent 102 at a distance $H_{21}$ of 2.6 mm-3.0 mm for alignment with the native annulus.

Figure 7A:
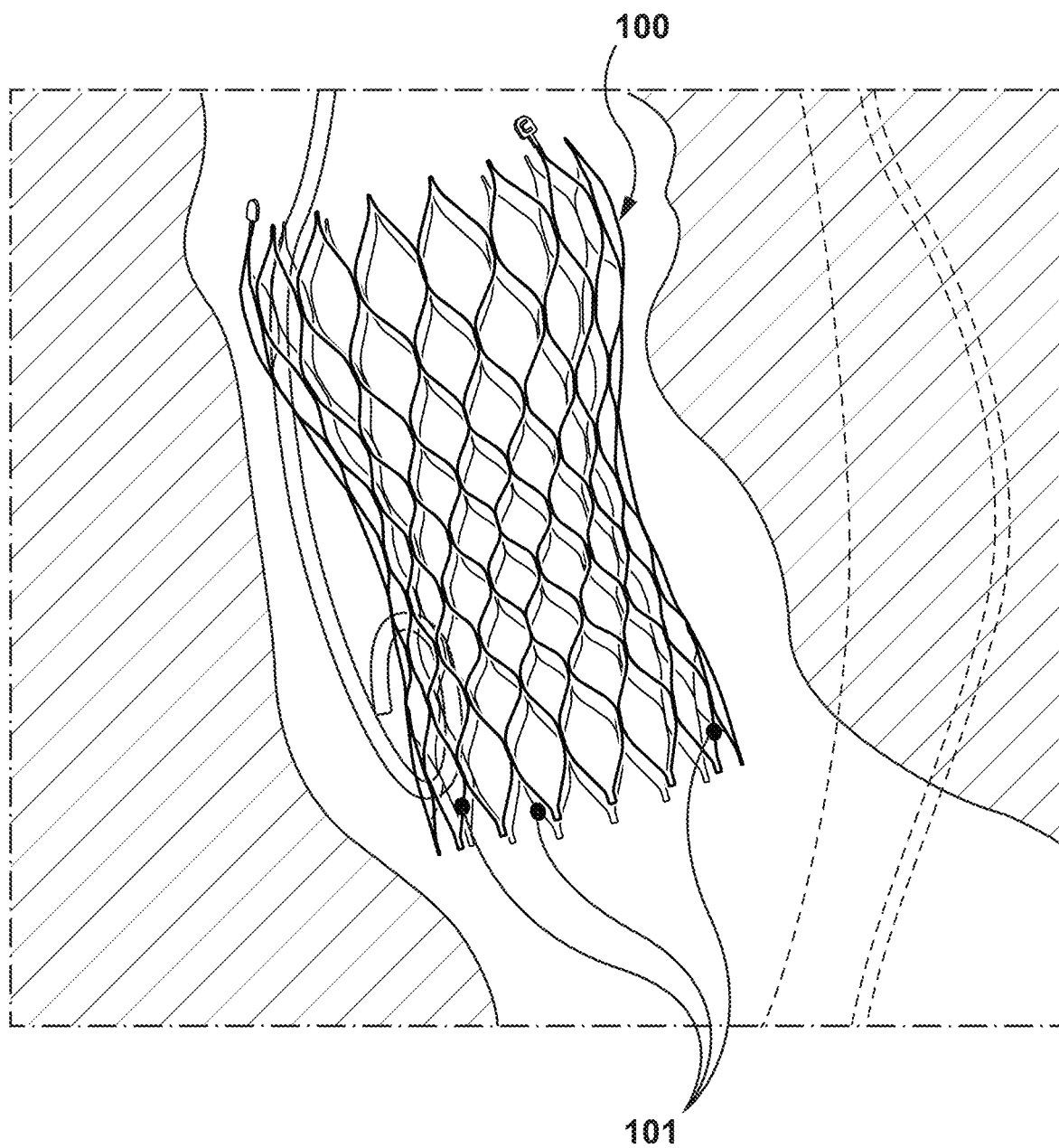
FIGS. 7A-7B depict illustrations of the transcatheter heart valve prosthesis of FIGS. 1A-1G during implantation at a native aortic valve.
Figure 7B:
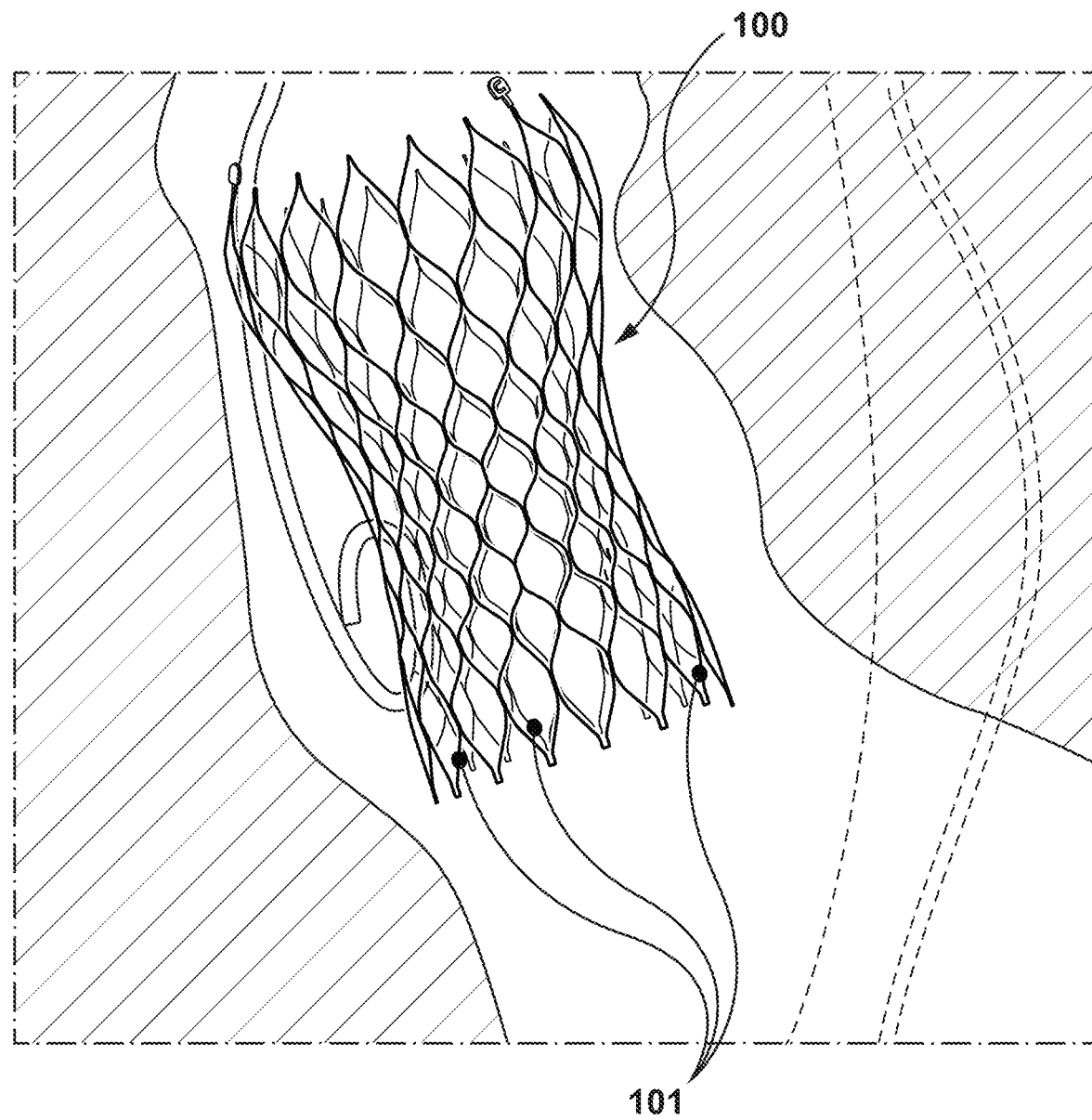

With reference to FIGS. 7A-7B, the use of the three (3) markers 101 located at a lengthwise location of the stent 102 that is desired to be aligned with the annulus will be explained. In particular, the presence of the three (3) imaging markers 101 facilitates identification of when parallax is present in the transcatheter heart valve prosthesis 100 for a given fluoroscopic viewing angle. FIG. 7A shows an example of the transcatheter heart valve prosthesis 100 with parallax present in the viewing angle. As can be seen in FIG. 7A, the three (3) markers 101 are not in a line. Changing the viewing angle through operation of the C-arm gantry can be completed to result in the three (3) markers 101 being aligned, as shown in FIG. 7B. Implant depth relative to the native aortic valve cusps can be more accurately assessed with parallax removed. Although FIGS. 7A and 7B are shown with the transcatheter heart valve prosthesis 100 deployed from a delivery system, those skilled in the art would recognize that parallax and implant depth may be determined using the markers 101 with only a sufficient amount of the transcatheter heart valve prosthesis 100 deployed from a capsule such that the markers 101 are not covered by the capsule. In other words, in some embodiments, a delivery catheter used to deliver the transcatheter heart valve prosthesis 100 includes a capsule at a distal portion thereof that constrains the transcatheter heart valve prosthesis 100 in the radially compressed configuration. When the delivery system is disposed at the treatment site, in this example the native aortic valve, the capsule is withdrawn proximally (in FIGS. 7A and 7B upwardly) to expose the self-expanding transcatheter heart valve prosthesis 100. Thus, the inflow end of the transcatheter heart valve prosthesis 100, including the markers 101, is exposed first, thereby enabling self-expansion. Thus, parallax and implant depth may be determined before full deployment of the transcatheter heart valve prosthesis 100, thereby enabling any correction required without necessitating recapture of a fully deployed transcatheter heart valve prosthesis.

Figure 9A:
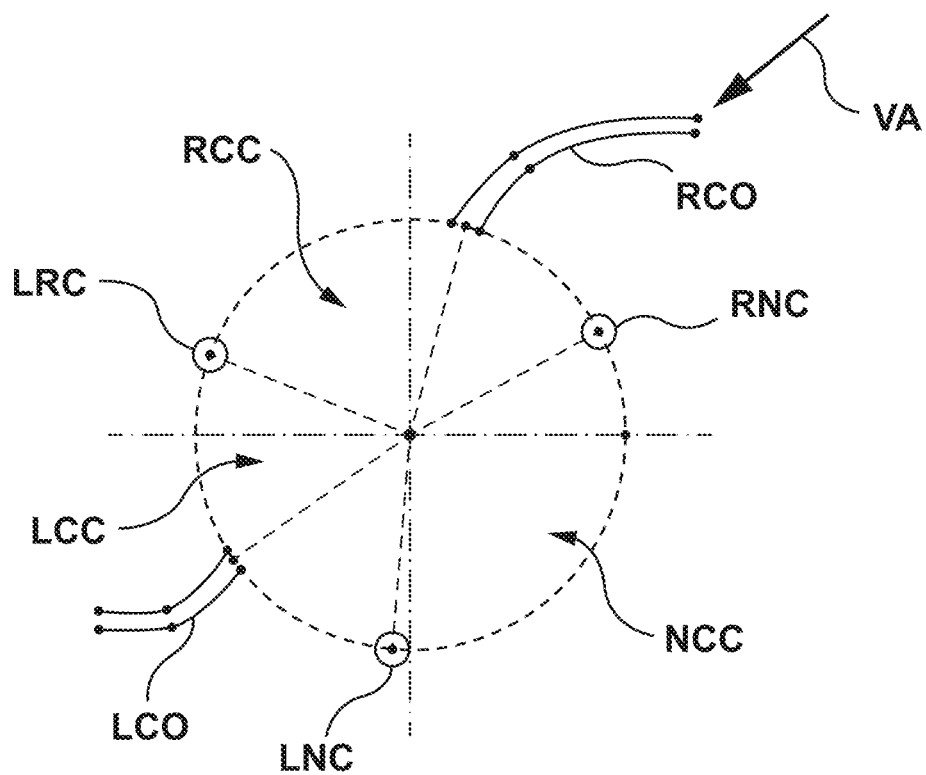
FIG. 9A depicts an illustration of the native aortic valve as viewed from the aorta and depicting the viewing angle for a cusp overlap view.
Figure 9B:
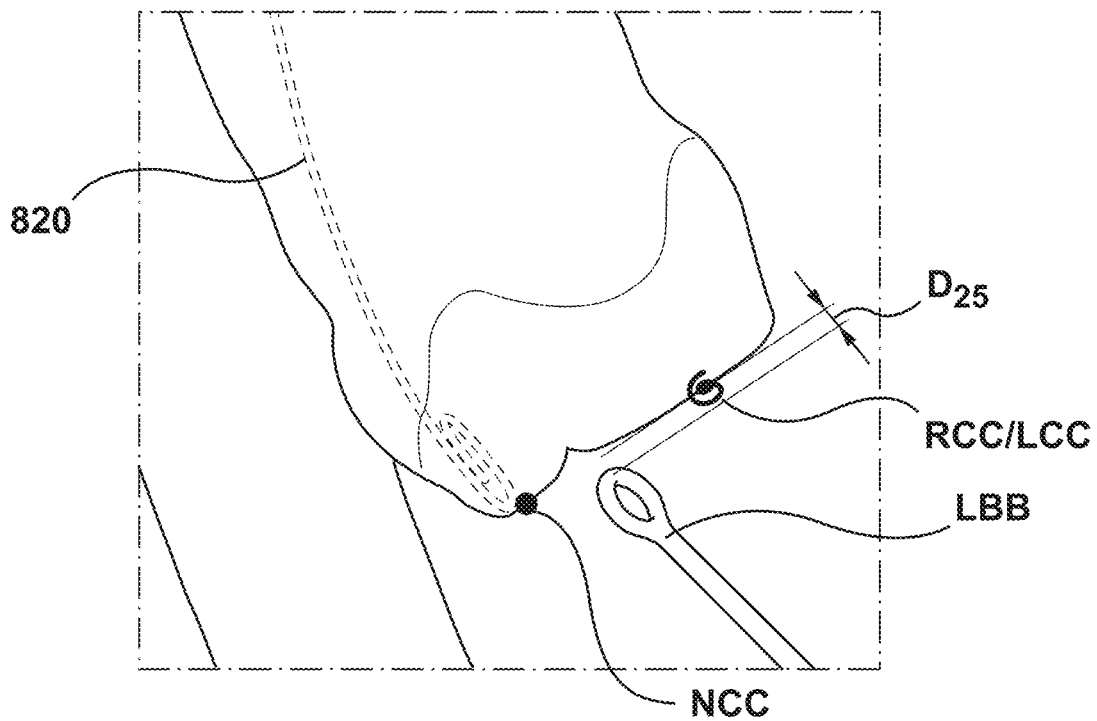
FIG. 9B illustrates an example fluoroscopic image of a native aortic valve using the cusp overlap view.

Further, the cusp overlap view, explained in more detail below, can be used for improved accuracy of implantation depth of the transcatheter heart valve prosthesis 100. Referring to FIG. 9B, which is a cusp overlap view, the left bundle branch LBB of the heart is shown. When using the cusp overlap view with parallax removed, a distance $D_{25}$ from the bottom of the native valve cusps to the left bundle branch LBB is larger than in other views. Those skilled in the art will recognize that the physical distance between the bottom of the native valve cusps and the left bundle branch does not change, but when change the viewing angle of the imaging device, which is shown in two-dimensions, the distance $D_{25}$ appears greater in the cusp overlap view than in other views. This improves accuracy related to depth of the transcatheter heart valve prosthesis 100 in combination with the markers 101 because the relationship between the bottom of the cusps and the left bundle branch can be better seen. Therefore, a clinician can locate the transcatheter heart valve prosthesis 100 deep enough for proper engagement with the annulus of the native heart valve, but not too deep so as to interfere with the left bundle branch LBB.

While FIGS. 1A-1D, 2A, and 3 illustrate one example of the positioning and number of the markers 101, one skilled in the art will realize that the stent 102 can include more or few markers 101, and that they may be located on other locations, as required.

In any embodiment, the imaging marker 101 may include radiopaque or other material that allows the marker 101 to be detected and/or viewed under radiography during the implantation of the transcatheter heart valve prosthesis 100. Examples of radiopaque materials include metals, e.g., platinum-iridium, gold, iridium, palladium, rhodium, titanium, tantalum, tungsten and alloys thereof. Other examples of radiopaque material include polymeric materials, e.g., nylon, polyurethane, silicone, PEBAX, PET, polyethylene, that have been mixed or compounded with compounds of barium, bismuth and/or zirconium, e.g., barium sulfate, zirconium oxide, bismuth sub-carbonate, etc. In embodiments, gold is a preferred marker material due to its visibility enabling a smaller sized containment member 130 such as minimize strain at the location of the containment member and minimize impact on other portions of the stent, such as when crimped. However, this is not meant to be limiting. Further, in addition or instead of the radiopaque materials noted above, the markers 101 can be a feature on the stent 102 that can be seen under fluoroscopy as distinguished from other features of the stent. For example, and not by way of limitation, a containment member without a radiopaque marker disposed therein may be a marker if it can be distinguished in fluoroscopy from struts without a containment member, such as due to the opening within the containment member. Other features such as bulges, thicker struts, protrusions, and/or distinct shapes that can be distinguished in a fluoroscopic image may be considered markers as well.

Returning to FIG. 1A, the transcatheter heart valve prosthesis 100 can also include an exterior skirt 111 coupled to the outer surface of the stent 102 at the inflow end 112 thereof. The exterior skirt 111 may be attached to stent 102 by any suitable means known to those skilled in the art, for example and not by way of limitation, suture/stitches, welding, adhesive, or other mechanical coupling. In an embodiment, the exterior skirt 111 may extend from the inflow end 112 of the stent 102 towards the outflow end 114 such that when the transcatheter valve prosthesis 100 is deployed in situ the exterior skirt 111 is positioned at the native annulus, extends below or above the native annulus, and/or extends between the native leaflets. In embodiments, the exterior skirt 111 longitudinally extends from the inflow end of the stent 102 and over two (2) rows of cells 119 of the stent 102, as shown in FIG. 1A. However, the length of exterior skirt 111 may vary according to application. Since the exterior skirt 111 is coupled to the outer surface of stent 102, longitudinal placement and/or the size and shape thereof may be adjusted or adapted according to each application and to a patient's unique needs. For example, depending on the anatomy of the particular patient, the exterior skirt may be positioned on stent 102 so that in situ the exterior skirt is positioned between the prosthetic heart valve 100 and the interior surfaces of the native valve leaflets, between the prosthetic heart valve 100 and the interior surfaces of the native valve annulus, and/or between the prosthetic heart valve 100 and the interior surfaces of the left ventricular outflow track (LVOT).

The interior skirt 107 is coupled to the inner surface the stent 102. As illustrated in FIG. 1A, the interior skirt 107 longitudinally extends from bases of the leaflets 106 to the inflow end 112 of the stent 102. As such, two layers of skirt material, i.e., a first layer via the exterior skirt 111 and a second layer via the interior skirt 107, extend over the cells 119 located adjacent to the inflow end 112 of the stent 102. The layers of skirt material, i.e., a first layer via the exterior skirt 111 and a second layer via the interior skirt 107, overlap or overlay each other around the inflow end 112 (e.g., the crowns 120₁) of the stent 102. The inflow end 112 is thus sandwiched or positioned between layers of skirt material.

Although the exterior skirt 111 and the interior skirt 107 are described herein as separate or individual components, the exterior skirt 111 and the interior skirt 107 may be formed from the same or a single component. For example, the exterior skirt 111 and the interior skirt 107 may be formed via a single folded component that is coupled to both the inner and outer surfaces of the stent 102 with the fold thereof extending over or around the inflow end 112 of the stent 102. The exterior skirt 111 and the interior skirt 107, respectively, may be formed from the same material. The exterior skirt 111 and the interior skirt 107, respectively, may be formed of a natural or biological material such as pericardium or another membranous tissue such as intestinal submucosa. Alternatively, the exterior skirt 111 and the interior skirt 107, respectively, may be a low-porosity woven fabric, such as polyester, Dacron fabric, or PTFE, which creates a one-way fluid passage when attached to the stent 102. In some embodiments, the exterior skirt 111 and the interior skirt 107, respectively, may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. Elastomeric materials such as but not limited to polyurethane may also be used as a material for the exterior skirt 111 and the interior skirt 107.

In embodiments, as illustrated in FIG. 1A the stent 102 can also include one or more paddles 150 that removably couple the prosthetic heart valve 100 to a delivery system, e.g., as known to those skilled in the art and described, for example, a delivery system such as the EnVeo™ PRO catheter or the EnVeo™ R catheter, from Medtronic, Inc. While FIGS. 1A, 2A, and 3 illustrate two (2) paddles 150, one skilled in the art will realize that the paddles 150 can be replaced with other components such as eyelets, loops, slots, or any other suitable coupling member, and that more or fewer paddles or other coupling members may be utilized. In the embodiment shown, the paddles 150 are radiopaque so as to be visible under fluoroscopy, with one of the paddles 150 including a C-shaped marker to assist with orientation of the transcatheter heart valve prosthesis 100 during implantation. Those skilled in the art would recognize that other asymmetric shapes may be utilized so assist in determining the orientation of the transcatheter heart valve prosthesis 100 during implantation. In embodiments, such as the embodiment of FIGS. 1A, 2, and 3, the paddle 150 with the C-shaped marker is axially aligned with one of the commissures 109 of the valve structure 104, as best seen in FIG. 1A.

In embodiments of the present disclosure, the struts 108 of the stent 102 can be formed from a shape memory material such as a nickel titanium alloy (e.g., Nitinol). With this material, the stent 102 is self-expandable from the compressed configuration to the normal, expanded configuration, such as by the removal of external forces (e.g., compressive forces), such as forces imparted by a delivery catheter. The stent 102 can be compressed and re-expanded multiple times without significantly damaging the structure of the stent 102. In addition, the stent 102 of such an embodiment may be laser-cut from a single piece of material or may be assembled from a number of different components or manufactured from various other methods known in the art.

In embodiments, as described above, the stent 102 can generally be a tubular support structure having an internal area in which the leaflets 106 can be secured. The leaflets 106 can be formed from a variety of materials, such as autologous tissue, xenograph material, or synthetics as are known in the art. In some embodiments, the leaflets 106 may be provided as a homogenous, biological valve structure, such as porcine, bovine, or equine valves. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 106 include DACRON® polyester commercially available from Invista North America S.A.R.L. of Wilmington, DE, other cloth materials, nylon blends, polymeric materials, and vacuum deposition nitinol fabricated materials. In some embodiments, the leaflets 106 can be provided independent of one another and subsequently assembled to the support structure of the stent 102. In some embodiments, the stent 102 and the leaflets 106 can be fabricated at the same time, such as may be accomplished using high-strength nano-manufactured NiTi films produced at Advanced Bioprosthetic Surfaces (ABPS), for example.

In embodiments, the dimensions of the stent 102 of the prosthetic heart valve 100 can vary based on the particular application of the prosthetic heart valve 100. For example, and not by way of limitation, transcatheter heart valve prostheses with different nominal diameters may be provided such that a physician may select the appropriate size based on a patient's anatomy, such as, for example, the diameter of patient's native annulus. FIGS. 2A-2D illustrate various dimensions that define the stent 102 of the transcatheter heart valve prosthesis 100 in accordance with embodiments hereof. As illustrated in FIG. 2A, the stent 102, in an expanded configuration, can be constructed having a diameter $D_{21}$ at the inflow end 112 and a diameter $D_{22}$ at the outflow end 114. The stent 102, in an expanded configuration, can be constructed having a maximum diameter $D_{23}$ and a minimum diameter $D_{24}$. The stent 102, in an expanded configuration, can be constructed having a length $L_{21}$ from the crowns $120_1$ to an end portion of the paddles 150. The stent 102, in an expanded configuration, can be constructed having a length $L_{22}$ from the crowns $120_1$ at the inflow end 112 to the portion of the stent 102 with the maximum diameter. The stent 102, in an expanded configuration, can be constructed having a length $L_{23}$ from the crowns $120_1$ to the portion of the stent 102 with the minimum diameter. The stent 102, in an expanded configuration, can be constructed having a height of the containment member 130 as measured from the crowns $120_1$ to a center of the containment member 130, which is further illustrated in FIG. 2D.

Figure 2B:
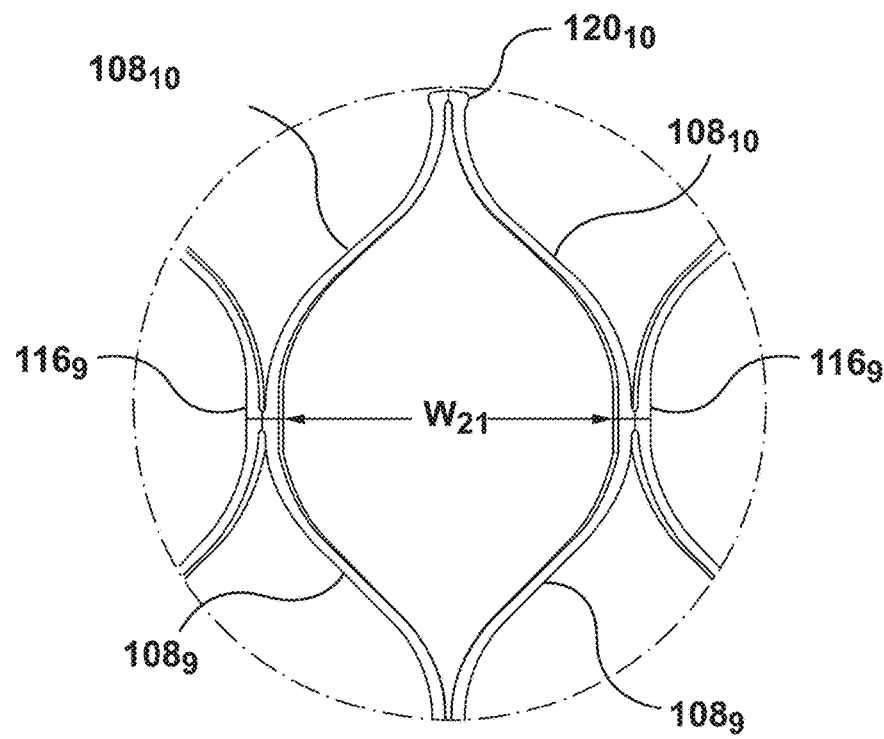
Figure 2C:
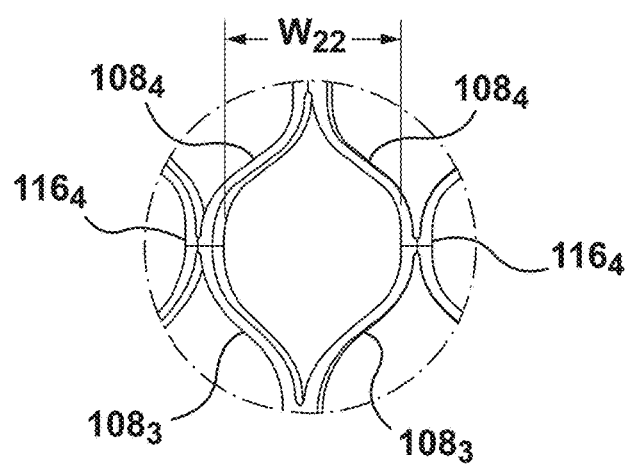
Figure 2D:
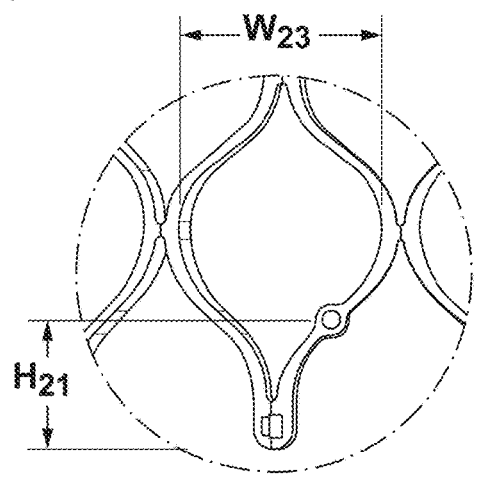

As illustrated in FIG. 2B, which is an enlarged view of the section B, the stent 102, in an expanded configuration, can be constructed having a width $W_{21}$ between nodes $116_9$ that couple the struts $108_9$ to the struts $108_{10}$. As illustrated in FIG. 2C, which is an enlarged view of section C of FIG. 2A, the stent 102, in an expanded configuration, can be constructed having a width $W_{22}$ between nodes $116_4$ that couple struts $108_3$ and $108_4$. As illustrated in FIG. 2D, which is an enlarged view of section D of FIG. 2A, the stent 102, in an expanded configuration, can be constructed having a width $W_{23}$ between nodes $116_1$ that couple struts $108_1$ and $108_2$.

Tables 1-4 includes examples values of the dimensions illustrated in FIGS. 2A-2D for different example transcatheter heart valve prostheses. One skilled in the art will realize that the values of the dimensions of Tables 1-4 are examples and the valves may be altered based on a particular application of the prosthetic heart valve 100. One skilled in the art will realize that any example values of dimensions describe herein are approximate values and can vary by, for example, +/−5.0%, based on manufacturing tolerances, operating conditions, and/or other factors.

TABLE 1

Example 1-nominal 23 mm valve

| Dimension | Example Approximate Value (mm) |
|---|---|
| $D_{21}$ | 23.4 |
| $D_{22}$ | 31.0 to 32.0 |
| $D_{23}$ | 34.0 |
| $D_{24}$ | 19.5 |

TABLE 1-continued

Example 1-nominal 23 mm valve

| Dimension | Example Approximate Value (mm) |
|---|---|
| $L_{21}$ | 48.6 |
| $L_{22}$ | 31.8 |
| $L_{23}$ | 16.6 |
| $H_{21}$ | 3.0 |
| $W_{21}$ | 8.0 |
| $W_{22}$ | 4.55 |
| $W_{23}$ | 4.85 |

TABLE 2

Example 2-nominal 26 mm valve

| Dimension | Example Approximate Value (mm) |
|---|---|
| $D_{21}$ | 26.65 |
| $D_{22}$ | 29.1 |
| $D_{23}$ | 31.75 |
| $D_{24}$ | 22.30 |
| $L_{21}$ | 49.0 |
| $L_{22}$ | 39.19 |
| $L_{23}$ | 23.24 |
| $H_{21}$ | 2.6 |
| $W_{21}$ | 5.7 |
| $W_{22}$ | 4.3 |
| $W_{23}$ | 4.55 |

TABLE 3

Example 3-nominal 29 mm valve

| Dimension | Example Approximate Value (mm) |
|---|---|
| $D_{21}$ | 30.05 |
| $D_{22}$ | 31.0 |
| $D_{23}$ | 33.50 |
| $D_{24}$ | 23.00 |
| $L_{21}$ | 49.0 |
| $L_{22}$ | 39.6 |
| $L_{23}$ | 24.9 |
| $H_{21}$ | 2.6 |
| $W_{21}$ | 6.2 |
| $W_{22}$ | 4.28 |
| $W_{23}$ | 4.92 |

TABLE 4

Example 4-nominal 34 mm valve

| Dimension | Example Approximate Value (mm) |
|---|---|
| $D_{21}$ | 35.90 |
| $D_{22}$ | 37.4 |
| $D_{23}$ | 37.60 |
| $D_{24}$ | 24.20 |
| $L_{21}$ | 49.0 |
| $L_{22}$ | 39.05 |
| $L_{23}$ | 25.66 |

TABLE 4-continued

Example 4-nominal 34 mm valve

| Dimension | Example Approximate Value (mm) |
|---|---|
| $H_{21}$ | 2.6 |
| $W_{21}$ | 6.9 |
| $W_{22}$ | 4.4 |
| $W_{23}$ | 5.6 |

As explained above, the markers 101 may be press fit into the containment members 130. One embodiment of press fitting will be explained below with respect to FIGS. 5 and 6A-6E. In other embodiments, markers 101 can be secured to the stent 102 and/or other parts of the transcatheter heart valve prosthesis 100 in other ways. For example, in other embodiments, radiopaque beads or spheres (or lines of radiopaque beads or spheres) may be swaged, interference fit, etc. into the containment member 130. In some embodiments, the marker 101 can be constructed as part of the containment member 130. For example, the sidewall 180, the exterior surface 181, and the interior surface 182 of the containment member 130 can be painted with a radiopaque material. Likewise, for example, strips of a radiopaque material can be wrapped around the sidewall 180, the exterior surface 181, and the interior surface 182 of the containment member 130. Additionally, for example, the containment member 130 can be constructed to a size such that the ring structure of the containment member 130 may be visible during implantation without the addition of a marker 101.

Figure 4A:
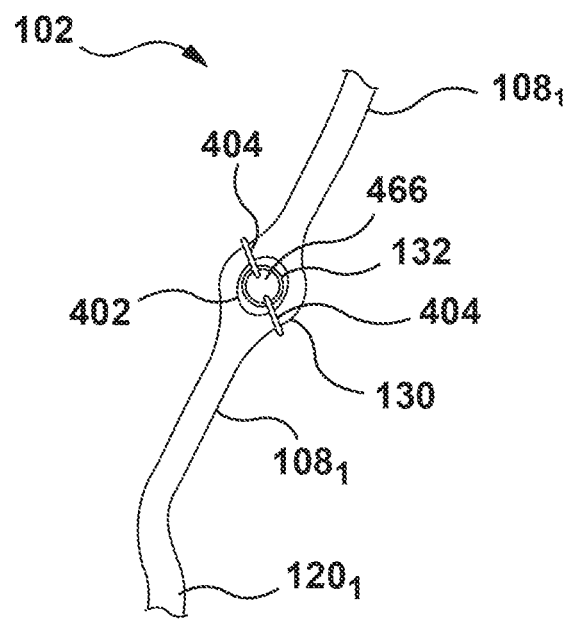
FIGS. 4A-4D depict illustrations of other marker attachments to the stent of the transcatheter heart valve prosthesis of FIGS. 1A-1G, according to an embodiment hereof.

In some embodiments, as illustrated in FIG. 4A, a marker 402 can be secured within the containment member 130 by sutures 404. While FIG. 4A illustrates only a portion of a stent 102, one skilled in the art will realize that the stent 102 can include any of the components discussed above with reference to FIGS. 1A-1G. In this embodiment, the marker 402 can be constructed as a hollow ring with a hole 406 formed within the center of the marker 402, such as a donut shape. The marker 402 can be placed within the cavity 132 of the containment member 130 and secured within the cavity 132 by the sutures 404. That is, the sutures 404 can be looped through the hole 406 around the exterior surface 181, the interior surface 182, and a side surface connecting the exterior and interior surfaces of the containment member 130. The sutures 404 can be secured to the containment member 130 and the marker 402 using any type of knot, such as a square knot.

Figure 4B:
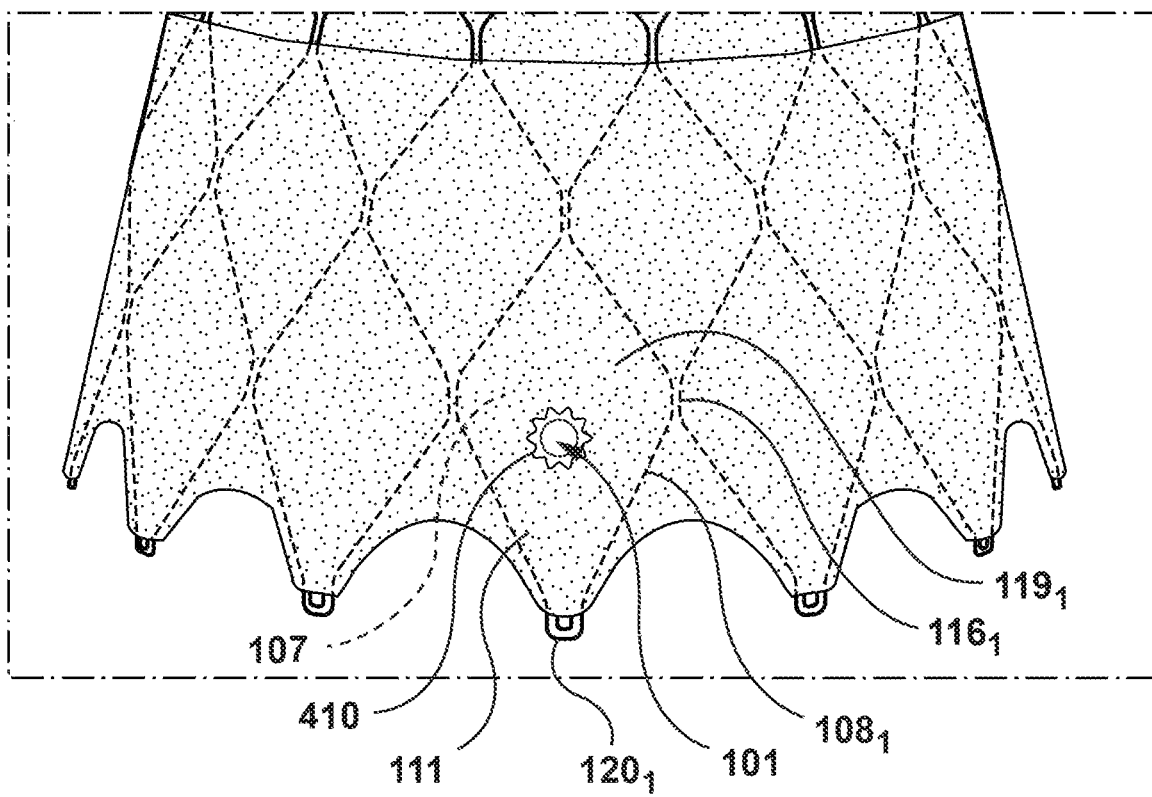

In some embodiments, the stent 102 may not include a containment member 130. In an example of such an embodiment, shown in FIG. 4B, the marker 101 may be attached to the transcatheter heart valve prosthesis 100 by securing the marker 101 between the exterior skirt 111 and the interior skirt 107. As illustrated in FIG. 4B, the marker 101 can be constructed as a solid disk of a radiopaque material. The marker 101 can be placed between the exterior skirt 111 and the interior skirt 107. The marker 101 can be secured between the exterior skirt 111 and the interior skirt 107 by sutures or stiches 410. For example, a line of the sutures 410 can be placed through the exterior skirt 111 and the interior skirt 107 and around a circumference of the marker 101 thereby forming a pocket for the marker 101. Additional sutures 410 can be added to secure the marker 101. As discussed above, the markers 101 may be axially aligned with one or more of the commissures 109 of the valve structure 104. Using the embodiment of FIG. 4B the marker may be attached between the interior and exterior skirts in a cell 119 that is axially aligned with the cell containing one of the commissures 109.

Figure 4C:
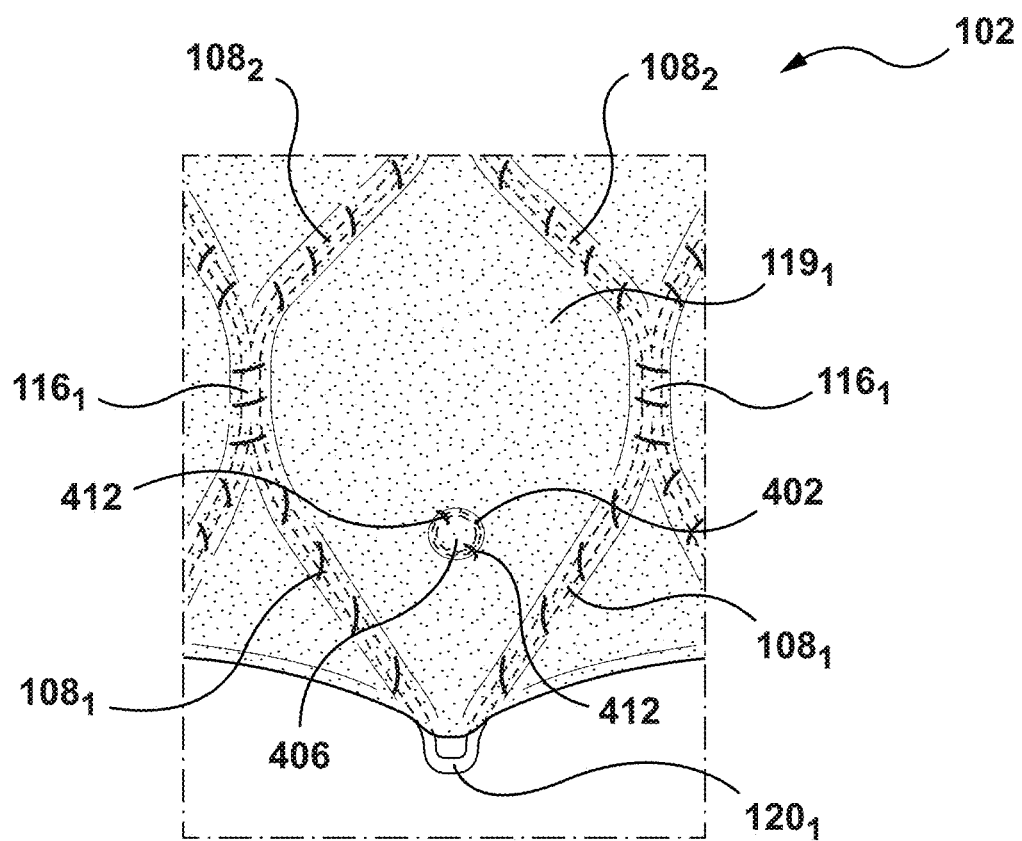

In another embodiment, as illustrated in FIG. 4C, a hollow ring marker 402 (as discussed above in FIG. 4A) can be attached to the transcatheter heart valve prosthesis 100 by securing the marker 402 between the exterior skirt 111 and the interior skirt 107. As illustrated in FIG. 4C, the hollow ring marker 402 can be placed between the exterior skirt 111 and the interior skirt 107 and secured by sutures 412. That is, the sutures 412 can be looped through the hole 406 of the hollow ring marker 402, the exterior skirt 111 and the interior skirt 107. The sutures 412 can be secured to the exterior skirt 111, the interior skirt 107, and the marker 402 using any type of knot, such as a square knot. Similar to as discussed above, the using the embodiment of FIG. 4C the marker 402 may be attached between the interior and exterior skirts in a cell 119 that is axially aligned with the cell containing one of the commissures 109.

Figure 4D:
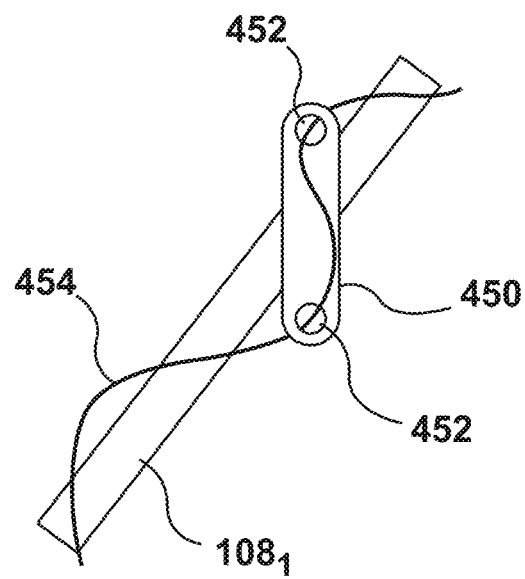

In another embodiment, as illustrated in FIG. 4D, the stent 102 can include a marker 450 that is constructed as a radiopaque band with holes 452. As illustrated in FIG. 4D, the marker 450 can be secured to the strut $108_1$ by a suture or stitch 454. The suture 454 is looped through the holes 452 and around the strut $108_1$ in a helical pattern in order to secure the marker 450 to the strut $108_1$. The suture 454 can secure the marker 450 to the strut $108_1$ using any type of knot, such as a square knot. Similar to as discussed above with respect to FIGS. 1A-1G, the marker 450 and other markers 450 may be secured to a strut 118 that is axially aligned with one of the commissures 109 of the valve structure 104.

In other embodiments, the marker 101 may be formed by applying radiopaque materials to the strut $108_1$ in any shape and/or dimension. One skilled in the art will realize that the marker 101 may be attached to or formed on the stent 102 utilizing any processes as required by the design of the stent 102 and/or application of the prosthetic heart valve 100.

As explained above, in some embodiments, each marker 101 may be press fit into a respective containment member 130. FIGS. 5 and 6A-6E illustrate an example of a method 500 for press fitting the marker 101 into the containment member 130, in accordance with an embodiment hereof. One skilled in the art will realize that FIGS. 5 and 6A-6E illustrate one example of a method using securing the marker 101 within the containment member 130 and that existing operations illustrated in FIGS. 5 and 6A-6E may be removed and/or additional operations may be added to the method 500.

Figure 5:
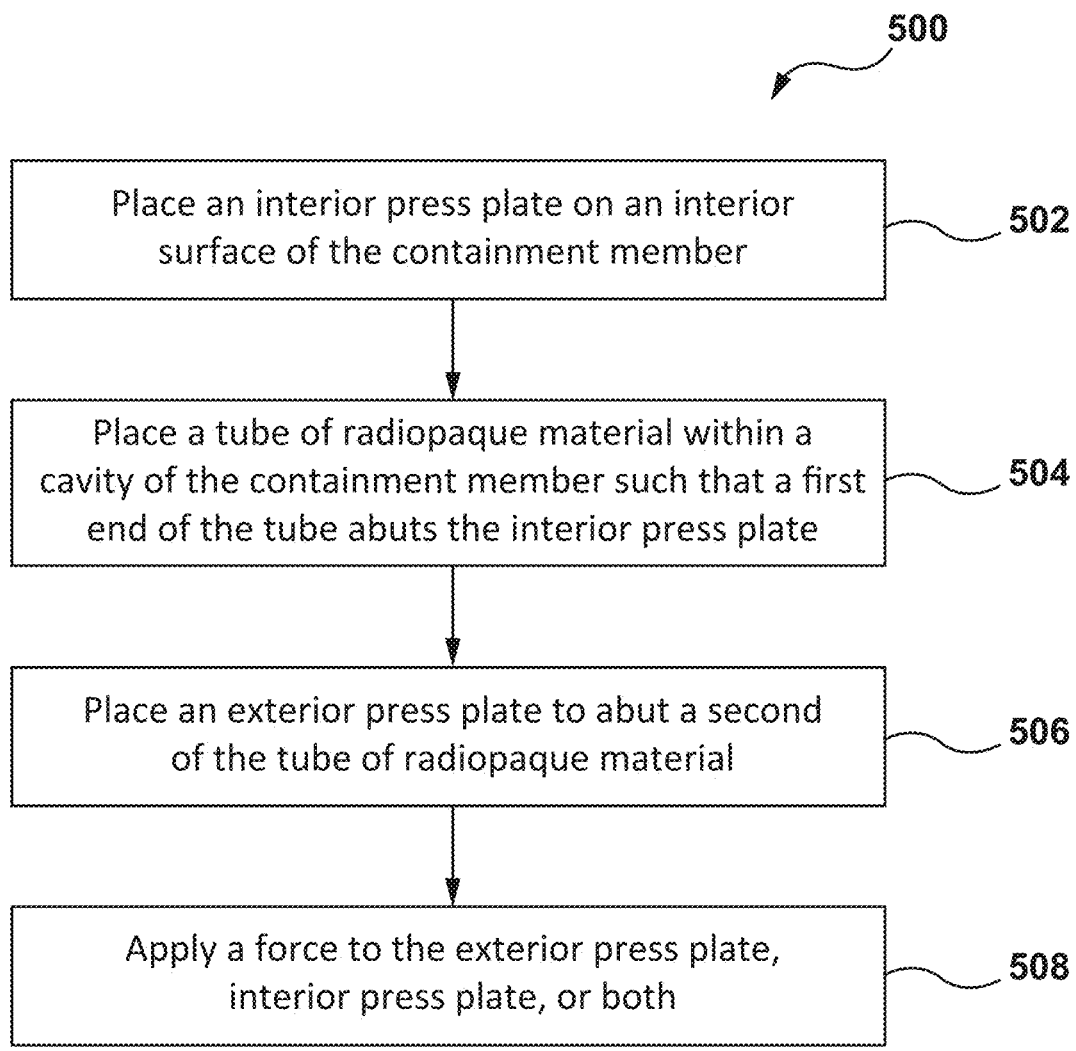
FIG. 5 depicts a flow chart of a method for press fitting a marker into a containment member of the stent of the transcatheter heart valve prosthesis of FIGS. 1A-1G according to an embodiment hereof.
Figure 6A:
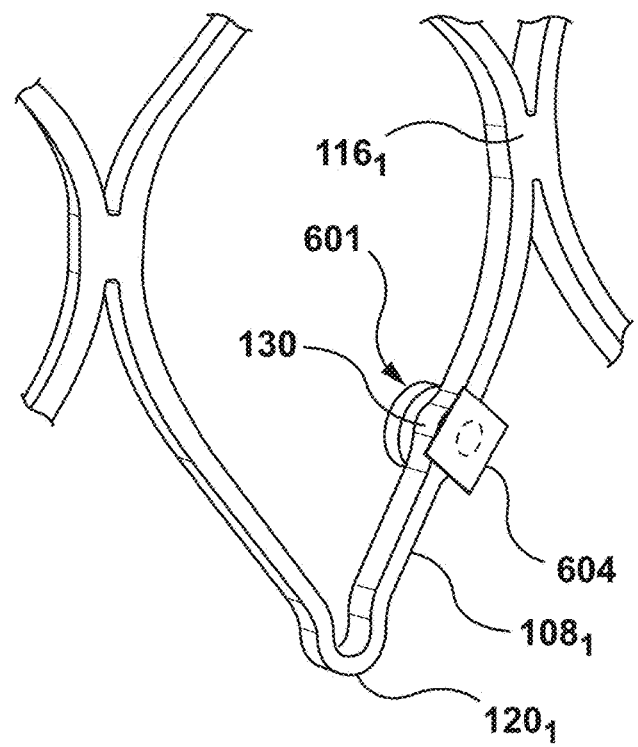
FIGS. 6A-6E depict illustrations the method of FIG. 5 according to an embodiment hereof.
Figure 6B:
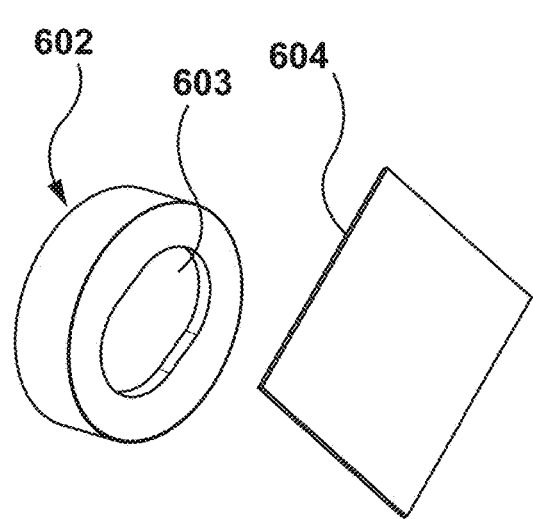
Figure 6C:
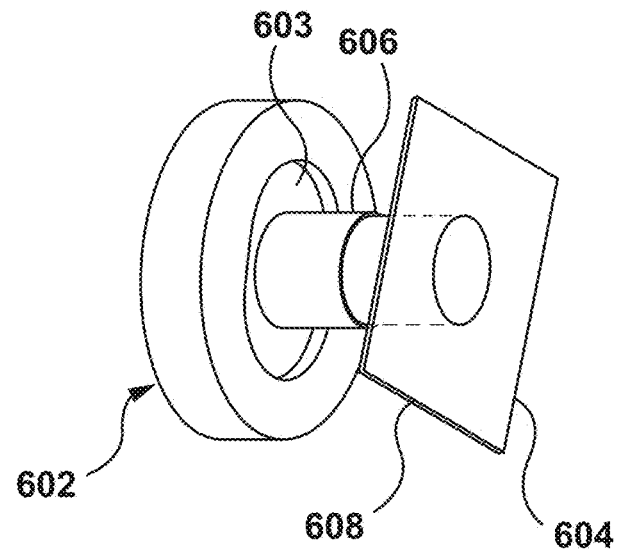
Figure 6D:
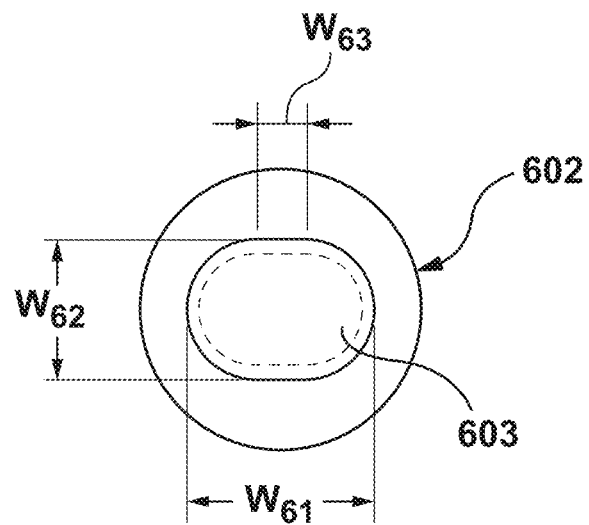

As illustrated in FIG. 5, the method 500 begins with a step 502. In step 502, an interior press plate is placed on an interior surface of the containment member. For example, as illustrated in FIG. 6A, an interior press plate 602 is placed on the interior surface of the containment member 130. As illustrated in FIGS. 6B-6E, the interior press plate 602 can be constructed as an oval disk having an oval recess 603. The oval recess 603 of the interior press plate 602 operates to form the cap 136 on the interior surface 182 of the containment member 130 (as illustrated in FIG. 1G). As illustrated in FIG. 6D, the oval recess 603 of the interior press plate 602 can be constructed having a first width W61, a second width W62, and a third width W63. In some embodiments, the oval recess 603 can be constructed having a first width W61 of approximately 0.76 mm, a second width W62 of approximately 0.56 mm, and a third width W63 of approximately 0.2 mm.

In step 504, a column or solid cylinder 606 of radiopaque material, such as drawn gold, is placed within the cavity of the containment member, with a first end of the solid cylinder abutting the interior press plate 602. In step 506, an exterior press plate 604 is positioned to abut a second end of the solid cylinder 606 of radiopaque material. For example, as illustrated in FIGS. 6B and 6C, the exterior press plate 604 can be constructed as a rectangular plate having a flat surface 608 that abuts a second end of the solid cylinder 606 of radiopaque material. In embodiments, as illustrated in FIG. 6D, when placed within the cavity 132, a portion of the solid cylinder 606 of the radiopaque material extends above the exterior surface 181 of the containment member 130 by a width $W_{65}$. For example, the solid cylinder 606 can extend above the exterior surface 181 of the containment member 130 by a width $W_{65}$ of approximately 0.2 mm. In embodiment, the solid cylinder 606 of the radiopaque material can have a length from the first end to the second end of approximately 0.72 mm.

Figure 6E:
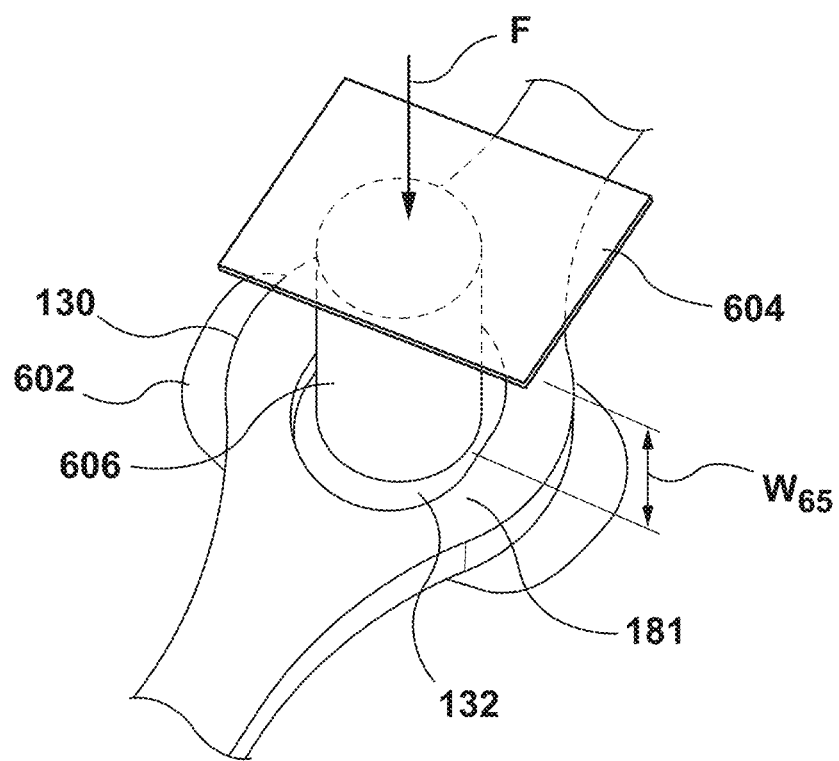

In step 508, a force is applied to the interior press plate 602, the exterior press plate 604, or both. For example, as illustrated in FIG. 6E, a force F can be applied to the exterior press plate 604, while the interior press plate 602 is held stationary. As the force F is applied, the solid cylinder 606 is compressed, causing the radiopaque material to fill the cavity 132 of the containment member 130. Additionally, as the solid cylinder 606 is compressed, the radiopaque material also fills the recess 603 of the interior press plate 602 thereby forming the cap 136 of the marker 101 on the interior surface 182 of the containment member 130 (as shown in FIG. 1G). Additionally, once the cavity 132 of the containment member 130 is filled with the radiopaque material, excess material of the solid cylinder, which extended above the exterior surface 181 of the containment member 130, forms the cap 134 of the marker 101.

A system and method for rotationally aligning a transcatheter aortic valve prosthesis will now be described. The system and method described is with respect to the transcatheter heart valve prosthesis 100 described above, with three (3) markers adjacent an inflow end 112 of the transcatheter heart valve prosthesis 100. However, it would be understood by those skilled in the art that the system and method described may be utilized with other transcatheter heart valve prostheses with more or few markers and disposed in different locations. Specific variations will be discussed in more detail below, but are also not intended to be limiting.

In particular, the desired rotational alignment of the implanted transcatheter heart valve prosthesis 100 is to ensure that the commissures 109 of the transcatheter heart valve prosthesis 100 do not block access to the coronary arteries. In particular, after implantation of the transcatheter heart valve prosthesis 100, it may be necessary for an interventional treatment within one of the patient's coronary arteries, such as angioplasty or stent implantation, for example. However, if one of the prosthetic valve commissures or prosthetic tissue adjacent thereto is blocking the coronary artery, a clinician may not be able to access the coronary artery for the post-implantation procedure. In the embodiments described in more detail below, systems and methods for rotationally aligning a prosthetic valve commissure (such as one of the commissures 109 of the transcatheter heart valve prosthesis 100) with respect to one of the native valve commissures may be sufficient to ensure coronary access. Precise prosthetic valve/native valve commissure alignment is not required as the goal is coronary access. Other benefits from substantial commissure alignment include, improved valve durability and resistance to thrombogenicity, and potential alignment of a second transcatheter heart valve prosthesis in a valve-in-valve procedure. With transcatheter aortic valve replacement procedures being performed using 2-dimensional imaging, such as fluoroscopy, the rotational position of prosthetic valve commissures with respect to the native valve commissures or coronary ostia is difficult to determine.

Figure 15:
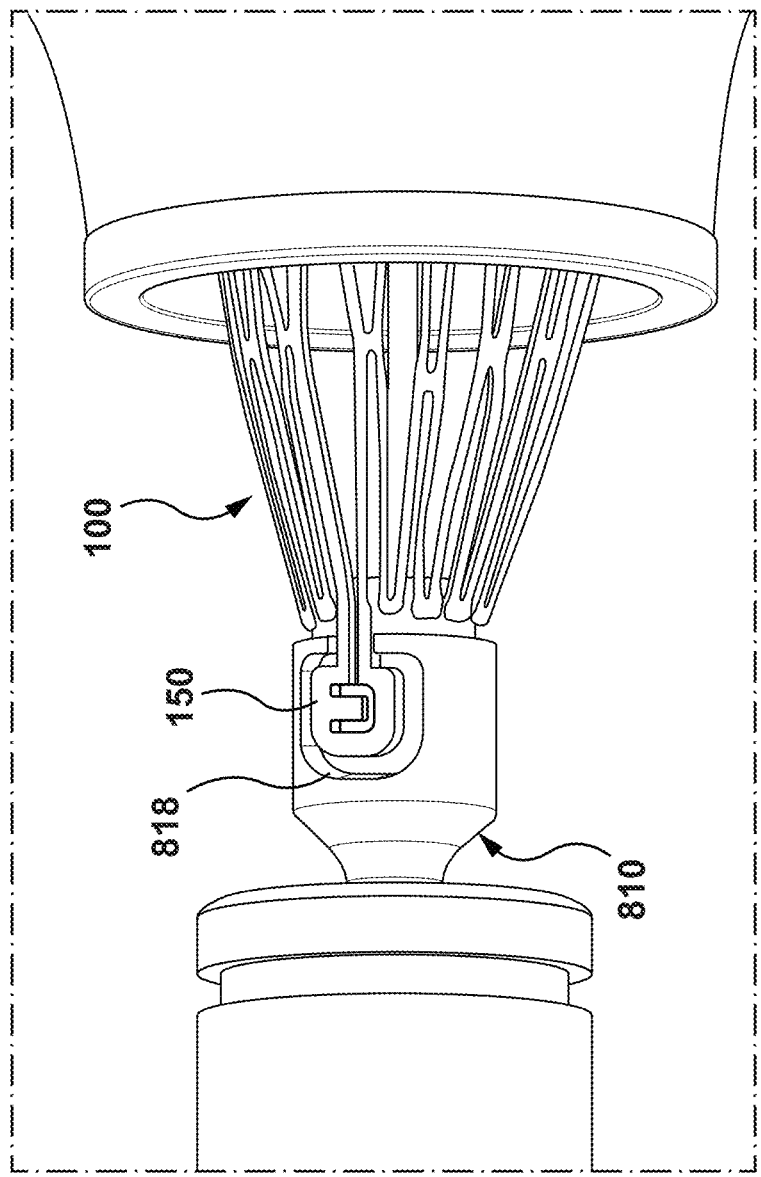
FIG. 15 depicts an illustration of a portion of a transcatheter heart valve prosthesis be loaded into a delivery system.

Prior to a discussion of the system and method for rotationally aligning a transcatheter heart valve prosthesis, an example delivery system 800 for a self-expanding transcatheter heart valve prosthesis such as the transcatheter heart valve prosthesis 100 will be described briefly with respect to FIGS. 13-15. In particular the delivery system 800 includes a handle 802. The handle 802 enables a clinician to manipulate a distal portion of the delivery system 800 and includes actuators for moving parts of the delivery system relative to other parts. In the delivery system 800, an outer shaft 804 is coupled to an actuator of the handle 802 for moving the outer shaft 804 relative to an inner shaft 812. A distal portion of the outer shaft 804, referred to as a capsule 806, is configured to surround a transcatheter heart valve prosthesis during delivery to the treatment site, e.g., a native heart valve and is retracted from the transcatheter heart valve prosthesis to expose the transcatheter heart valve prosthesis such that it self-expands. The inner shaft 812 is coupled to the handle 802 and movement of the handle translates to movement of the inner shaft 812 and a distal tip 808 coupled to a distal end of the inner shaft 812. The inner shaft 812 and distal tip 808 may also be translated relative to the outer shaft 804 and the handle 802 via a tip retractor. In the embodiment shown, a middle member 814 is disposed between the inner shaft 812 and the outer shaft 804, and the middle member 814 includes a retainer or spindle 810 attached to a distal portion thereof for receiving the paddles 150 of the transcatheter heart valve prosthesis 100.

A flush port 816 is disposed on the handle 802. In the delivery system 800 shown, when the transcatheter heart valve prosthesis 100 is properly loaded in to the delivery system 800, certain relationships between features or the transcatheter heart valve prosthesis 100 and features of the delivery system 800 are present, which may assist in predicting the proper rotational orientation of the transcatheter heart valve prosthesis 100. In particular, when loading the transcatheter heart valve prosthesis 100 into the delivery system 800, the paddles 150 are placed into paddle pockets 818 of the spindle 810 at 180° apart from each other, as shown in FIG. 15. As described above, the paddle 150 with the C-shaped marker (sometimes referred to as a "C-tab" or "C-paddle") is aligned with one of the commissures 109 of the transcatheter heart valve prosthesis 100. Further, when the transcatheter heart valve prosthesis 100 is loaded into the delivery system, the C-paddle 150 is located in the paddle pocket 818 that is aligned with the flush port 816 on the handle 802 of the delivery system 800.

As noted above, this is a brief description of an example delivery system 100. Other parts shown in FIGS. 13-15 are not described in detail herein and would be apparent to those skilled in the art.

Figure 8A:
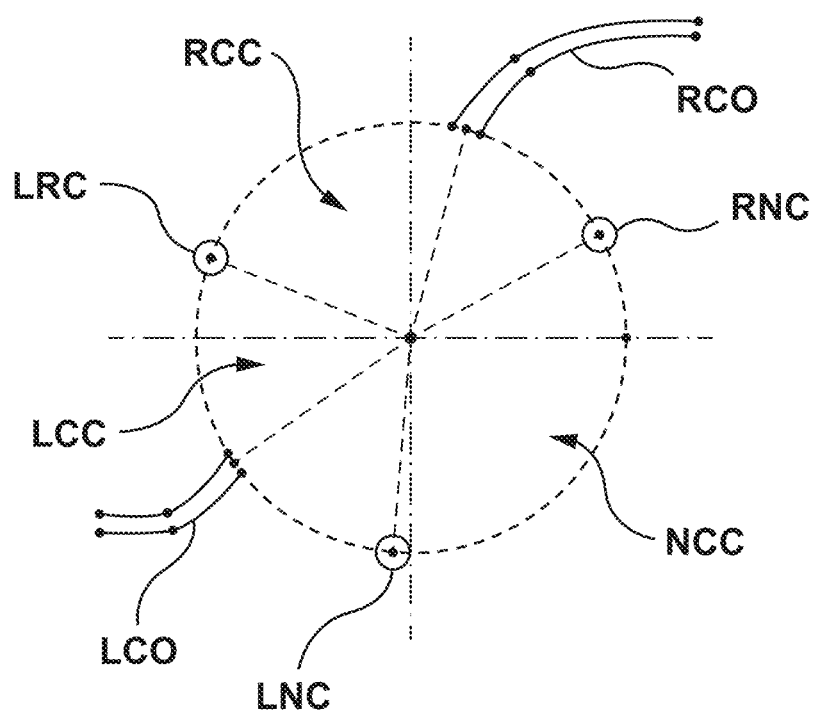
FIGS. 8A-8B depict schematic illustrations of a native aortic valve as viewed from the aorta, showing various features of the native aortic valve.
Figure 8B:
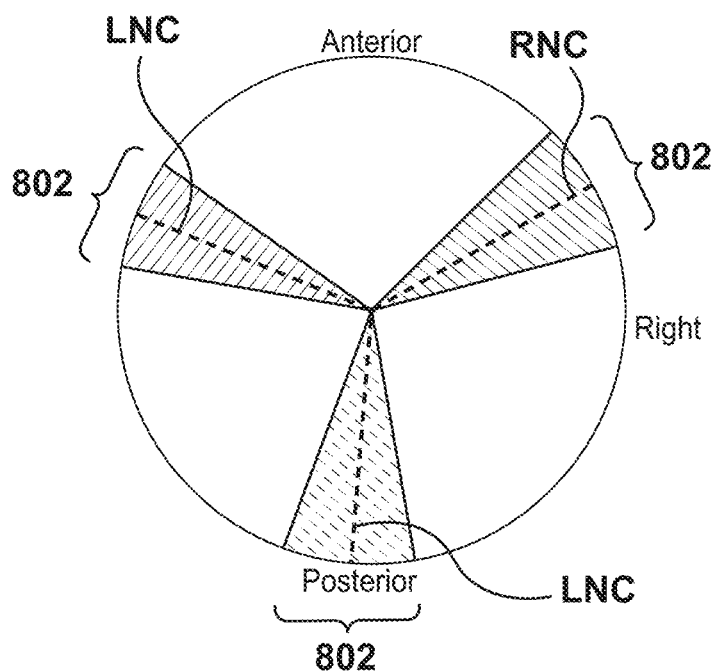

Referring now to FIGS. 8A and 8B, they show schematic illustrations of an aortic valve in a view from the aorta. As shown in FIGS. 8A and 8B, the native aortic valve includes three leaflets or cusps: the left coronary cusp LCC; the right coronary cusp RCC; and the non-coronary cusp NCC. As known to those skilled in the art, the right coronary artery RCO includes an ostia or opening in the sinus of Valsalva, superior to the right coronary cusp RCC and inferior to the sinotubular junction (not shown). Similarly, the left coronary artery LCO includes an ostia or opening in the sinus of Valsalva, superior to the left coronary cusp RCC and inferior to the sinotubular junction (not shown). Further, the non-coronary cusp NCC is in the sinus that does not include an ostia or opening for a coronary artery. As known to those skilled in the art, and shown in FIGS. 8A-8B, the leaflets or cusps are joined at commissures. Thus, the left-right commissure LRC is where the left coronary cusp LCC and the right coronary cusp RCC are joined, the right-non-coronary commissure RNC is where the right coronary cusp RCC and the non-coronary cusp NCC are joined, and the left-non-coronary commissure LNC is where the left coronary cusp LCC and the non-coronary cusp NCC are joined. As can further be seen in FIG. 8B, the commissures are not always in the same location for all patients. Therefore, for each commissure location, there is marked a commissure zone 801, which shows patient specific variation of 10-20 degrees in the location of the commissures. Further, it is noted that the commissures are not exactly 120° apart. Instead, on average, the left-right commissure LRC is closer to the left-non-coronary commissure LNC, at approximately 108°, than to the other two commissures. Further, the location of the ostia or coronary take-off of the left and right coronary arteries may vary approximately 15-20 degrees depending on patient anatomy.

In Tang et al., "Alignment of Transcatheter Aortic-Valve Neo-Commissures (ALIGN TAVR)", it is described that with a transcatheter heart valve prosthesis (Evolut™) similar to the transcatheter heart valve prosthesis 100 and a delivery system (Evolut™ delivery system) similar to the delivery system 800, pointing the flush port 816 at 3 o'clock when inserting the delivery catheter into the patient results in fewer incidences of coronary artery overlap than inserting the delivery catheter with the flush port at 12 o'clock. However, there remained approximately 24% of studied cases where there was coronary overlap with one or both of the coronary arteries. This is likely due to variations in patient anatomies with respect to the patient's aortic valve regarding locations of the coronary artery ostia or take-off and the vascular path for a transcatheter valve to reach the aortic valve. With the systems and methods described herein, the incidences of coronary overlap can be reduced. In particular, with the systems and methods described herein include a pre-procedure work-up to determine proper entry orientation of a delivery system, checking the orientation of the delivery system during delivery, checking the orientation of the transcatheter heart valve prosthesis prior to full deployment, and, if necessary, rotating the transcatheter heart valve prosthesis to the desired orientation prior to full deployment thereof.

With this understanding, imaging systems such as fluoroscopic imaging systems used during transcatheter aortic valve replacement procedures generally include a C-arm gantry that enables different viewing angles of the native aortic valve. One particular viewing angle is a "cusp overlap view". In the cusp overlap view, as shown in FIG. 9A, the viewing angle VA of the imaging system is such that the right coronary cusp RCC and the left coronary cusp RCC overlap each other. FIG. 9A shows the viewing angle as indicated by the arrow VA. FIG. 9B shows a fluoroscopic image using the cusp overlap view. In particular, as shown in FIG. 9B, as indicated by the dots RCC/LCC, the right coronary cusp RCC and the left coronary cusp LCC are aligned with each other, i.e., they overlap. In the cusp overlap view, the non-coronary cusp NCC is to the left of the right coronary cusp RCC and the left coronary cusp LCC, as also shown in FIG. 9B. In certain embodiments, during a transcatheter aortic valve replacement, a pigtail catheter 820 is placed in the basal portion of the non-coronary cusp NCC, as shown in FIG. 9B. It is noted that the FIGS. 9A, 10A, 10C, 10E, 10G, and 10I show an idealized native aortic valve with the native commissures spaced at 120° around the circumference of the native aortic valve sinus. As noted above, patient anatomies vary from this idealized representation.

With the above understanding of the cusp overlap view and the markers 101 in the transcatheter heart valve prosthesis 100 described above, a system and method of rotationally aligning the transcatheter heart valve prosthesis 100 will now be described. As known to those skilled in the art, the transcatheter heart valve prosthesis 100 may be delivered percutaneously via femoral access. In particular, in the example of a self-expanding transcatheter heart valve prosthesis, e.g. the transcatheter heart valve prosthesis 100, the prosthesis is constrained in a radially compressed configuration by, for example, the capsule 806 of the delivery system 800. Characteristics of a patient's native anatomy may be determined prior to starting the procedure, such as by a CT scan. Using this planning CT, a determination may be made prior to the procedure regarding orientation of the delivery system, and hence the transcatheter heart valve prosthesis, when delivering the transcatheter heart valve prosthesis. For example, and not by way of limitation, the delivery system 800 is arranged such that the flush port 816 is aligned with the C-paddle 150 of the transcatheter heart valve prosthesis 100, which is aligned with one of the commissures 109 of the valve structure 104. As explained in Tang, orienting the flush port 816 at 3 o'clock may reduce coronary artery overlap. However, using pre-procedure CT, the orientation of a feature of the delivery system, such as the flush portion 816, that has a known relationship to a feature of the transcatheter heart valve prosthesis, such as one of the commissures 109 of the transcatheter heart valve prosthesis 100, may be further defined by the specific patient anatomy. Thus, using pre-procedure planning, a prediction can be made regarding a preferred orientation of the delivery system, such as the delivery system 800, to reduce coronary artery overlap.

Figure 10A:
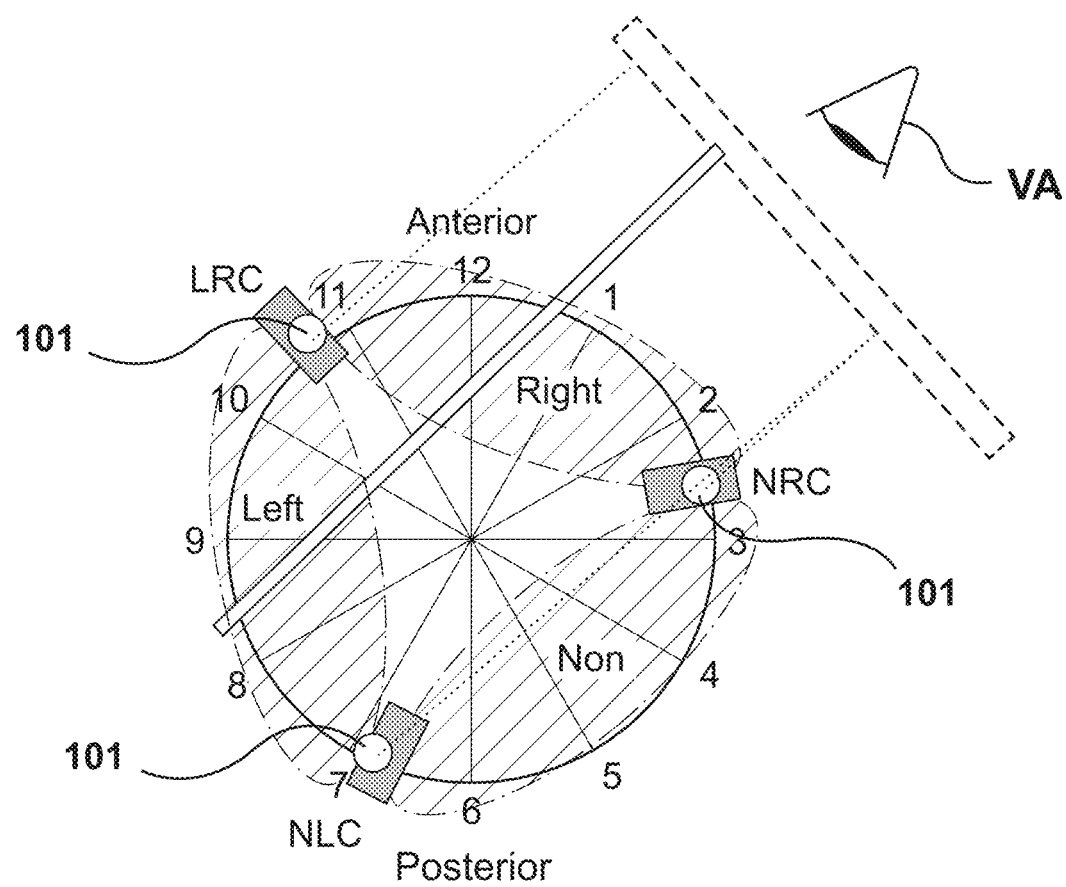
FIG. 10A depicts an illustration of the native aortic valve as viewed from the aorta and including markers of a transcatheter heart valve prosthesis.
Figure 10B:
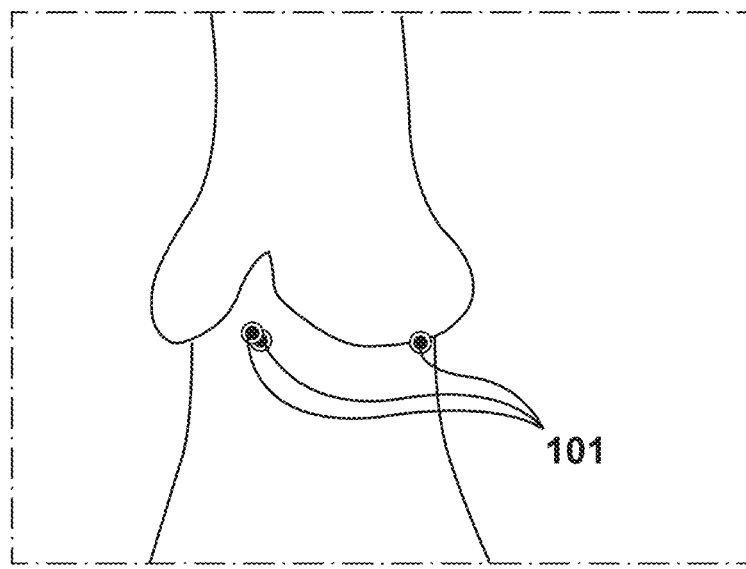
FIG. 10B illustrates a schematic representation of a fluoroscopic image of a native aortic valve using the cusp overlap view and showing markers of a transcatheter heart valve prosthesis disposed therein in a partially expanded configuration.
Figure 10C:
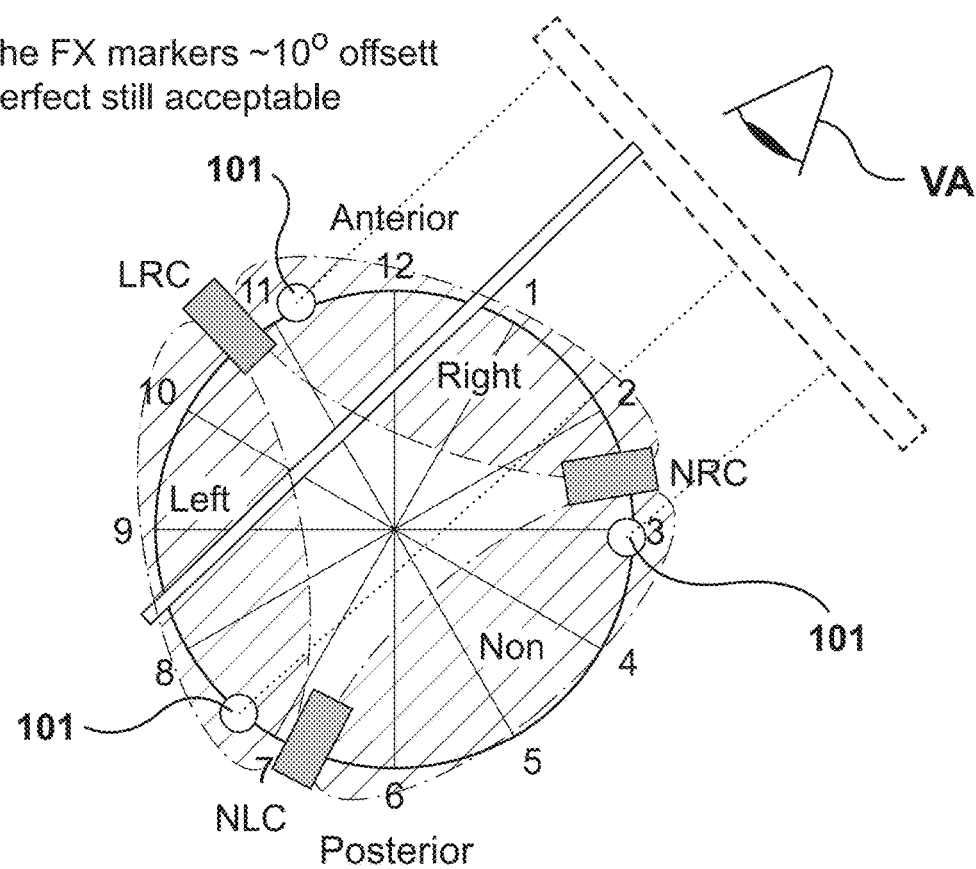
FIG. 10C depicts an illustration of the native aortic valve as viewed from the aorta and including markers of a transcatheter heart valve prosthesis.
Figure 10D:
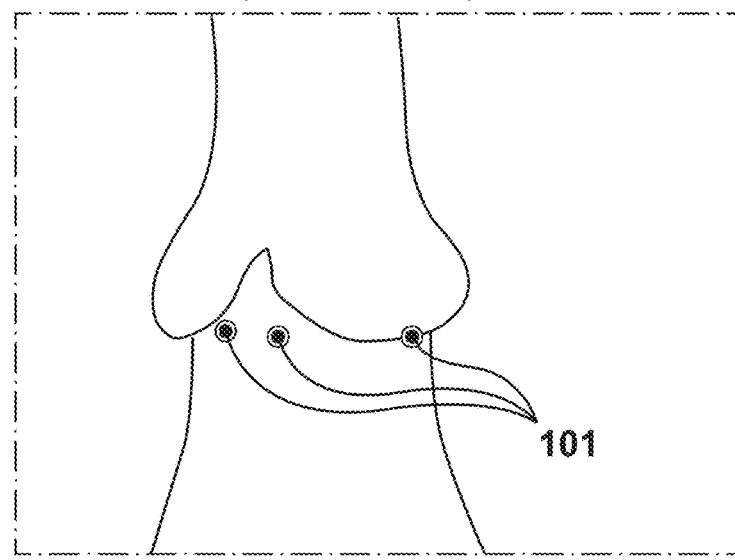
FIG. 10D illustrates a schematic representation of a fluoroscopic image of a native aortic valve using the cusp overlap view and showing markers of a transcatheter heart valve prosthesis disposed therein in a partially expanded configuration.
Figure 10E:
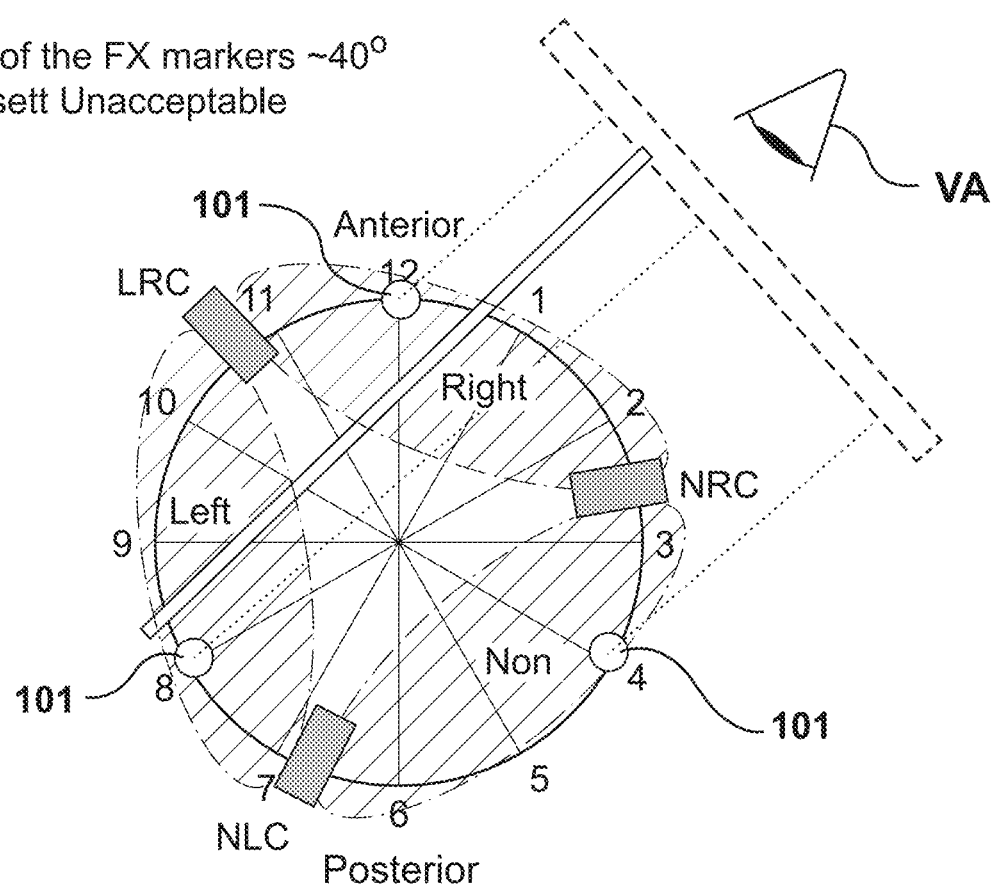
FIG. 10E depicts an illustration of the native aortic valve as viewed from the aorta and including markers of a transcatheter heart valve prosthesis.

Further, during the procedure, the cusp overlap view and marker(s) may be used to confirm that the transcatheter heart valve prosthesis is rotationally aligned such as to not cause coronary obstruction. As explained above, a pigtail catheter such as the pigtail catheter 820 is ordinarily placed in the basal portion of the non-coronary cusp NCC prior to the delivery system 800 being advanced to the native aortic valve. The delivery system 800 is advanced past the native valve leaflets/cusps until a marker on the delivery system, such as a marker located on a distal portion of the capsule 806, is aligned with the annulus of the native heart valve. The capsule 806 may then be retracted proximally to expose the inflow end 112 of the transcatheter heart valve prosthesis 100, enabling the inflow end 112 of the transcatheter heart valve prosthesis 100 to self-expand. With the imaging system in the cusp overlap view, as shown in FIG. 10B, two of the markers 101 of the transcatheter heart valve prosthesis 100 can be seen towards the left side of the annulus and one of the markers 101 can be seen towards the right side of the annulus. It is noted that left and right as used regarding FIG. 10B and other fluoroscopy illustrations is with respect to the fluoroscopy image/illustration, not anatomical left and right. Using the cusp overlap view and the markers 101 of the transcatheter heart valve prosthesis 100, a clinician can determine the commissures 109 of the prosthetic leaflets 106 are generally aligned with the idealized native commissures when two of the markers 101 towards the left side of the annulus (i.e., towards the pigtail catheter 820) as viewed in the fluoroscopy image are substantially aligned. As used herein with respect to the cusp overlap view system and method, the term "substantially aligned" means that the left side markers 101 are within one (1) cell of each other. Thus, for example, FIGS. 10C-10D should the left side markers 101 offset from each other by about 10°. This is within one cell and is therefore "substantially aligned" as defined herein.

Figure 10F:
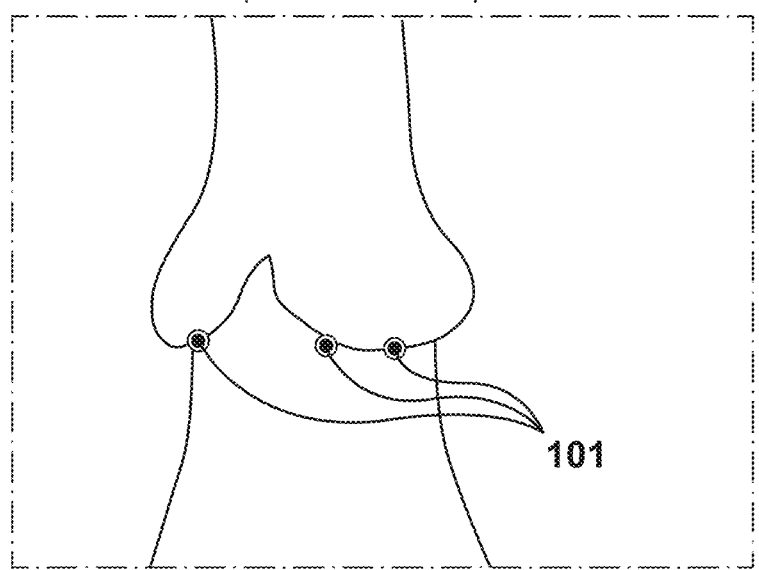
FIG. 10F illustrates a schematic representation of a fluoroscopic image of a native aortic valve using the cusp overlap view and including a transcatheter heart valve prosthesis disposed therein in a partially expanded configuration.
Figure 10G:
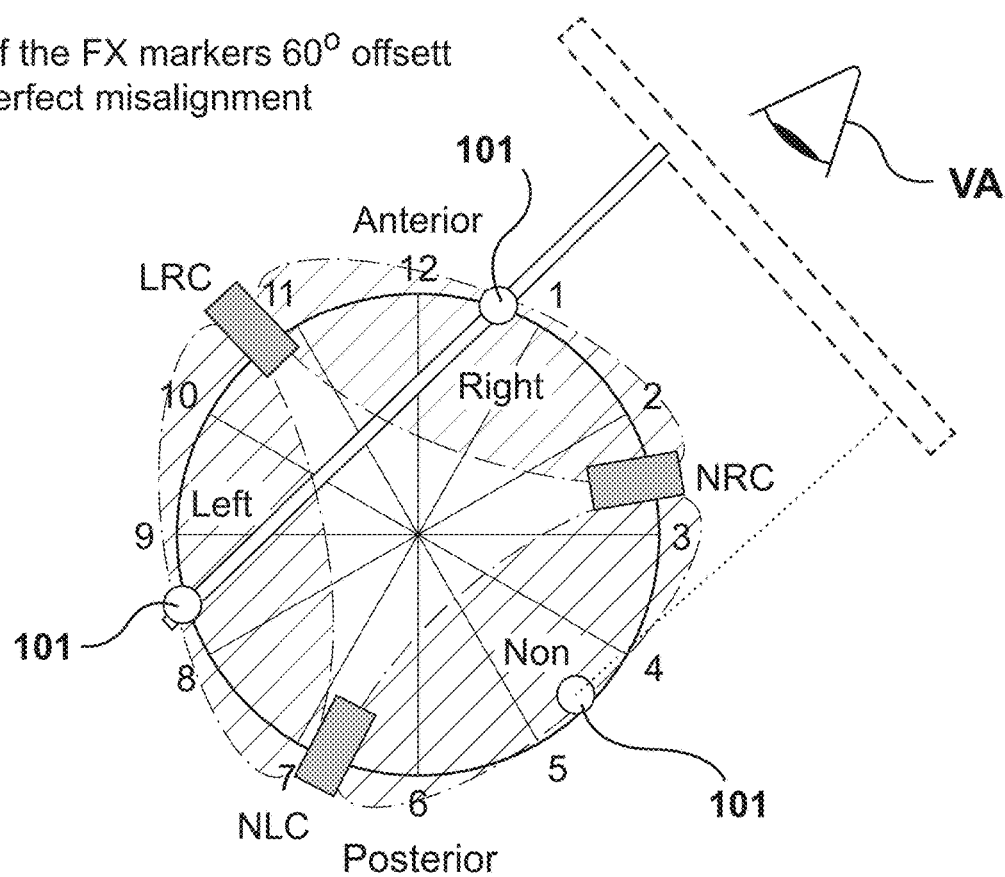
FIG. 10G depicts an illustration of the native aortic valve as viewed from the aorta and including markers of a transcatheter heart valve prosthesis.
Figure 10H:
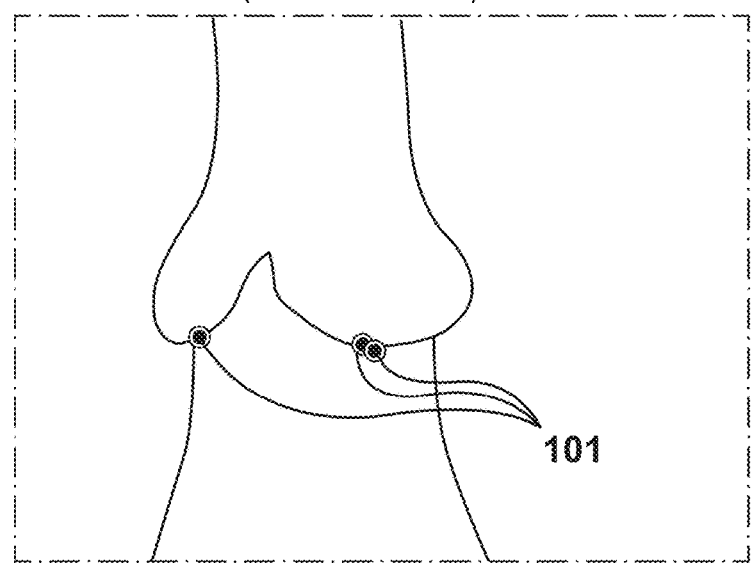
FIG. 10H illustrates a schematic representation of a fluoroscopic image of a native aortic valve using the cusp overlap view and including a transcatheter heart valve prosthesis disposed therein in a partially expanded configuration.

If the two left side markers 101 are not substantially aligned with each other, such as shown in FIGS. 10E-10F and 10G-10H, or there is only one left side marker, as shown in FIGS. 10G-10H, then the transcatheter heart valve prosthesis 100 may be rotated until there are two left side markers 101 substantially aligned with each other in the cusp overlap view. In some instances, the orientation shown in FIG. 10F with two markers 101 on the right side but offset from each other may be acceptable. Therefore, rather than rotating the transcatheter heart valve prosthesis 100, it may be desirable to first determine whether the center marker 101 in FIG. 10F is anterior or posterior. If the center marker 101 is posterior, then the result is acceptable. If the center marker 101 in FIG. 10F is anterior, then the result is not acceptable and the transcatheter heart valve prosthesis 100 may be rotated. To determine whether the center marker 101 is anterior or posterior, it may be desirable to move to the co-planar viewing, as known to those skilled in the art. If the transcatheter heart valve prosthesis 100 needs to be rotated, it may be rotated by rotating a handle of the delivery system, such as the handle 802 of the delivery system 800. Non-limiting examples of delivery systems that can be rotated at the handle to rotate a distal end of the delivery system are shown and described in U.S. provisional patent application No. 63/129,194, filed Dec. 22, 2020, the contents of which are incorporated by reference herein in their entirety.

When rotating the handle 802 to rotate the heart valve prosthesis 100, it may be convenient for the clinician to know in which direction (i.e., clockwise or counterclockwise) and how far to rotate the handle 802. Because fluoroscopic images are two-dimensional, it is not possible just from the image to determine in which direction to rotate the handle 802 in order to have the left markers 101 overlap. Therefore, the cusp overlap view and movement of the C-arm of the fluoroscopic imaging system may be used to determine which of the left markers 101 is anterior (i.e. closer in direction of the viewing angle) and which of the left markers is posterior (i.e. farther in the direction of the viewing angle).

Figure 11A:
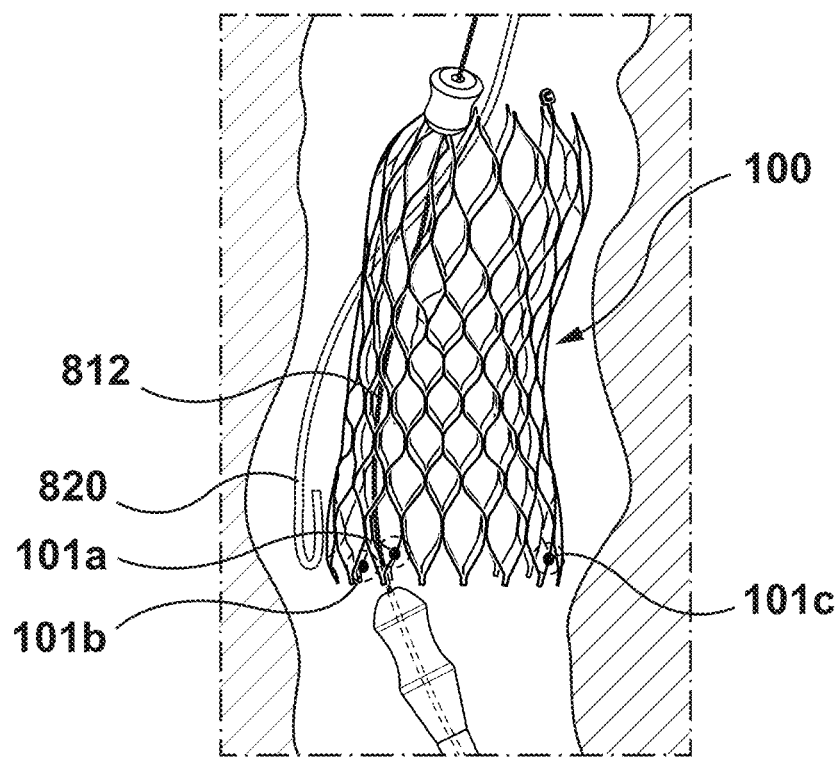
FIG. 11A illustrates an example fluoroscopic image of a native aortic valve using the cusp overlap view and including a transcatheter heart valve prosthesis disposed therein in a partially expanded configuration.
Figure 11B:
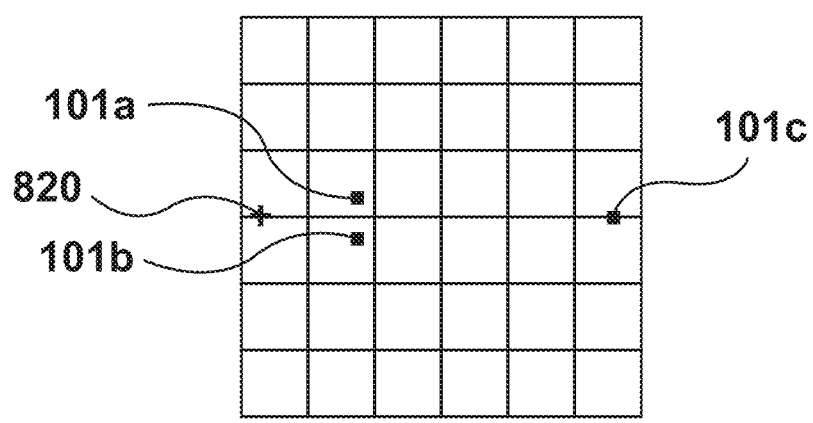
FIG. 11B illustrates schematically the location of the markers of the transcatheter heart valve prosthesis and the pigtail catheter as shown in FIG. 11A.
Figure 11C:
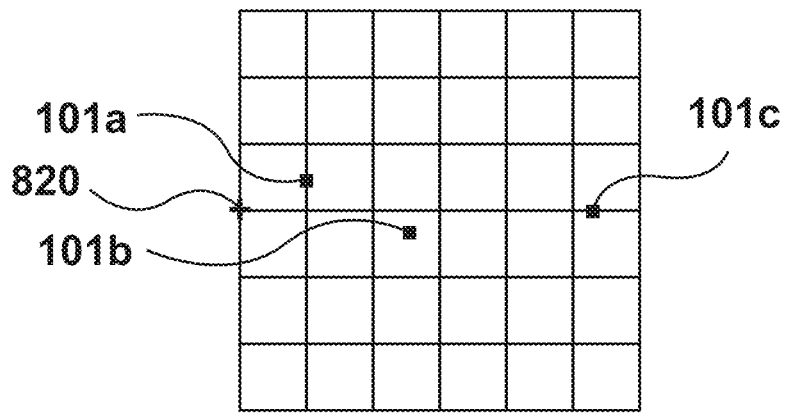
FIGS. 11C-11D show schematically movement of the markers of the transcatheter heart valve prosthesis of FIG. 11B as the viewing angle of the C-arm of a fluoroscopic imaging system is moved.
Figure 11D:
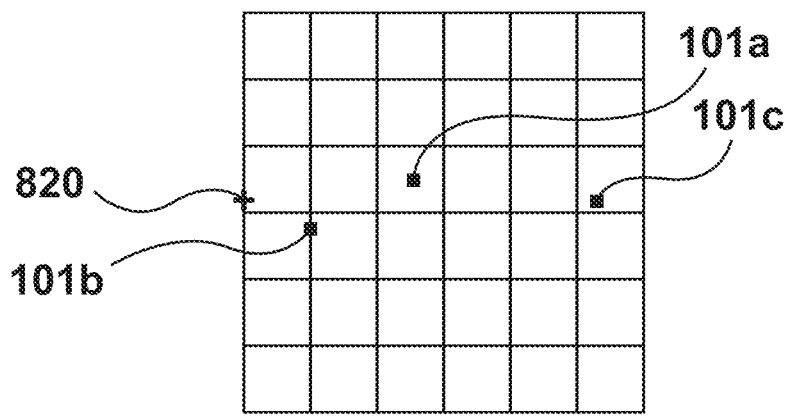

FIGS. 11A-11D show an embodiment of methods for determining which marker 101 is anterior and which is posterior. Although FIGS. 11A and 11B show the left markers 101 substantially aligned, the movement represented by FIGS. 11C and 11D applies equally to non-substantially aligned markers for determining the anterior and posterior markers. In FIGS. 11A-11D, the markers 101 are labelled as markers 101a, 101b, and 101c so as to distinguish between the markers 101. As can be seen, FIGS. 11B-11D are schematic representations of the markers 101 and the pigtail catheter 820 shown in FIG. 11A. In particular, FIG. 11B schematically represents the markers 101 as shown in FIG. 11A, with the left two markers 101a, 101b substantially aligned and the right marker 101c separated from the left markers 101. FIG. 11C shows that if the C-arm of the fluoroscopic imaging system is swung 20° towards the left anterior oblique (LAO) viewing angle, the anterior marker 101a moves to the left, i.e., towards the pigtail catheter 820, and the posterior marker 101b moves towards the right, i.e., away from the pigtail catheter 820. Similarly, FIG. 11D shows that if the C-arm of the fluoroscopic imaging system is swung 20° towards the right anterior oblique (RAO) view angle, the anterior marker 101a moves to the right, i.e., away from the pigtail catheter 820, and the posterior marker 101b moves towards the left, i.e., towards the pigtail catheter 820.

Figure 12:
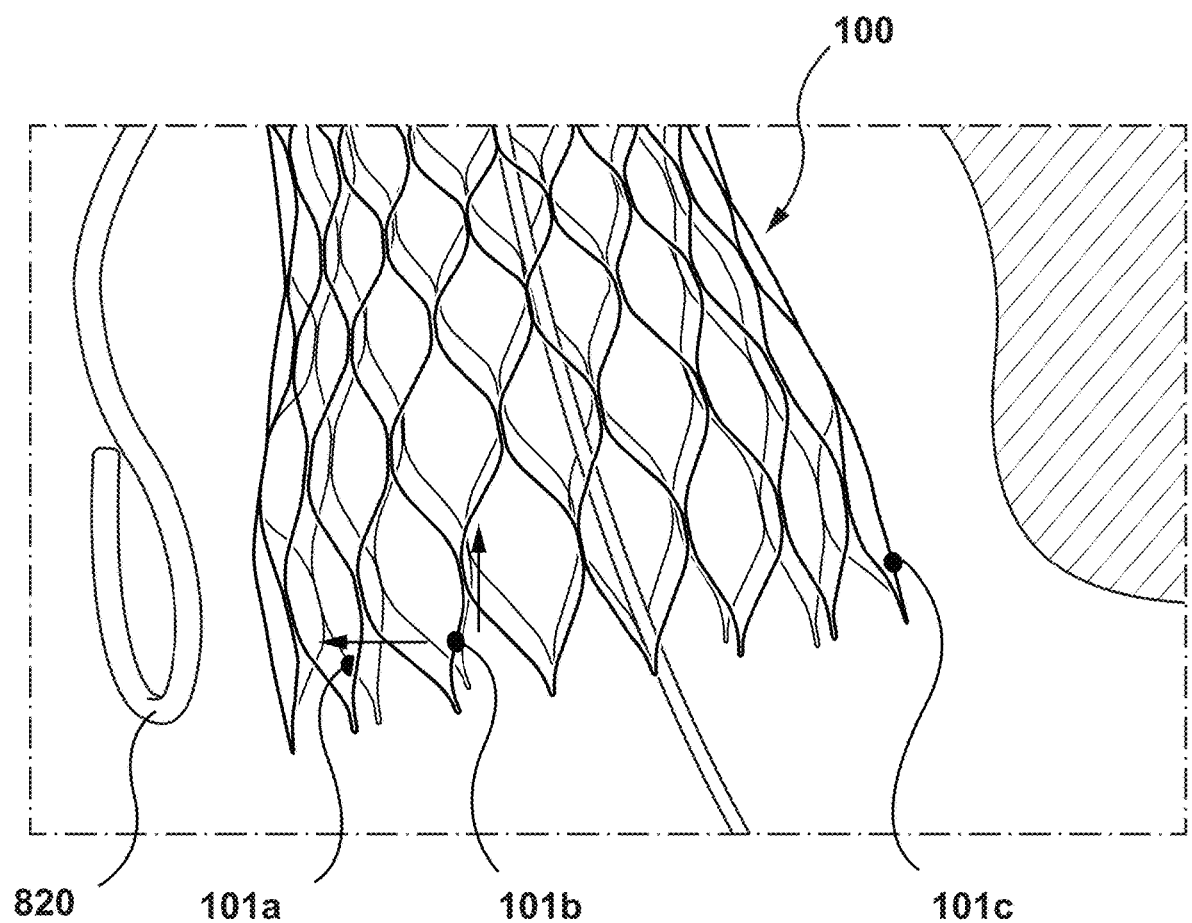
FIG. 12 depicts an illustration of a fluoroscopic image in a cusp overlap view with a transcatheter heart valve prosthesis in a native aortic valve with markers thereof not substantially aligned.

FIG. 12 shows a cusp overlap view with two left markers 101a, 101b that are not substantially aligned. As noted in FIG. 12, and described above with respected to FIG. 11B, if the C-arm of the fluoroscopic imaging system is moved from the cusp overlap viewing angle to the LAO viewing angle, the anterior marker 101 moves to the left, i.e., towards the pigtail catheter 820. Another method of determining the anterior marker is to move the C-arm of the fluoroscopic imaging system from the cusp overlap viewing angle to the caudal viewing angle, the anterior marker moves upwards, as represented by the arrow in FIG. 12.

Using any of the methods described above to determine which marker 101 of the markers 101 on the left side of the inner shaft 812 in the cusp overlap view is the anterior marker, this information can be used to determine in which direction to rotate the handle 802 in order to substantially align the left markers 101. In particular, the markers 101 have been labelled 101a, 101b, and 101c in FIG. 12 to establish a baseline location of the markers. Thus, in FIG. 12, as described above with respect to FIGS. 11A-11D, the markers 101a and 102b are the markers to the left of the inner shaft 812, and the marker 101c is to the right of the inner shaft 812. As explained above, it is desirable for the markers 101a and 101b to be substantially aligned, but in FIG. 12 they are not substantially aligned. Also, it is understood that the examples given herein are for femoral access, with the delivery system 800 extending over the aortic arch and then down to the aortic valve. The systems and methods described herein can be used with other routes to the aortic valve (or other heart valves), but adjustments in directions may be needed.

Accordingly, referring back to FIG. 12, if the marker 101b is determined to be the anterior marker, the clinician can rotate the handle 802 clockwise to improve alignment, i.e., move the markers 101a and 101b closer to being substantially aligned. Similarly, if it is determined that the marker 101a is the anterior marker, the clinician can rotate the handle 802 counterclockwise to improve alignment, i.e., move the markers 101a and 101b closer to being substantially aligned.

Further, the cusp overlap view shown in FIG. 12 can be used to determine how much rotation is required to move the markers 101a and 101b into substantial alignment. In the example shown in FIG. 12, the markers 101a and 101b are separated by two cells of the transcatheter heart valve prosthesis 100. Because transcatheter heart valve prosthesis 100 has 15 cells around the circumference thereof, each cell occupies approximately 24 degrees of the circumference of the transcatheter heart valve prosthesis 100. Therefore, because the markers 101a, 101b are two cells apart, rotating the heart valve prosthesis 100 48 degrees in the proper direction, depending on which marker 101a, 101b is the anterior marker, should bring the markers 101a, 101b into substantial alignment. Therefore, a clinician can use an identifier on the handle 802, such as the flush port, and estimate 48 degrees rotation of the handle. For example, and not by way of limitation, if the flush port is located at 3 o'clock on the handle 802, and the marker 101b is the anterior marker, the clinician can move the handle 802 such that the flush port is at approximately 5:30. Alternatively, or additionally, the clinician may view the marker 816 on the capsule 806 to see when it has rotated the appropriate amount, e.g. 48 degrees in the example given above. Further, the alignment may be checked again after rotation of the handle 802 to ensure that the markers 101*a*, 101*b* are substantially aligned.

As known to those skilled in the art, rotation of the handle 802 of the delivery system 802 does not always mean an equal rotation at the distal end of the delivery system and the transcatheter heart valve prosthesis. Therefore, the markers 101 of the transcatheter heart valve prosthesis 100 can be monitored using the imaging system in the cusp overlap view until the two left side markers 101 are substantially aligned. Further, the transcatheter heart valve prosthesis 100 need not be recaptured within the capsule 806 of the delivery system 800 prior to rotation thereof, although it may be recaptured.

As noted above, one of the purposes of the markers, systems, and methods described above is to ensure that the coronary arteries are not blocked by the commissures and/or leaflets of the transcatheter heart valve prosthesis. In the embodiments described above, the markers 101 are axially aligned with the commissures 109 of the valve structure 104. Further, in the embodiments described above, the goal is to align the markers 101, and hence the commissures 109 of the prosthetic valve structure 104, with the native commissures. However, as also noted above, the native valve commissures are rarely 120 degrees apart, while the prosthetic valve commissures 109 are 120 degrees apart. Therefore, it is not likely that the all of the prosthetic valve commissures (e.g. three prosthetic valve commissures) can be aligned with the native valve commissures. Further, while the location of the native cusps/commissures provides a general idea of the location of the native coronary artery ostia, native anatomies may vary. Therefore, while the cusp overlap view provides confidence that if the markers 101 of the transcatheter heart valve prosthesis are in certain locations, the coronaries will not be blocked by the prosthetic valve structure, as described above, other embodiments may be preferable in certain circumstances. In another embodiment hereof, described below, a coronary overlap viewing angle is used with the transcatheter heart valve prosthesis 100 including the markers 101 described above.

Figure 16A:
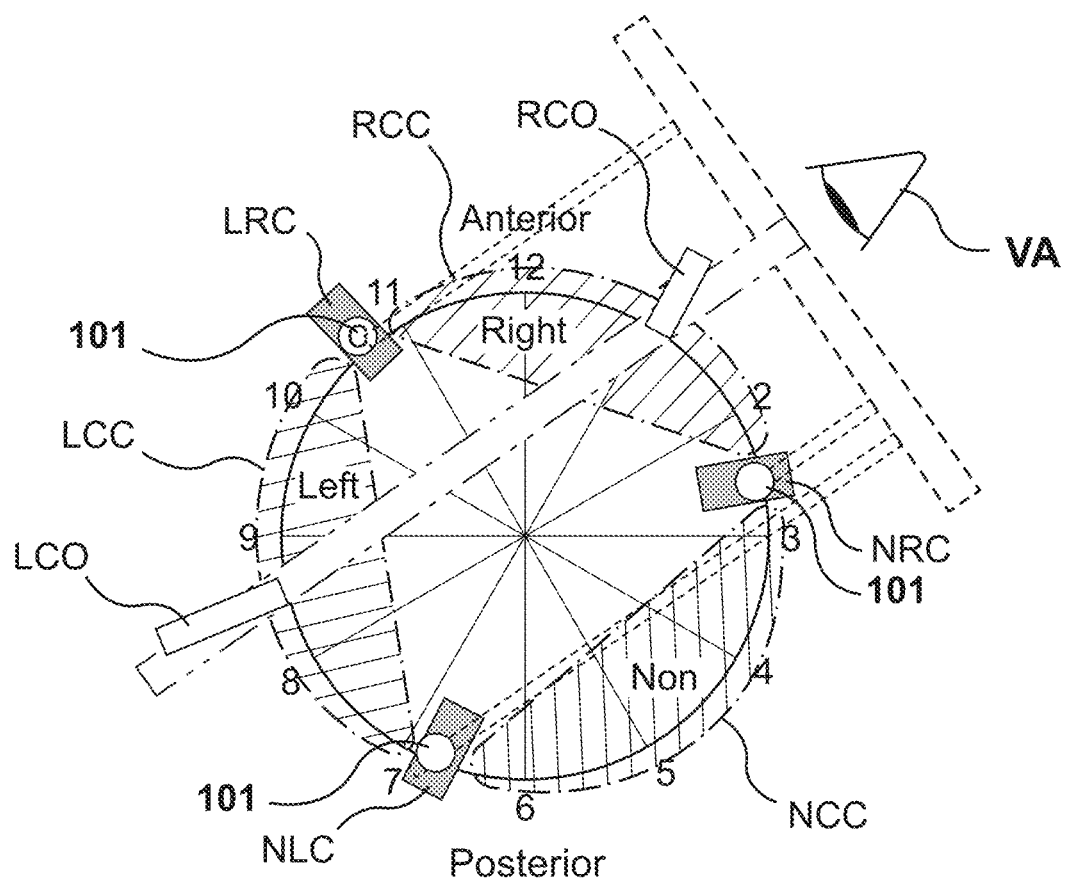
FIGS. 16A-16B depict an illustration of the native aortic valve as viewed from the aorta and including markers of a transcatheter heart valve prosthesis, and a schematic representation of a fluoroscopic image of a native aortic valve using the coronary overlap view.

Accordingly, as described above, imaging systems such as fluoroscopic imaging systems used during transcatheter aortic valve replacement procedures generally include a C-arm gantry that enables different viewing angles of the native aortic valve. One particular viewing angle is a "cusp overlap view" is described above with respect to FIGS. 9A-9B and 10A-10B. Another viewing angle is referred to herein as the "coronary overlap view". In the coronary overlap view, during the pre-procedure CT work-up, the location of the coronary ostia (i.e., the openings of the coronary arteries into the sinus of the native aortic valve) are located. Using these locations, it can be determined the proper angle of the C-arm of the imaging system such that the coronary ostia overlap. For example, FIG. 16A shows an example idealized native aortic valve (e.g. the native commissures are 120 degrees apart), with the location of the left coronary ostia LCO and right coronary ostia RCO marked. As shown in FIG. 16A, the viewing angle VA of the imaging system is selected such that the right coronary ostia RCO and the left coronary ostia LCO overlap each other. Similarly, FIGS. 17A, 18A, 19A, 20A, 21A, and 22A show an idealized native aortic valve with the native commissures spaced at 120° around the circumference of the native aortic valve sinus. As noted above, patient anatomies vary from this idealized representation. FIGS. 16B, 17B, 18B, 19B, 20B, 21B, and 22B show a schematic representation of a fluoroscopic image with the viewing angle set for the coronary overlap view. It is noted that the coronary arteries are not shown in the fluoroscopic image, but by using the coronary overlap view, it is known where the coronary ostia are located and because the coronary ostia are aligned in the view, they are commonly located in the 2-Dimensional view of the fluoroscopic image (i.e., one is behind the other). Therefore, knowing the location of the coronary ostia, a clinician can check the location of the commissures 109 of the valve structure 104 of the transcatheter heart valve prosthesis to ensure that none of the prosthetic commissures 109 are aligned or in near alignment with the coronary ostia.

With the above understanding of the coronary overlap view and the markers 101 in the transcatheter heart valve prosthesis 100 described above, a system and method of rotationally aligning the transcatheter heart valve prosthesis 100 will now be described. As known to those skilled in the art, the transcatheter heart valve prosthesis 100 may be delivered percutaneously via femoral access. In particular, in the example of a self-expanding transcatheter heart valve prosthesis, e.g. the transcatheter heart valve prosthesis 100, the prosthesis is constrained in a radially compressed configuration by, for example, the capsule 806 of the delivery system 800. As described above, characteristics of a patient's native anatomy may be determined prior to starting the procedure, such as by a CT scan. In particular, the coronary ostia may be located using a CT scan. Using this planning CT, a determination may be made prior to the procedure regarding orientation of the delivery system, and hence the transcatheter heart valve prosthesis, when delivering the transcatheter heart valve prosthesis. For example, and not by way of limitation, the delivery system 800 is arranged such that the flush port 816 is aligned with the C-paddle 150 of the transcatheter heart valve prosthesis 100, which is aligned with one of the commissures 109 of the valve structure 104. As explained in Tang, orienting the flush port 816 at 3 o'clock may reduce coronary artery overlap. However, using pre-procedure CT, the orientation of a feature of the delivery system, such as the flush portion 816, that has a known relationship to a feature of the transcatheter heart valve prosthesis, such as one of the commissures 109 of the transcatheter heart valve prosthesis 100, may be further defined by the specific patient anatomy. Thus, using pre-procedure planning, a prediction can be made regarding a preferred orientation of the delivery system, such as the delivery system 800, to reduce coronary artery ostia overlap.

Further, during the procedure, the coronary overlap view and marker(s) may be used to confirm that the transcatheter heart valve prosthesis is rotationally aligned such as to not cause coronary obstruction. As explained above, the delivery system 800 is advanced past the native valve leaflets/cusps until a marker on the delivery system, such as a marker located on a distal portion of the capsule 806, is aligned with the annulus of the native heart valve. The capsule 806 may then be retracted proximally to expose the inflow end 112 of the transcatheter heart valve prosthesis 100, enabling the inflow end 112 of the transcatheter heart valve prosthesis 100 to self-expand.

Figure 16B:
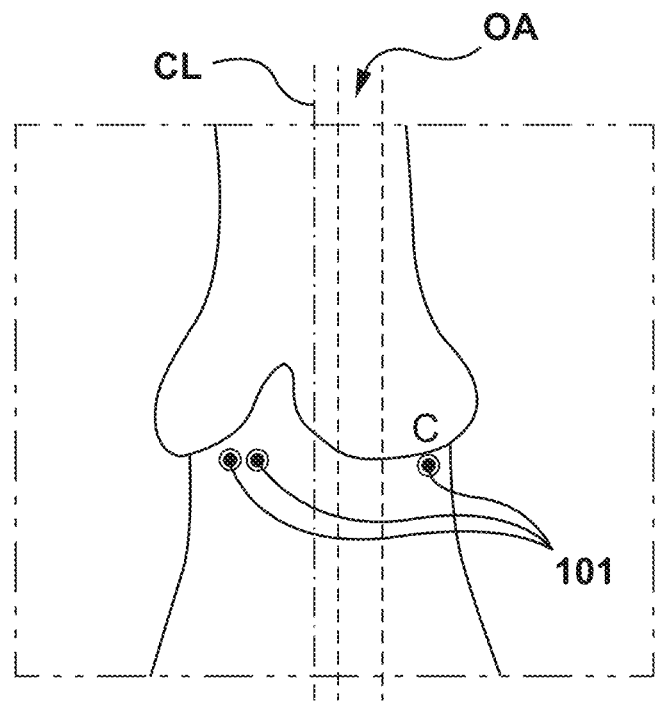

With the imaging system in the coronary overlap view, and the markers 101 aligned with the prosthetic commissures 109 aligned with the idealized native commissures LRC, NLC, NRC, as shown in FIG. 16A, two of the markers 101 of the transcatheter heart valve prosthesis 100 can be seen left of the center-line CL of the image and one of the markers 101 can be seen right of the center-line CL of the image, as shown in FIG. 16B. FIG. 16B also shows an overlap area OA where the coronary artery ostia are located. As explained above, this overlap area OA is not shown on the fluoroscopic image, but is known the clinician and has been added to the schematic fluoroscopic image herein for clarity of explanation. Thus, as can be seen in FIG. 16B, none of the prosthetic valve commissures 109 overlap within the overlap area OA. Thus, the ostia of the coronary arteries will not be blocked. Similar to the cusp overlap view, it is noted generally that having two of the markers 101 to the left side of the fluoroscopic image will generally results in no interference with the coronary arteries. It is noted that left and right as used regarding FIG. 16B and other fluoroscopy illustrations is with respect to the fluoroscopy image/illustration, not anatomical left and right.

FIGS. 16C and 16D show a comparison between the cusp overlap view and the coronary overlap view for an idealized native anatomy with the native commissures 120 degrees apart and the markers 101 located at the native commissures. FIGS. 16C and 16D also show the fluoroscopy image projected onto the view from the aorta. As in the other drawings described herein, the left and right coronary arteries shown in the illustrated fluoroscopic image are for reference only, and would not be shown in an actual fluoroscopic image. As shown in comparing FIGS. 16C and 16D, with the left and right coronary arteries located in the particular positions shown, the views are similar. As shown in FIG. 16D, however, the ostia of the left and right coronary arteries are aligned in the coronary overlap view, as further described herein.

Figure 17A:
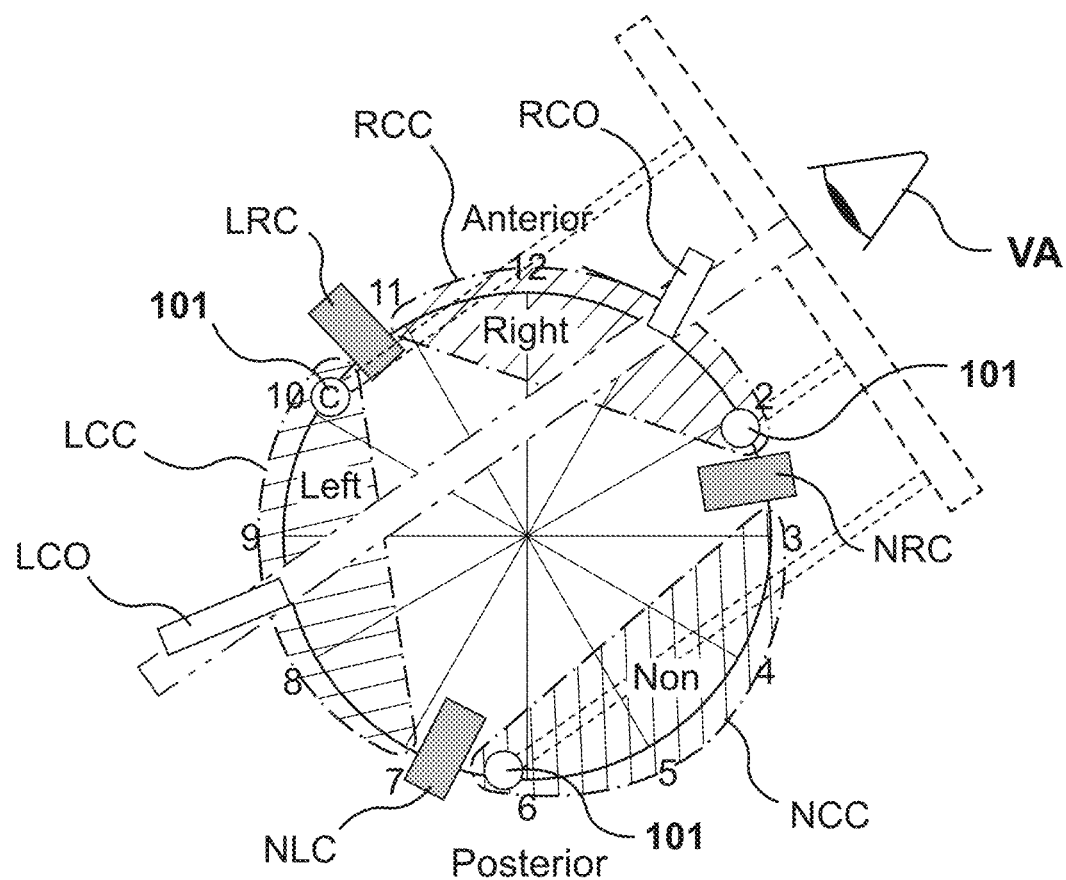
FIGS. 17A-17B depict an illustration of the native aortic valve as viewed from the aorta and including markers of a transcatheter heart valve prosthesis, and a schematic representation of a fluoroscopic image of a native aortic valve using the coronary overlap view.
Figure 17B:
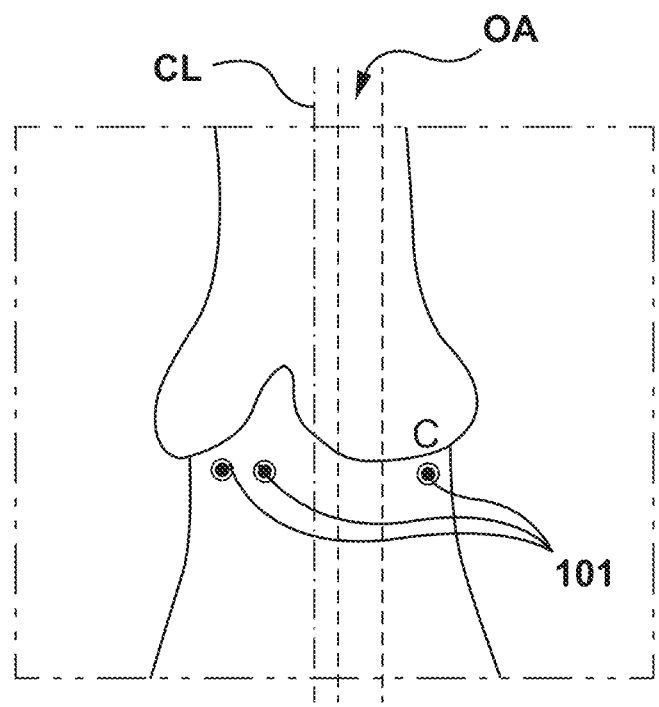

FIGS. 17A-17B provide another example of the transcatheter heart valve prosthesis 100 delivered and partially deployed at a native heart valve prosthesis. In this example, as can be seen in FIG. 17A, the markers 101 (and hence the prosthetic valve commissures 109) are rotated 15 degrees counterclockwise relative to the idealized native valve commissures LRC, NLC, NRC. As shown in the coronary overlap view fluoroscopic image of FIG. 17B, two of the markers 101 are still to the left of the center-line CL of the image. Further, none of the markers 101 are located in the overlap area OA. Thus, a clinician seeing the image of FIG. 17B can be confident that the coronary artery ostia are not blocked, and can proceed to fully deploy the transcatheter heart valve prosthesis 100.

Figure 18A:
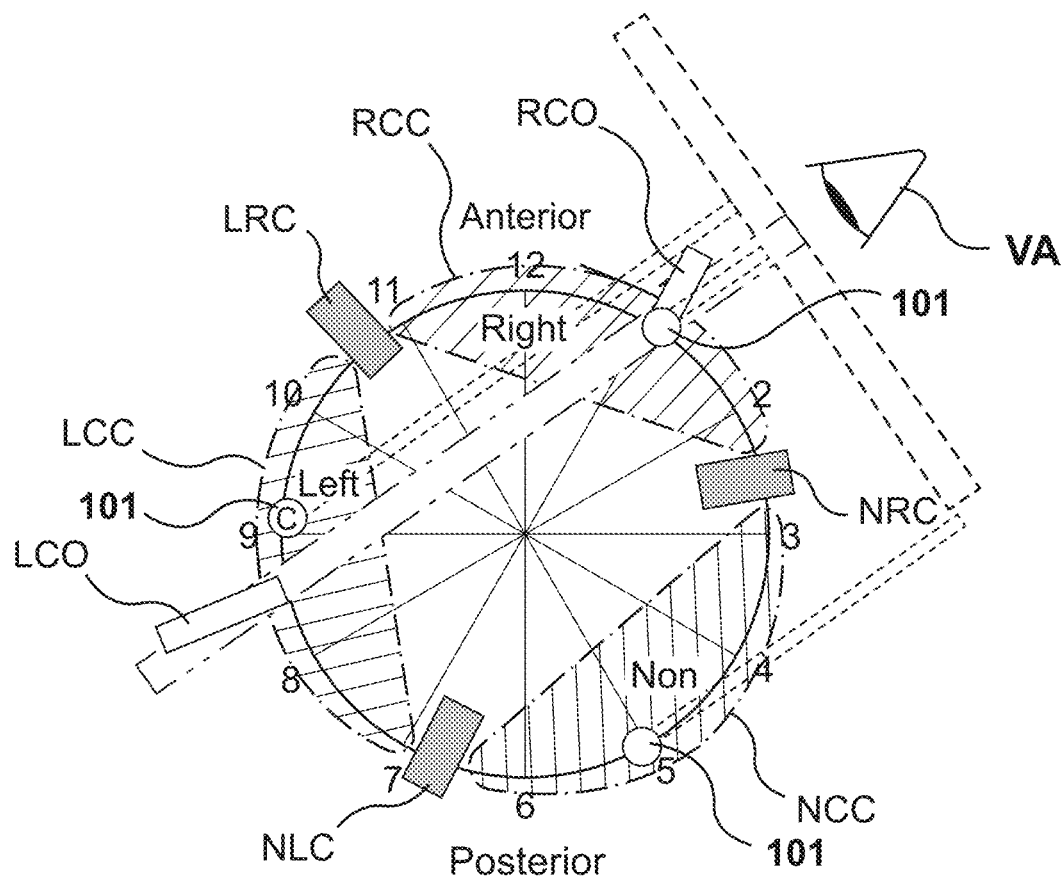
FIGS. 18A-18B depict an illustration of the native aortic valve as viewed from the aorta and including markers of a transcatheter heart valve prosthesis, and a schematic representation of a fluoroscopic image of a native aortic valve using the coronary overlap view.
Figure 18B:
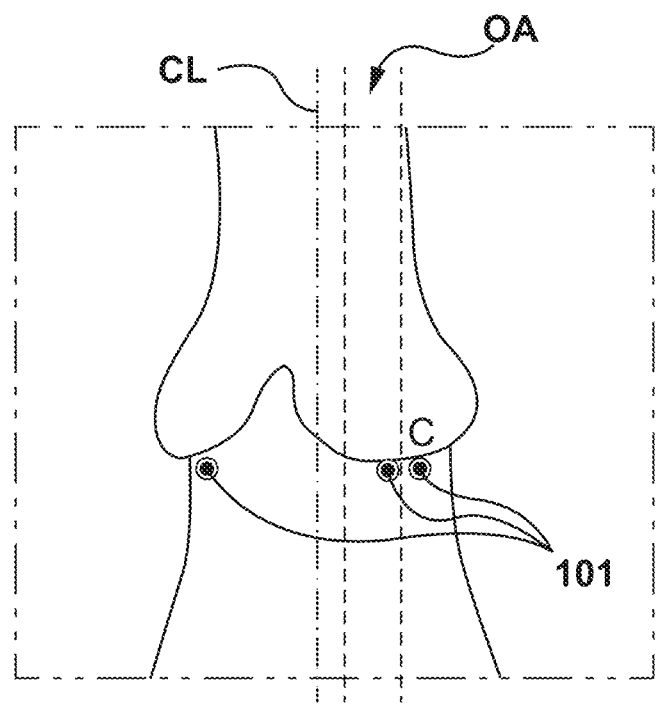

FIGS. 18A-18B provide another example of the transcatheter heart valve prosthesis 100 delivered and partially deployed at a native heart valve prosthesis. In this example, as can be seen in FIG. 18A, the markers 101 (and hence the prosthetic valve commissures 109) are rotated approximately 47 degrees counterclockwise relative to the idealized native valve commissures LRC, NLC, NRC. As shown in the coronary overlap view fluoroscopic image of FIG. 18B, two of the markers 101 are to the right of the center-line CL of the image. Further, one of the markers 101 is located in the overlap area OA. Thus, a clinician seeing the image of FIG. 18B can determine that at least one of the coronary ostia is likely blocked by the transcatheter heart valve prosthesis 100, and that the transcatheter heart valve prosthesis 100 should be rotated as described above before fully deploying the transcatheter heart valve prosthesis 100.

Figure 19A:
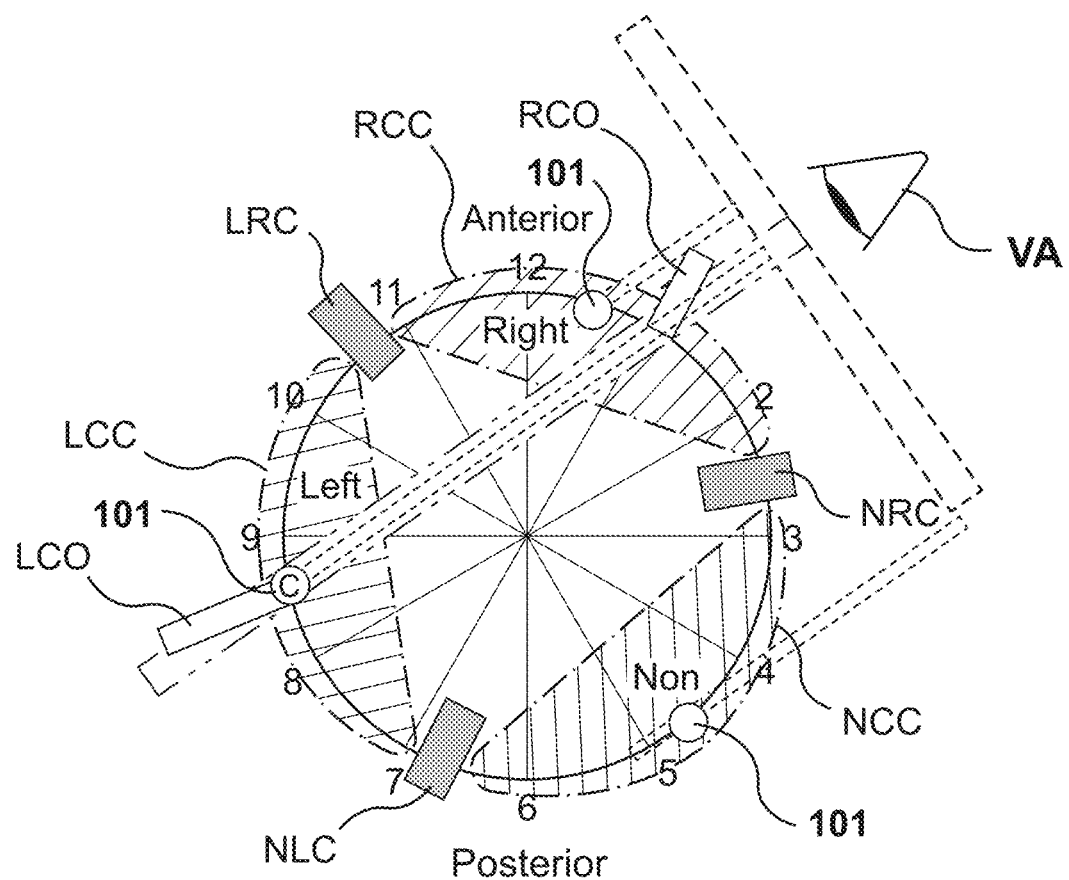
FIGS. 19A-19B depict an illustration of the native aortic valve as viewed from the aorta and including markers of a transcatheter heart valve prosthesis, and a schematic representation of a fluoroscopic image of a native aortic valve using the coronary overlap view.
Figure 19B:
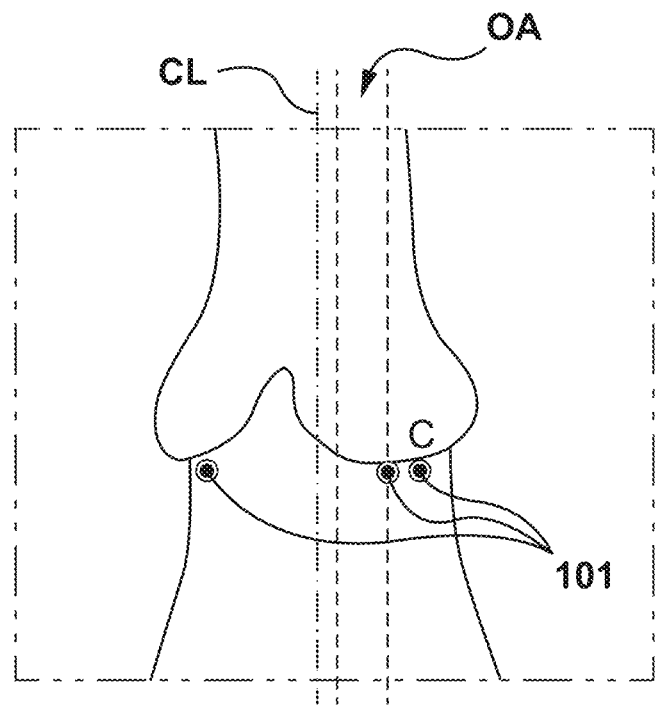

FIGS. 19A-19B provide another example of the transcatheter heart valve prosthesis 100 delivered and partially deployed at a native heart valve prosthesis. In this example, as can be seen in FIG. 19A, the markers 101 (and hence the prosthetic valve commissures 109) are rotated approximately 62 degrees counterclockwise relative to the idealized native valve commissures LRC, NLC, NRC. As shown in the coronary overlap view fluoroscopic image of FIG. 19B, two of the markers 101 are to the right of the center-line CL of the image. Further, one of the markers 101 is located in the overlap area OA. Thus, a clinician seeing the image of FIG. 19B can determine that at least one of the coronary ostia is likely blocked by the transcatheter heart valve prosthesis 100, and that the transcatheter heart valve prosthesis 100 should be rotated as described above before fully deploying the transcatheter heart valve prosthesis 100.

Figure 20A:
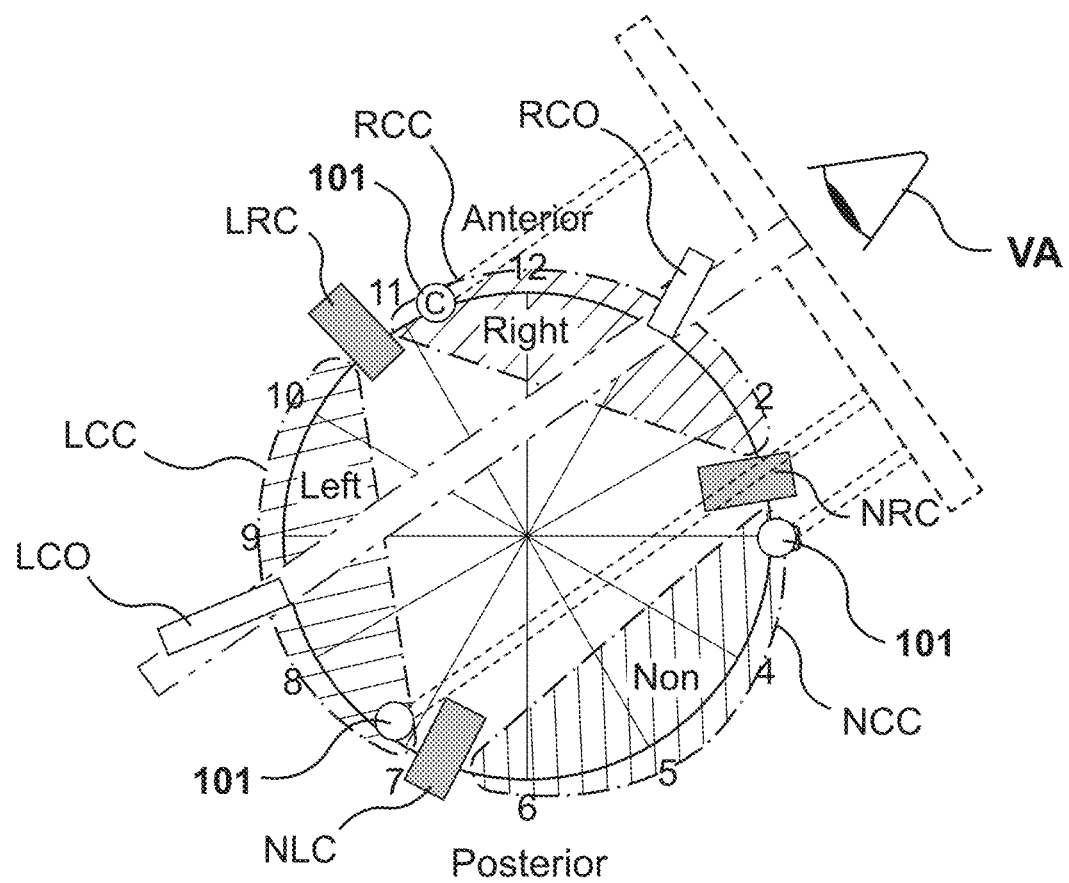
FIGS. 20A-20B depict an illustration of the native aortic valve as viewed from the aorta and including markers of a transcatheter heart valve prosthesis, and a schematic representation of a fluoroscopic image of a native aortic valve using the coronary overlap view.
Figure 20B:
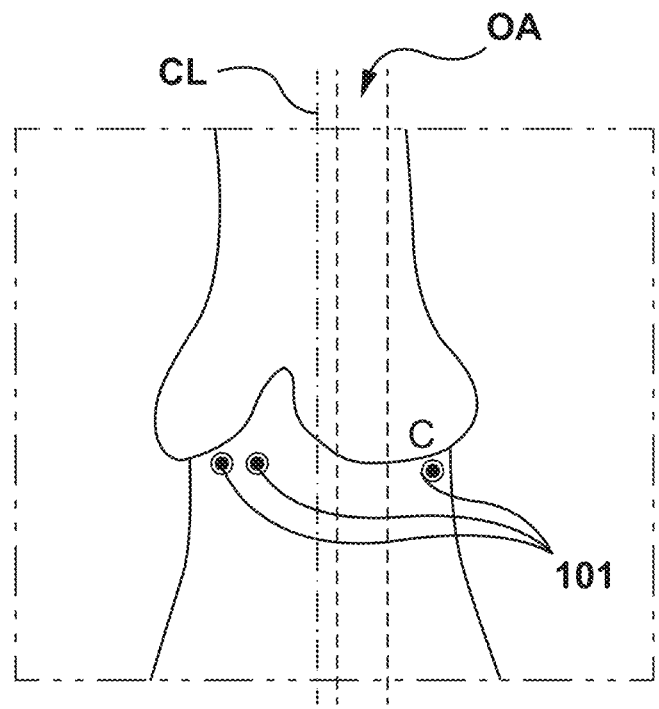

FIGS. 20A-20B provide another example of the transcatheter heart valve prosthesis 100 delivered and partially deployed at a native heart valve prosthesis. In this example, as can be seen in FIG. 20A, the markers 101 (and hence the prosthetic valve commissures 109) are rotated approximately 15 degrees clockwise relative to the idealized native valve commissures LRC, NLC, NRC. As shown in the coronary overlap view fluoroscopic image of FIG. 20B, two of the markers 101 are to the left of the center-line CL of the image. Further, none of the markers 101 are located in the overlap area OA. Thus, a clinician seeing the image of FIG. 20B can be confident that the coronary artery ostia are not blocked, and can proceed to fully deploy the transcatheter heart valve prosthesis 100.

Figure 21A:
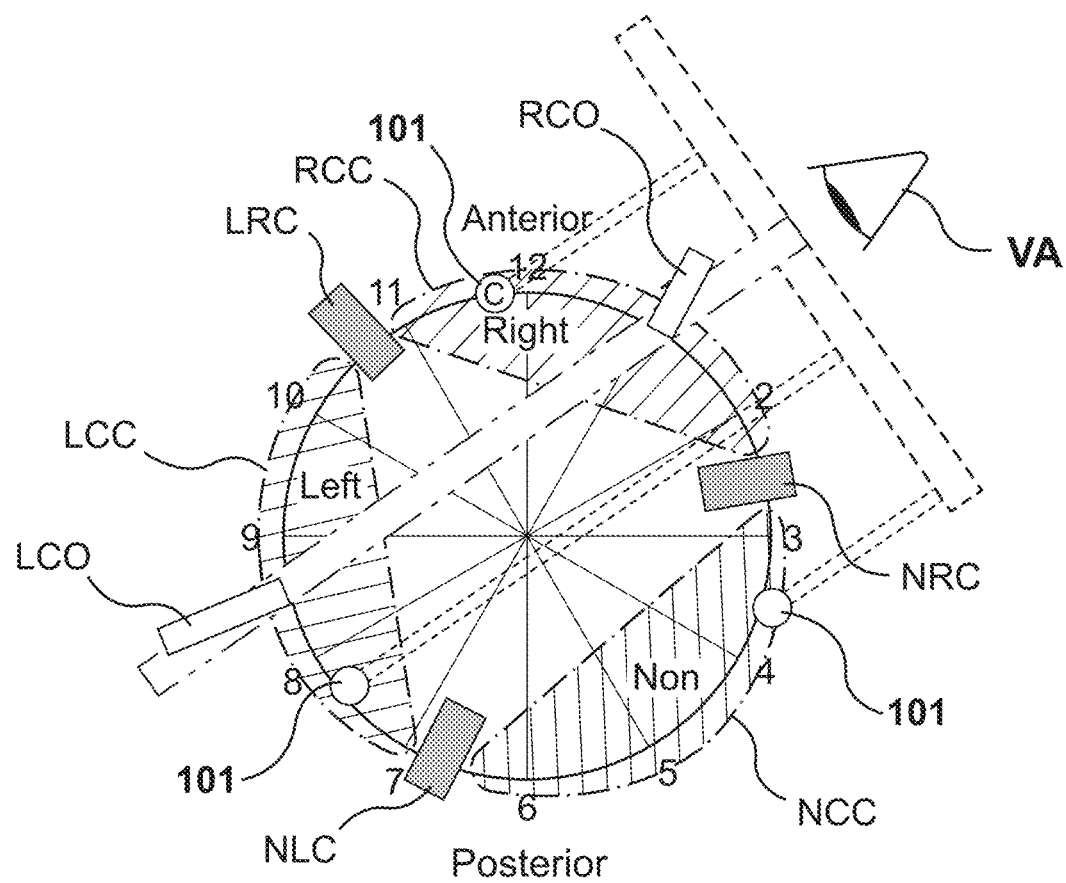
FIGS. 21A-21B depict an illustration of the native aortic valve as viewed from the aorta and including markers of a transcatheter heart valve prosthesis, and a schematic representation of a fluoroscopic image of a native aortic valve using the coronary overlap view.
Figure 21B:
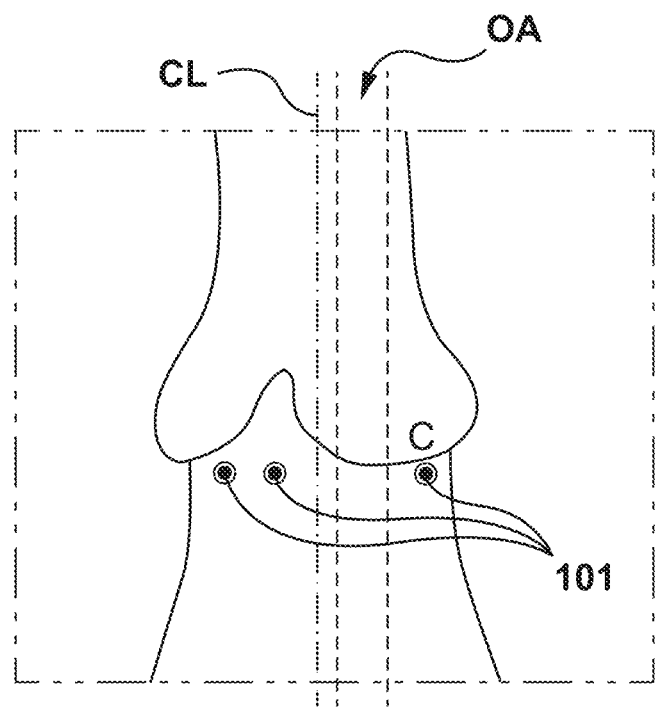

FIGS. 21A-21B provide another example of the transcatheter heart valve prosthesis 100 delivered and partially deployed at a native heart valve prosthesis. In this example, as can be seen in FIG. 21A, the markers 101 (and hence the prosthetic valve commissures 109) are rotated approximately 30 degrees clockwise relative to the idealized native valve commissures LRC, NLC, NRC. As shown in the coronary overlap view fluoroscopic image of FIG. 21B, two of the markers 101 are to the left of the center-line CL of the image. Further, none of the markers 101 are located in the overlap area OA. Thus, a clinician seeing the image of FIG. 21B can be confident that the coronary artery ostia are not blocked, and can proceed to fully deploy the transcatheter heart valve prosthesis 100.

Using the coronary overlap view, if the fluoroscopic image reveals that the coronary ostia may be blocked, then rotation of the transcatheter heart valve prosthesis 100 may proceed as described above with respect to FIGS. 11A-12.

Figure 22:
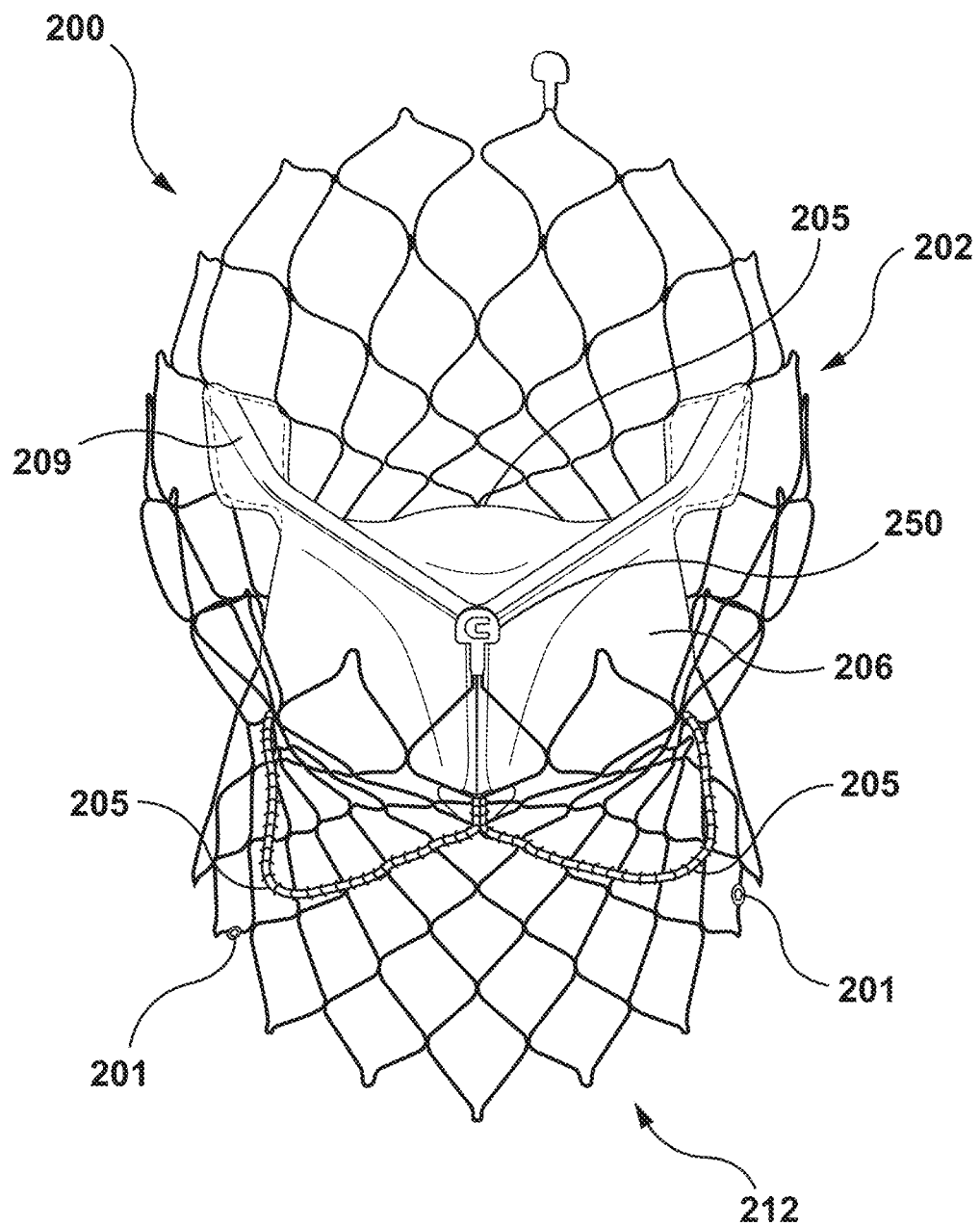
FIG. 22 depicts an illustration of a transcatheter heart valve prosthesis in accordance with embodiments hereof.

FIG. 22 shows another embodiment of a transcatheter heart valve prosthesis 200. The transcatheter heart valve prosthesis 200 is similar to the transcatheter heart valve prosthesis 100 described above, and similar reference numbers are used to indicate that same or similar features, so only differences will be described herein. In particular, the transcatheter heart valve prosthesis 200 includes a frame or stent 202 and a valve structure 204. The stent 202 can assume any of the forms described herein and variations thereof, as explained above, and is generally constructed so as to be expandable from the compressed configuration to the uncompressed, normal, or expanded configuration. The valve structure 204 is coupled to the stent 202 and provides two or more (typically three) leaflets 206, as described above. The heart valve prosthesis 200 further includes markers 201 substantially axially aligned with the nadirs 205 of the prosthetic heart valve leaflets 206. By "substantially axially aligned", it is meant that the markers 201 are disposed within one cell of a longitudinal axis that includes the nadir of one of the prosthetic valve leaflets 206. The "nadir" of a prosthetic valve leaflet is the lowest point of a prosthetic valve leaflets, and as used herein means the portion of the prosthetic valve leaflet 206 closest to the inflow end 212 of the transcatheter heart valve prosthesis 200. The "nadir" as used herein also means the approximate mid-point of the prosthetic valve leaflets 206 between the commissures 209 of the valve structure 204. Thus, in the embodiment shown, there are three markers 201, each one substantially axially aligned with a nadir 205 of one of the prosthetic heart valve leaflets 206. However, this is not meant to be limiting, and more or fewer markers 201 may be included. Further, the markers 201 may replace or be added to the markers 101 described above with respect to the transcatheter heart valve prosthesis 100. However, it is preferred that the markers 201 replace the markers 101 for clarity in the fluoroscopic images, as described in more detail below. Still further, although the markers 201 are shown at the first row of cells adjacent the inflow end 212 of the transcatheter heart valve prosthesis 200, this is not meant to be limiting, and the markers 201 may be located elsewhere longitudinally along the length of the transcatheter heart valve prosthesis 200.

The markers 201 are shown attached to the stent 202. The markers 201 can be attached to the stent 202 as described above, such as in containment members or otherwise attached to the stent 202. Further, instead of being attached to the stent 202, the markers 201 may be attached to an interior skirt or exterior skirt of the transcatheter heart valve prosthesis 200, or between such an in interior skirt and an exterior skirt, as described above with respect FIGS. 4B-4C.

Further details of the transcatheter heart valve prosthesis 200, the stent 202, the valve structure 204, and the markers 201 may be as described above with respect to the transcatheter heart valve prosthesis 100 and variations thereof as would be known to those skilled in the art.

Rotationally aligning the transcatheter heart valve prosthesis 200 will now be described with respect to FIGS. 23A-29B. As described above, imaging system such as fluoroscopic imaging systems used during transcatheter aortic valve replacement procedures generally include a C-arm gantry that enables different viewing angles of the native aortic valve. Particular viewing angles described above include the "cusp overlap view" and the "coronary overlap view".

Figure 23A:
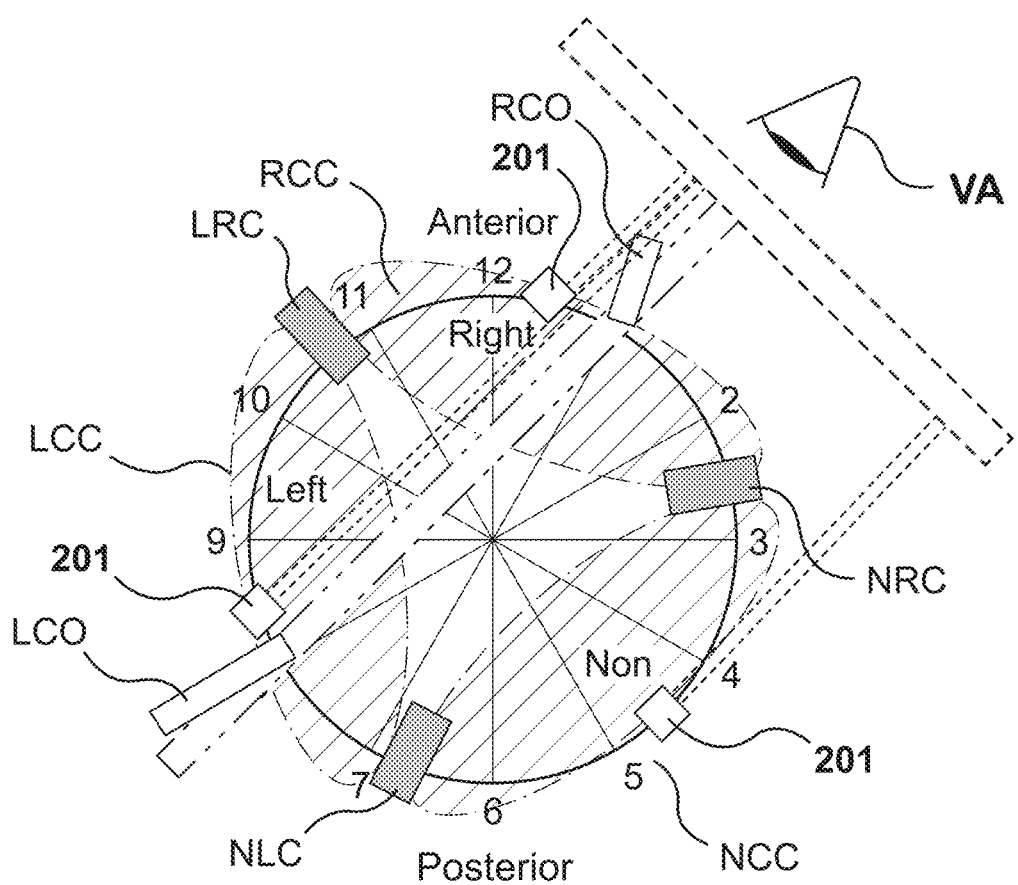
FIGS. 23A-23B depict an illustration of the native aortic valve as viewed from the aorta and including nadir markers of a transcatheter heart valve prosthesis, and a schematic representation of a fluoroscopic image of a native aortic valve using the coronary overlap view.
Figure 23B:
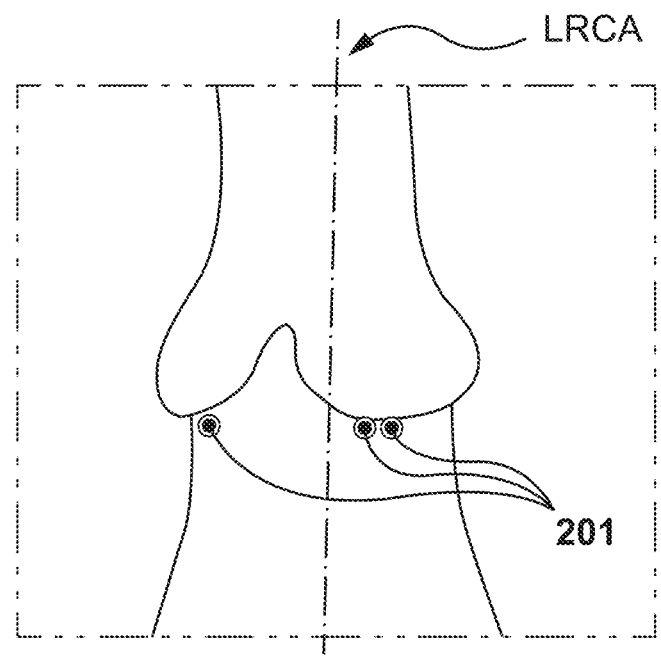

FIG. 23A shows a schematic illustration of a native aortic valve as seen from the aorta. As in the figures above, FIG. 23A shows the viewing angle VA, the left coronary cusp LCC, the right coronary cusp RCC, the non-coronary cusp NCC, the right coronary ostium RCO (and artery), the left coronary ostium LCO (and artery), the Left-right commissure LRC, the non-right commissure NRC, the non-left commissure NLC, and the markers 201. In FIG. 23A, the right coronary ostium RCO and the left coronary ostium LCO are each located 75° from the left-right commissure LRC in opposite circumferential directions. Thus, the viewing angle VA is both the coronary overlap viewing angle and the cusp overlap viewing angle described above. As can be seen in FIG. 23A, two of the markers 201 located at the nadirs of the prosthetic valve leaflets 206 are located adjacent the right coronary ostium RCO and the left coronary ostium LCO, respectively. FIG. 23B shows a schematic illustration of a fluoroscopic image of the arrangement shown in FIG. 23A, with the common longitudinal axis LRCA of the left coronary ostium LCO and the right coronary ostium RCO being shown. As can be seen in FIG. 23B, the nadir markers 201 nearest each of the coronary ostium are substantially aligned with each other. If two of the nadir markers 201 are substantially aligned with each other in the coronary/cusp overlap view, the right and left coronary ostia RCO, LCO are not blocked by the prosthetic valve commissures 209.

Figure 24A:
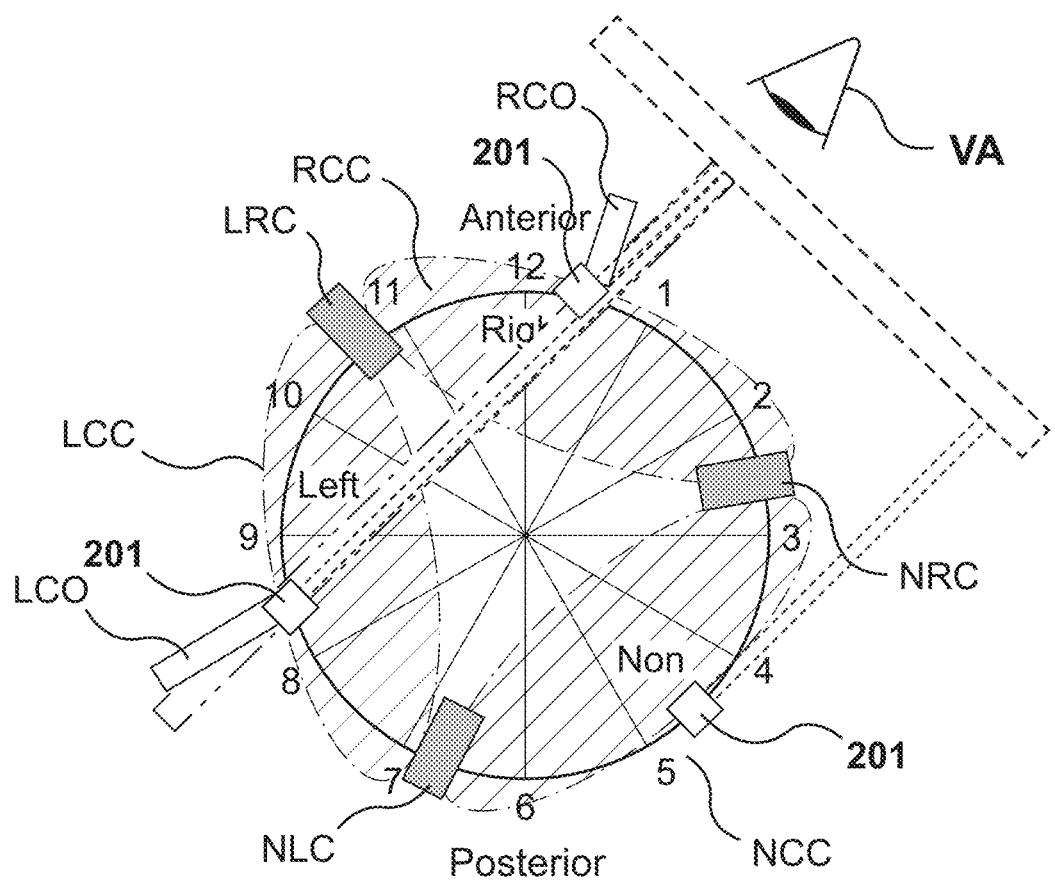
FIGS. 24A-24B depict an illustration of the native aortic valve as viewed from the aorta and including nadir markers of a transcatheter heart valve prosthesis, and a schematic representation of a fluoroscopic image of a native aortic valve using the coronary overlap view.
Figure 24B:
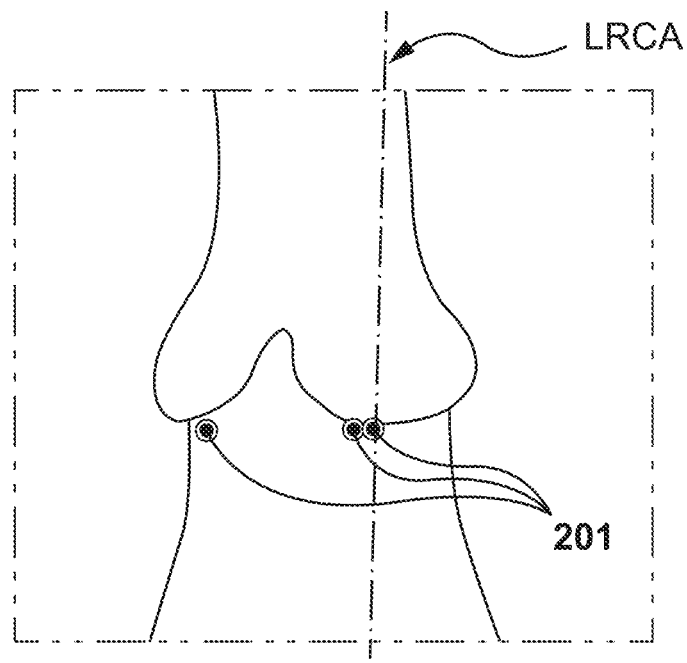

FIGS. 24A and 24B show a particular situation wherein the native valve anatomy is such that the left coronary ostium LCO and the right coronary ostium RCO are each located 60° from the left-right commissure LRC in opposite circumferential directions. In such a situation, as shown in FIG. 24B, the fluoroscopic image will show two of the nadir markers 201 substantially aligned with each other and intersecting with the common longitudinal axis LRCA of the left coronary ostium LCO and the right coronary ostium RCO.

Figure 25A:
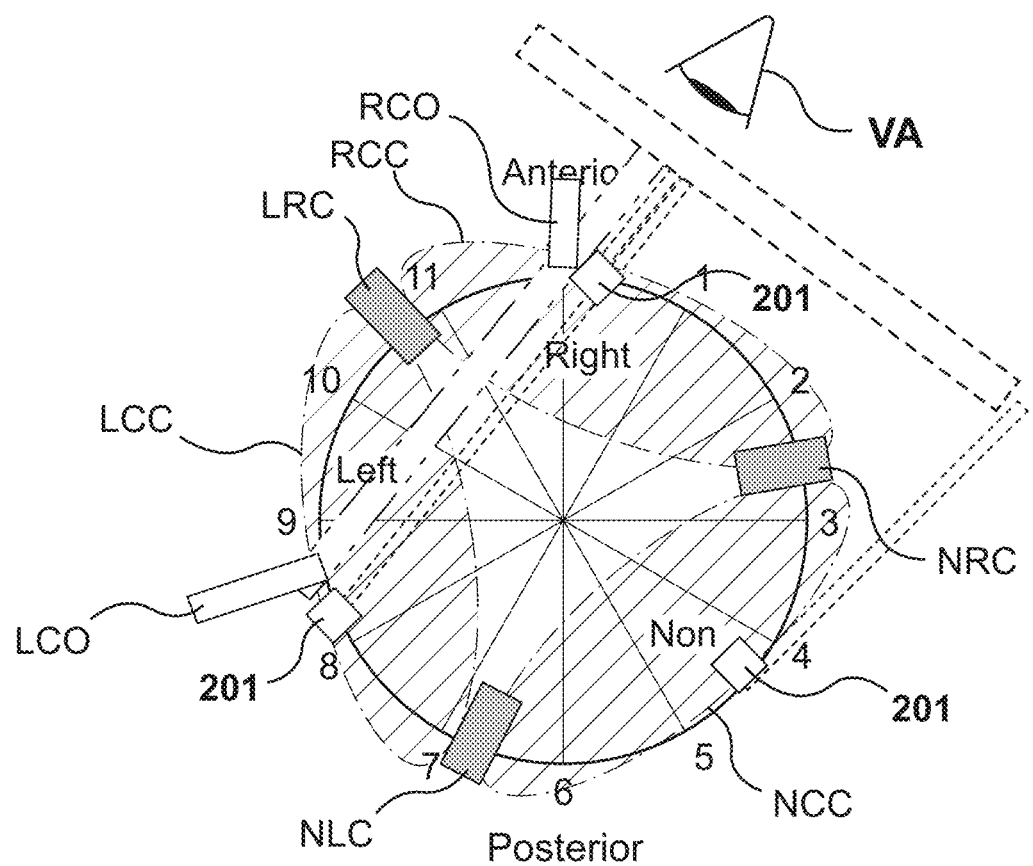
FIGS. 25A-25B depict an illustration of the native aortic valve as viewed from the aorta and including nadir markers of a transcatheter heart valve prosthesis, and a schematic representation of a fluoroscopic image of a native aortic valve using the coronary overlap view.
Figure 25B:
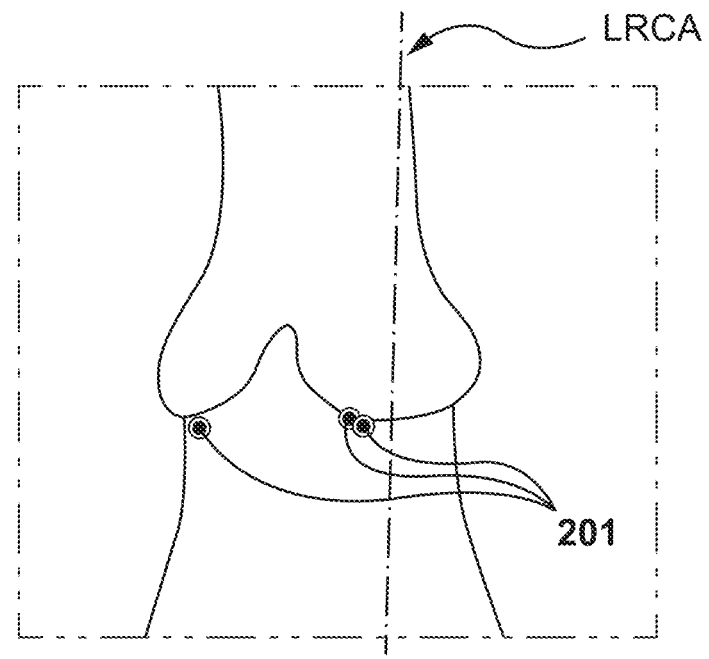

FIGS. 25A and 25B show a situation of the native anatomy wherein the left coronary ostium LCO is located 60° from the left-right commissure LRC in a counterclockwise circumferential direction and the right coronary ostium RCO is located 40° from the left-right commissure LRC in a clockwise circumferential direction, and the viewing angle VA is the coronary overlap view. As can be seen in FIGS. 25A and 25B, two of the nadir markers 201 are substantially aligned adjacent the common longitudinal axis LRCA in the fluoroscopic image (FIG. 25B) in the coronary overlap view, thereby indicating that the nadirs of two of the prosthetic valve leaflets 206 are adjacent the left and right coronary ostia LCO, RCO, such that the prosthetic valve commissures 209 do not block the left and right coronary ostia LCO, RCO.

Figure 26A:
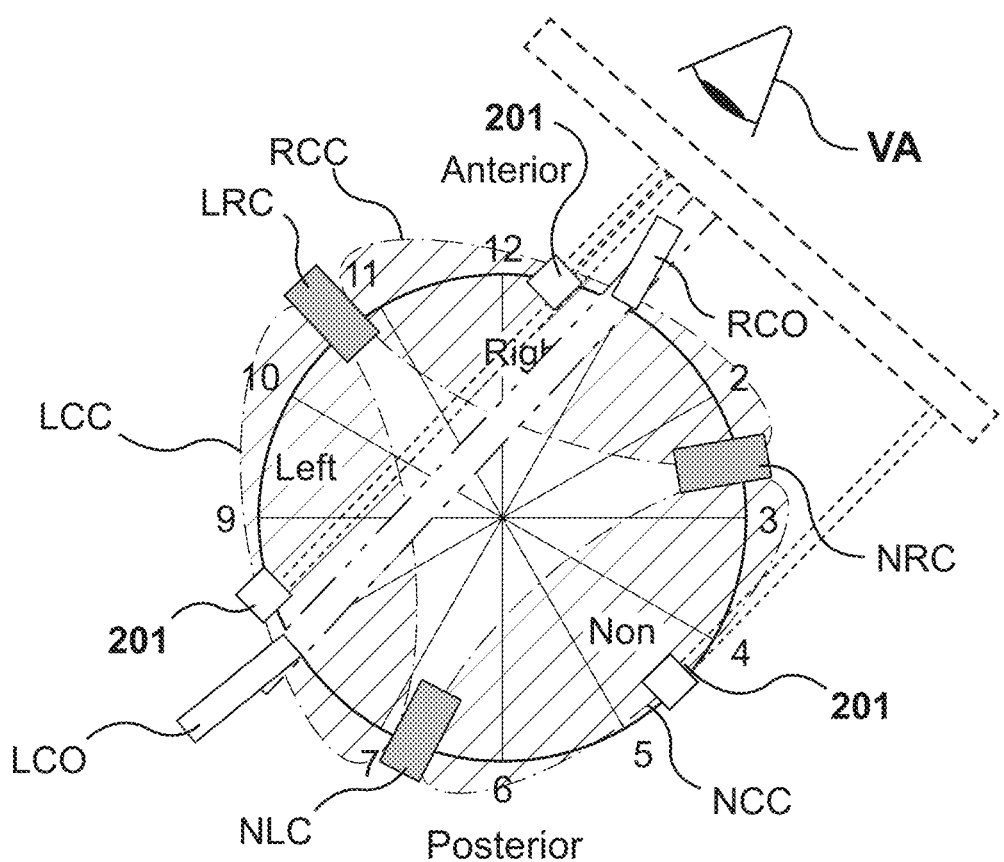
FIGS. 26A-26B depict an illustration of the native aortic valve as viewed from the aorta and including nadir markers of a transcatheter heart valve prosthesis, and a schematic representation of a fluoroscopic image of a native aortic valve using the coronary overlap view.
Figure 26B:
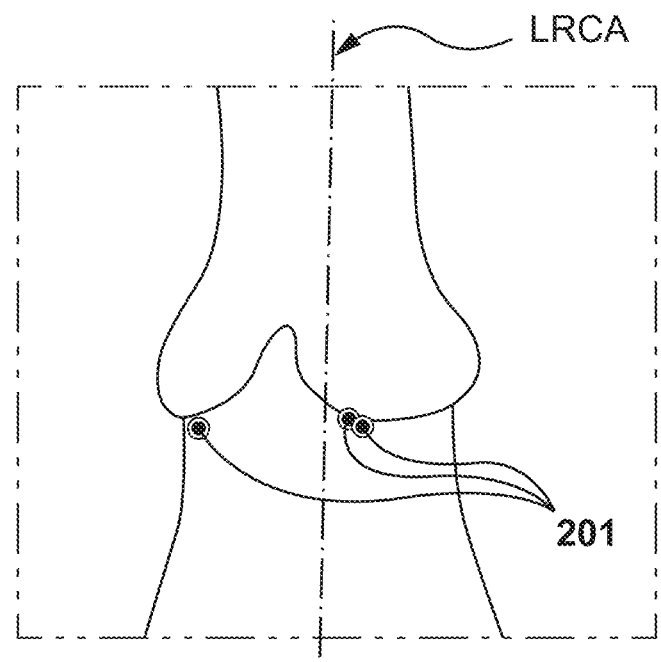

FIGS. 26A and 26B show a situation of the native anatomy wherein the left coronary ostium LCO is located 80° from the left-right commissure LRC in a counterclockwise circumferential direction and the right coronary ostium RCO is located 70° from the left-right commissure LRC in a clockwise circumferential direction, and the viewing angle is the coronary overlap view. As can be seen in FIGS. 26A and 26B, two of the nadir markers 201 are substantially aligned adjacent the common longitudinal axis LRCA in the fluoroscopic image (FIG. 26B) in the coronary overlap view, thereby indicating that the nadirs of two of the prosthetic valve leaflets 206 are adjacent the left and right coronary ostia LCO, RCO, such that the prosthetic valve commissures 209 do not block the left and right coronary ostia LCO, RCO.

From the above explanation, it can be understood that using the coronary overlap view when delivering the transcatheter heart valve prosthesis 200 with the markers 201 at the nadirs of the prosthetic valve leaflets 206, if two of the markers 201 are substantially aligned, then the transcatheter heart valve prosthesis 200 is properly rotationally aligned such that the left and right coronary ostia LCO, RCO are not blocked by the commissures 209 of the prosthetic valve structure 204. As explained above with respect to the transcatheter heart valve prosthesis 100, the coronary overlap view with the markers 201 may be used to confirm that the transcatheter heart valve prosthesis 200 is rotationally aligned such as to not cause coronary obstruction. As explained above, the delivery system 800 is advanced past the native valve leaflets/cusps until a marker on the delivery system, such as a marker located on a distal portion of the capsule 806, is aligned with the annulus of the native heart valve. The capsule 806 may then be retracted proximally to expose the inflow end 212 of the transcatheter heart valve prosthesis 200, enabling the inflow end 212 of the transcatheter heart valve prosthesis 200 to self-expand. If two of the markers 201 are substantially aligned in the fluoroscopic image using the coronary overlap view, then the transcatheter heart valve prosthesis is properly rotationally aligned. If two of the markers are not substantially aligned, then the delivery system 800 may be rotated as described above to properly rotationally align the transcatheter heart valve prosthesis 200.

Although not described specifically with respect to the transcatheter heart valve prosthesis 200, the markers 201 may also be used for longitudinal or depth alignment of the transcatheter heart valve prosthesis 200, as described above with respect to the transcatheter heart valve prosthesis 100.

Further, although the markers 201 have been described as being located at a common longitudinal location along the length of the transcatheter heart valve prosthesis 200, this is not mean to be limiting. In other embodiments, the markers 201 may be offset from each other longitudinally. In such embodiments, the markers 201 that are substantially aligned with each other will not overlap with each on the fluoroscopic image, as shown above. Instead, the substantially aligned markers 201 will be substantially aligned along a common longitudinal axis of the fluoroscopic image.

Further, as described above, although three markers 201 have been shown, more or fewer markers 201 may be utilized. In particular, in an embodiment, two markers 201 located at nadirs of two of the three leaflets 206 may be utilized. In such an embodiment, the pre-procedure CT, the orientation of the transcatheter heart valve prosthesis 200 within the delivery system 800, and the orientation of the delivery system 800 as it is inserted into the femoral artery (for example) are utilized to ensure that the two markers 201 are the two markers that would be substantially aligned if the transcatheter heart valve prosthesis 200 were properly rotationally aligned. If the two markers 201 are not substantially aligned, the delivery system 800 may be rotated as described above to substantially align the two markers 201. The pre-procedure CT and pre-procedure orientation of the transcatheter heart valve prosthesis 200 and the delivery system 800 ensures that the delivery system 800 will not need to be rotated extensively to substantially align the two markers 201.

As described above, if two of the markers 201 are substantially aligned in the coronary overlap view, then the determination is that the transcatheter heart valve prosthesis 200 is properly rotationally aligned to avoid blocking the left and right coronary ostia LCO, RCO. As described above, in the coronary overlap view, the left and right coronary ostia LCO, RCO are co-located such that the common longitudinal axis LRCA thereof is shown in the fluoroscopic image sketches above. However, the location of the common longitudinal axis LRCA is not shown on the fluoroscopic image. In order to show the location of the common longitudinal axis LRCA (as will be used below), left and right coronary ostia LCO, RCO may be illuminated during the procedure through injection of contrast dye into the aortic sinus, as known to those skilled in the art. The common longitudinal axis LRCA can then be marked on the imaging system. In another embodiment, using the pre-procedure CT, the position of the C-arm is determined to achieve the coronary overlap view. This pre-procedure planning can also be used to locate where the common longitudinal axis LRCA should be located in the fluoroscopic image such that the common longitudinal axis LRCA can be added to the fluoroscopic image. The common longitudinal axis LRCA can be added to the fluoroscopic image digitally or manually.

Thus, having the common longitudinal axis LRCA as shown in FIGS. 23B, 24B, 25B, and 26B, it can be seen that is some situations the substantially aligned nadir markers 201 are located to the left of the common longitudinal axis LRCA and in other situations the substantially aligned nadir markers are to the right of the common longitudinal axis LRCA in the fluoroscopic image in the cusp overlap view. There is also the particular situation shown in FIG. 24B where the substantially aligned nadir markers 201 are also substantially aligned with the common longitudinal axis LRCA. Whether the substantially aligned nadir markers 201 are to the left of the common longitudinal axis LRCA or to the right of the common longitudinal axis LRCA in the fluoroscopic image depends on the inter-coronary angle between the left coronary ostium LCO and the right coronary ostium RCO with the native left-right commissure therebetween. In the examples described above, the locations of the left coronary ostium LCO and the right coronary ostium RCO were given with respect to the native left-right commissure LRC. The inter-coronary angle for each of the examples is the sum of the two angles. Thus, for FIG. 23A, the inter-coronary angle is 150°, for FIG. 24A, the inter-coronary angle is 120°, for FIG. 25A, the inter-coronary angle is 100°, and for FIG. 26A, the inter-coronary angle is 150°. As can be seen in the examples provided, if the inter-coronary angle is less than 120°, the substantially aligned nadir markers 201 will be to the right of the common longitudinal axis LRCA and if the inter-coronary angle is greater than 120°, the substantially aligned nadir markers 201 will be to the left of the common longitudinal axis LRCA. If the inter-coronary angle is 120°, the substantially aligned nadir markers 201 should also be substantially aligned with the common longitudinal axis LRCA, as shown in FIG. 24B.

It is evident that the further away the inter-coronary angle is from 120° (either greater than or less than 120°), the further a horizontal distance HD (either left or right) between the substantially aligned nadir markers 201 and the common longitudinal axis LRCA in the coronary overlap view. Thus, using this, a target horizontal distance THD can be calculated during the pre-procedure process using information regarding the native anatomy from the pre-procedure CT and a geometric solver, such as geometric solvers available in computer aided design software (CAD), such as SolidWorks. The target horizontal distance THD provides the best match of the geometry of the native annulus with the transcatheter heart valve prosthesis 200 having the nadir markers 120° apart from each other around the circumference of the transcatheter heart valve prosthesis 200. Thus, when evaluating the rotational orientation of the transcatheter heart valve prosthesis 200 as explained above, the target horizontal distance THD may be utilized to orient the transcatheter heart valve prosthesis 200 at the best rotational orientation to avoid blocking the left and right coronary ostia LCO, RCO.

Figure 27A:
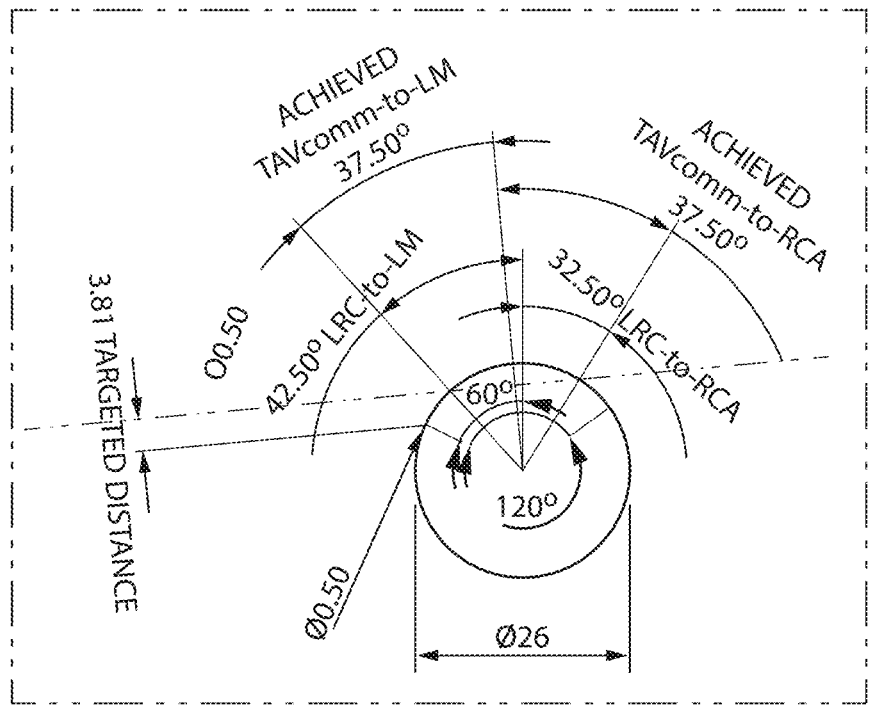
FIGS. 27A-27B depict examples of calculating a target horizontal distance based on dimensions of a native valve.

FIG. 27A provides an example of the target horizontal distance THD calculated in the pre-procedure process using information regarding the native anatomy. In the example of FIG. 27A, the annulus is circular, has a diameter of 26 mm, the left coronary ostium LCO is located 42.5° from the left-right commissure LRC in a counter-clockwise direction, and the right coronary ostium RCO is located 32.5° from the left-right commissure LRC in a clockwise direction, resulting in the inter-coronary angle being 75°. With the nadir markers 201 located 120° apart, the target horizontal distance THD of the substantially aligned nadir markers 201 from the common longitudinal axis LRCA is 3.81 mm from the common longitudinal axis LRCA as seen on the fluoroscopic image in the coronary overlap view. As the inter-coronary angle is less than 120° the target horizontal distance THD of 3.81 mm would be right of the common longitudinal axis LRCA as seen on the fluoroscopic image in the coronary overlap view.

Figure 27B:
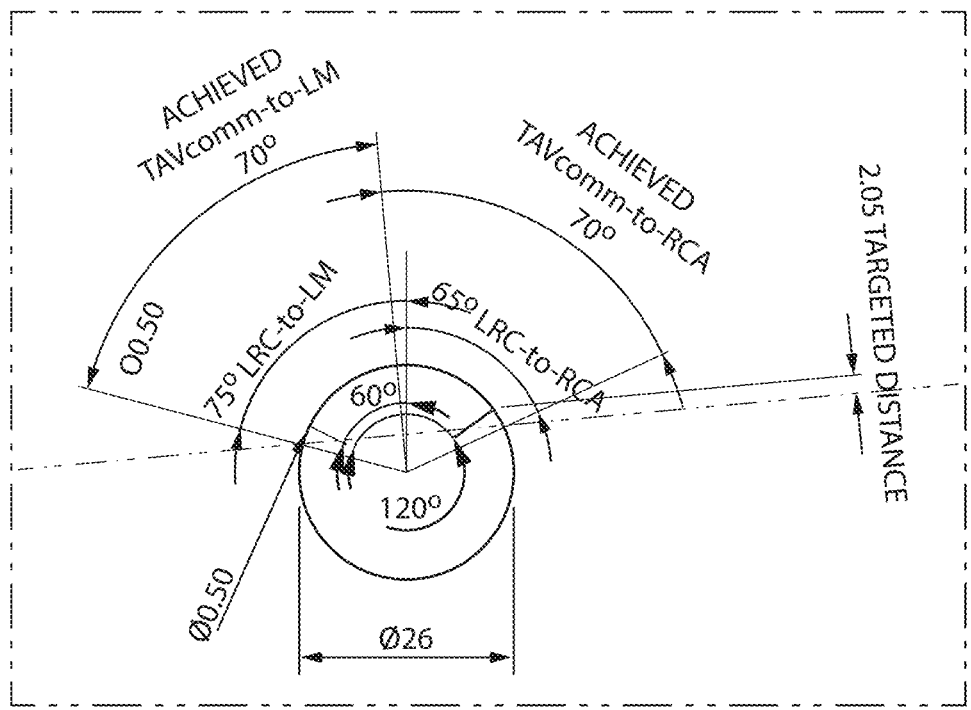

FIG. 27B provides another example of the target horizontal distance THD calculated in the pre-procedure process using information regarding the native anatomy. In the example of FIG. 27B, the annulus is circular, has a diameter of 26 mm, the left coronary ostium LCO is located 75° from the left-right commissure LRC in a counter-clockwise direction, and the right coronary ostium RCO is located 65° from the left-right commissure LRC in clockwise direction, resulting in the inter-coronary angle being 140°. With the nadir markers 201 located 120° apart, the target horizontal distance THD of the substantially aligned nadir markers 201 from the common longitudinal axis LRCA is 2.05 mm from the common longitudinal axis LRCA as seen on the fluoroscopic image in the coronary overlap view. As the inter-coronary angle is greater than 120° the target horizontal distance THD of 2.05 mm would be left of the common longitudinal axis LRCA as seen on the fluoroscopic image in the coronary overlap view.

Figure 28A:
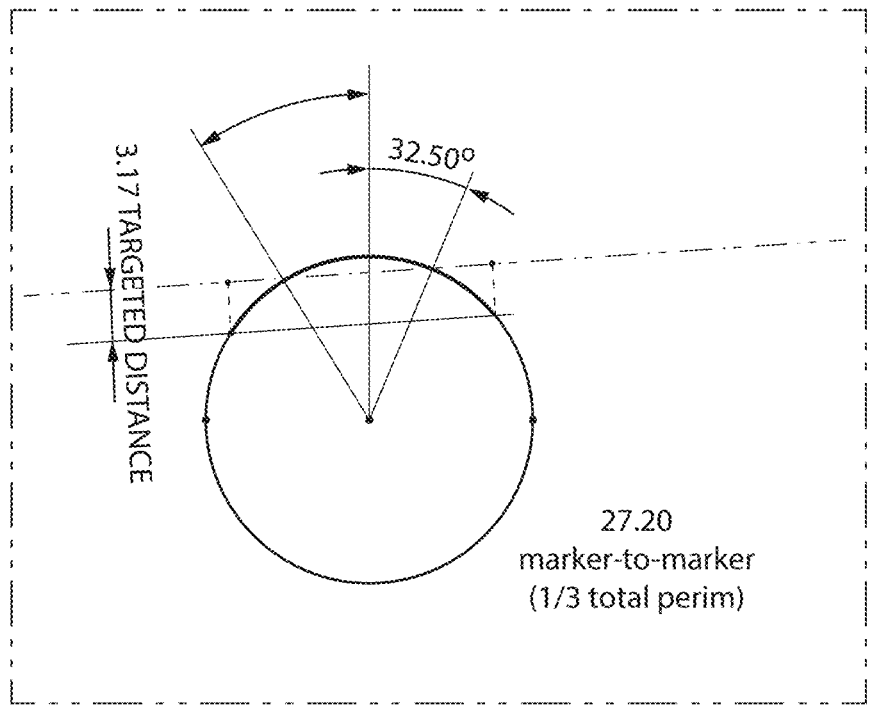
FIGS. 28A-28B depict examples of calculating a target horizontal distance based on dimensions of a native valve.

FIG. 28A provides another example of the target horizontal distance THD calculated in the pre-procedure process using information regarding the native anatomy. In the example of FIG. 28A, the annulus is elliptical, has a major diameter of 31 mm, the left coronary ostium LCO is located 42.5° from the left-right commissure LRC in a counter-clockwise direction, and the right coronary ostium RCO is located 32.5° from the left-right commissure LRC in a clockwise direction, resulting in the inter-coronary angle being 75°. With the nadir markers 201 located 120° apart, the target horizontal distance THD of the substantially aligned nadir markers 201 from the common longitudinal axis LRCA is 3.17 mm from the common longitudinal axis LRCA as seen on the fluoroscopic image in the coronary overlap view. As the inter-coronary angle is less than 120° the target horizontal distance THD of 3.17 mm would be right of the common longitudinal axis LRCA as seen on the fluoroscopic image in the coronary overlap view.

Figure 28B:
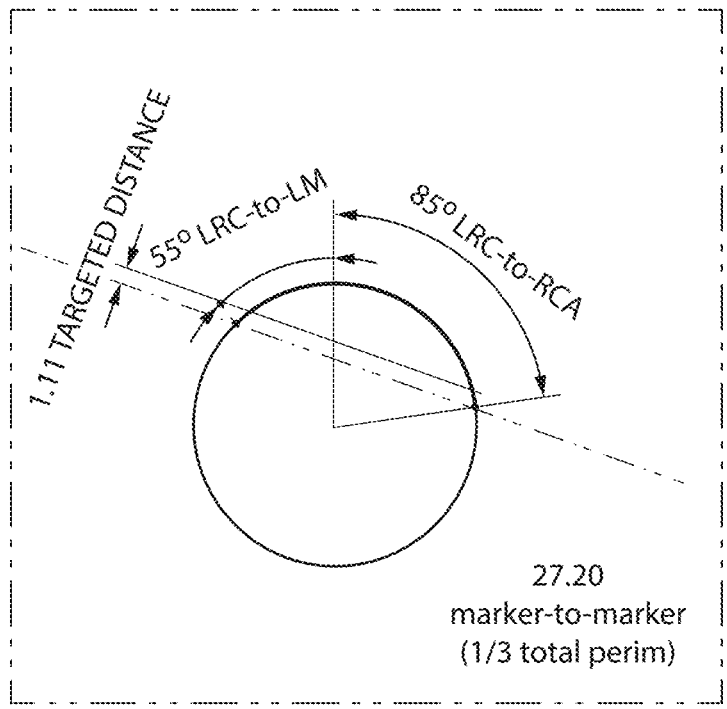

FIG. 28B provides another example of the target horizontal distance THD calculated in the pre-procedure process using information regarding the native anatomy. In the example of FIG. 28B, the annulus is elliptical, has a diameter of 31 mm, the left coronary ostium LCO is located 55° from the left-right commissure LRC in a counter-clockwise direction, and the right coronary ostium RCO is located 85° from the left-right commissure LRC in a clockwise direction, resulting in the inter-coronary angle being 140°. With the nadir markers 201 located 120° apart, the target horizontal distance THD of the substantially aligned nadir markers 201 from the common longitudinal axis LRCA is 1.11 from the common longitudinal axis LRCA as seen on the fluoroscopic image in the coronary overlap view. As the inter-coronary angle is greater than 120° the target horizontal distance THD of 1.11 mm would be left of the common longitudinal axis LRCA as seen on the fluoroscopic image in the coronary overlap view.

Figure 29A:
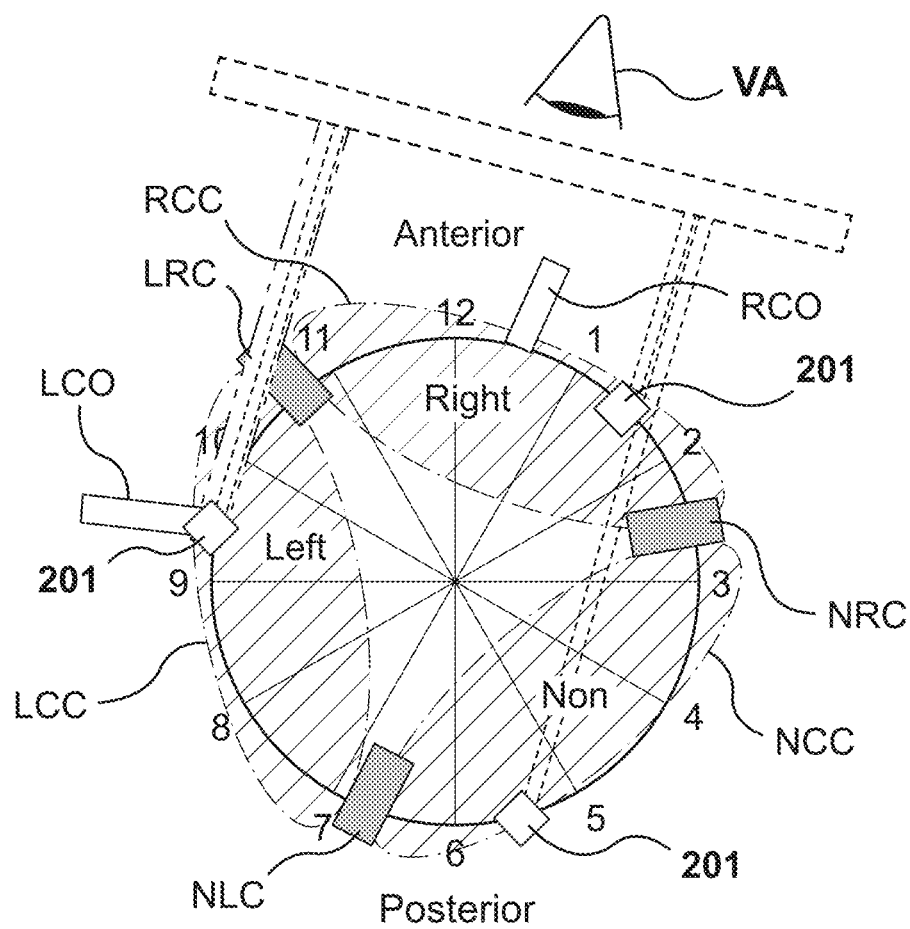
FIGS. 29A-29B depict an illustration of the native aortic valve as viewed from the aorta and including nadir markers of a transcatheter heart valve prosthesis, and a schematic representation of a fluoroscopic image of a native aortic valve using a coronary isolation view.
Figure 29B:
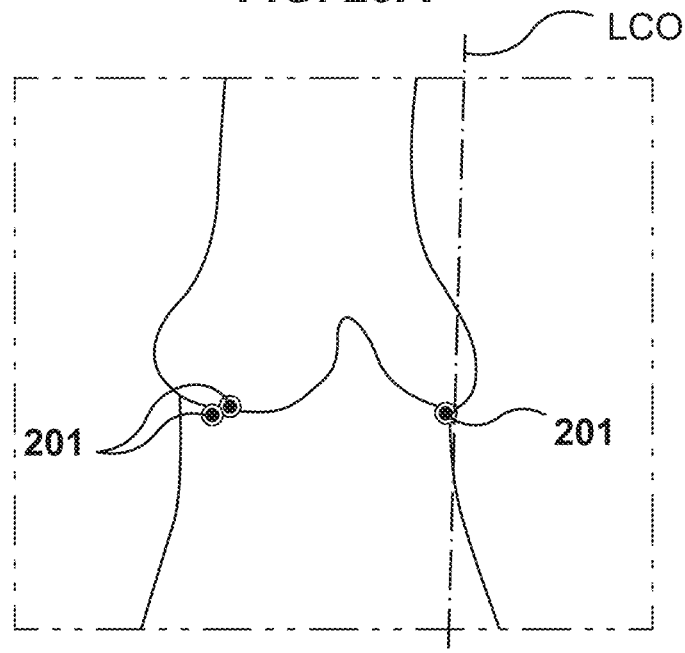

In another embodiment, described with respect to FIGS. 29A and 29B, it is understood that except for the situation of the native inter-coronary angle being 120°, none of the nadir markers 201 will be rotationally aligned with the respective left and right coronary ostia LCO, RCO. Instead, the methodology described above provides the best match for both of the substantially aligned nadir markers 201 in the coronary overlap view being close to the respective left and right coronary ostia LCO, RCO to avoid blocking the left and right coronary ostia LCO, RCO with the commissures 209 of the prosthetic valve structure 204. However, in some circumstances, it may be particularly important to ensure that one of the nadir markers 201 is rotationally aligned with left coronary ostium LCO or the right coronary ostium RCO to provide improved post-coronary intervention (PCI) access to the particular coronary ostia. For example, and not by way of limitation, it may be known that one of the coronary arteries is already diseased, and the future access to that particular coronary artery is more likely than to the other coronary artery. In such a situation, instead of utilizing the coronary overlap view as described above, a single coronary isolation view may be utilized. FIG. 28A shows an example of a single coronary isolation view in which C-arm is rotated to be aligned with the left coronary ostium LCO. As shown in FIG. 29A, the left coronary ostium LCO is 45° from the left-right commissure LRC in a counterclockwise circumferential direction and the right coronary ostium RCO is 55° from the left-right commissure ins a clockwise circumferential direction. With the view angle VA set to the single coronary isolation view for the left coronary ostium LCO, the transcatheter heart valve prosthesis 200 is rotationally aligned as desired when one of the nadir markers 201 is substantially aligned with the left coronary ostium LCO, as marked by its axis in the fluoroscopic image of FIG. 29B.

As explained above, the transcatheter heart valve prostheses 100 and 200 are not limited to the specific designs shown and described. In other embodiments, transcatheter heart valve prostheses similar to those described above may include access or enlarged cells or windows for PCI access to the coronary ostia after the transcatheter is deployed. Details regarding specific designs are described in U.S. patent application Ser. No. 17/540,304, filed Dec. 2, 2021, the contents of which are incorporated by reference herein in their entirety. The techniques and markers described herein can be used with the transcatheter heart valve prostheses with access cells/windows to rotationally align the prosthetic valve commissures thereof with the native valve commissures and/or align the access cells/windows thereof with the left coronary ostia and/or the right coronary ostia. The markers as described above may be located as described above, included variations mentioned. FIGS. 30A-33B show embodiments of the transcatheter heart valve prostheses disclosed in the above-referenced patent application with markers for rotational orientation in keeping with the present application.

Figure 30A:
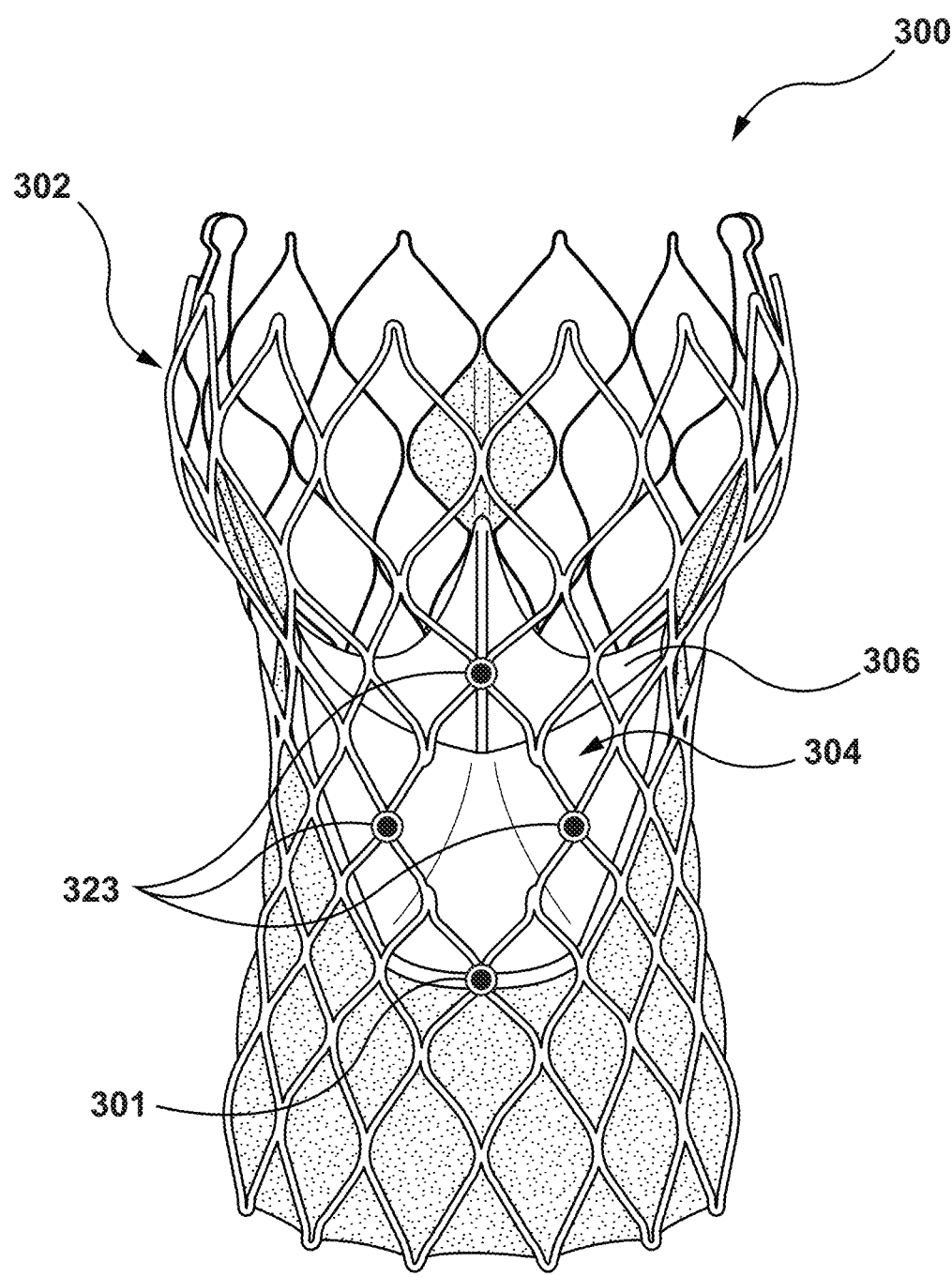
FIGS. 30A-30B depict an illustration of a transcatheter heart valve prosthesis in accordance with embodiments hereof.
Figure 30B:
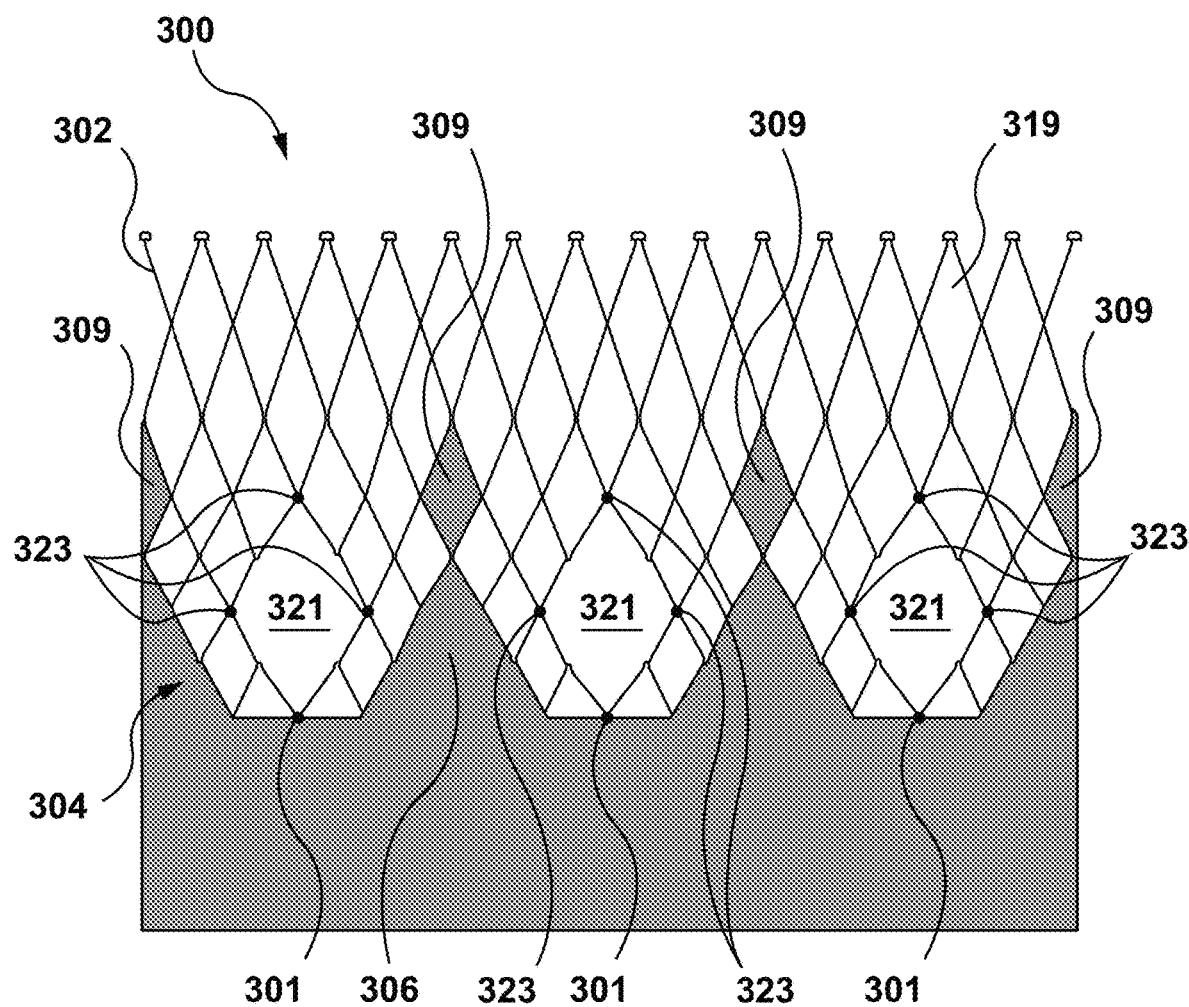

FIGS. 30A-30B show an embodiment of a transcatheter heart valve prosthesis 300 including a frame 302 and a valve structure 304. Details of the transcatheter heart valve prosthesis 300 are not described herein as they are similar to the transcatheter heart valve prostheses 100 and 200, except for access cells 321 which are enlarged as compared to other cells 319 of the frame 302, and are explained in detail in U.S. patent application Ser. No. 17/540,304, filed Dec. 2, 2021, which is incorporated by reference herein in its entirety. As shown in FIGS. 30A-30B, a nadir marker 301 is coupled to the frame 302 at an inflow end of each access cell 321. In the embodiment of FIGS. 30A-30B, the access cells 321 are generally diamond-shaped and the nadir markers 301 are disposed at the inflow point of the diamond. In other embodiments, as discussed above, only two of the access cells 321 have nadir markers 301. The nadir markers 301 in FIGS. 30A-30B are axially aligned with the nadirs of the leaflets 306 of the valve structure 304, or axially aligned with a mid-point between the commissures 309 of the leaflets 306 of the valve structure 304. The nadir markers 301 can be used as described above to rotationally align the transcatheter heart valve prosthesis 300 such that one of the access cells 321 is rotationally aligned with the left coronary ostia LCO and another one of the access cells 321 is rotationally aligned with the right coronary ostia RCO.

Further, the location of the nadir markers 301 at the inflow ends of the access cells 321 may also serve as a guide for a post-implantation procedure. In other words, after implantation of the transcatheter heart valve prosthesis 300, if a future transcatheter procedure is needed, such as angioplasty and/or stent implantation, for which access to one of the coronary ostia is needed, the nadir marker 301 may serve as a guide. In particular, the nadir marker 301 at the coronary ostium to which access is needed will appear on the fluoroscopic image and inform the clinician that the access cell 321 is downstream of the nadir marker 301 (vertically upward for an aortic valve). This will assist the clinician in guiding the catheter for the post-implantation procedure through the access cell 321. In embodiments, shown in FIGS. 30A-30B as optional, additional markers 323 may be included to mark the boundaries of the access cells 321. In the embodiment shown in FIGS. 30A-30B, the markers 323 are located at the other three points of the diamond shaped access cells 321. However, this is not meant to be limiting, and other locations, fewer locations, or more locations may be used for the markers 323.

Figure 31A:
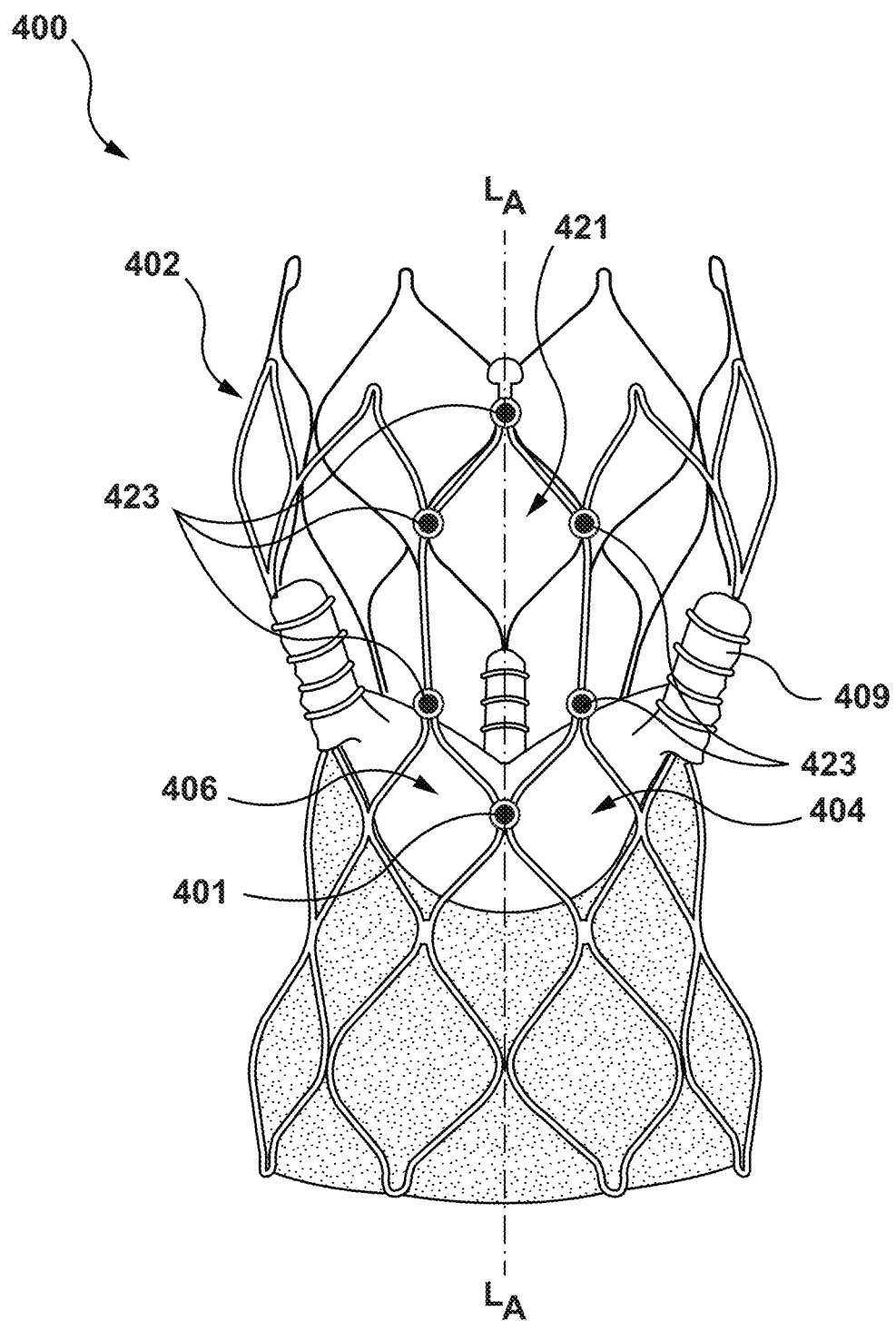
FIGS. 31A-31B depict an illustration of a transcatheter heart valve prosthesis in accordance with embodiments hereof.
Figure 31B:
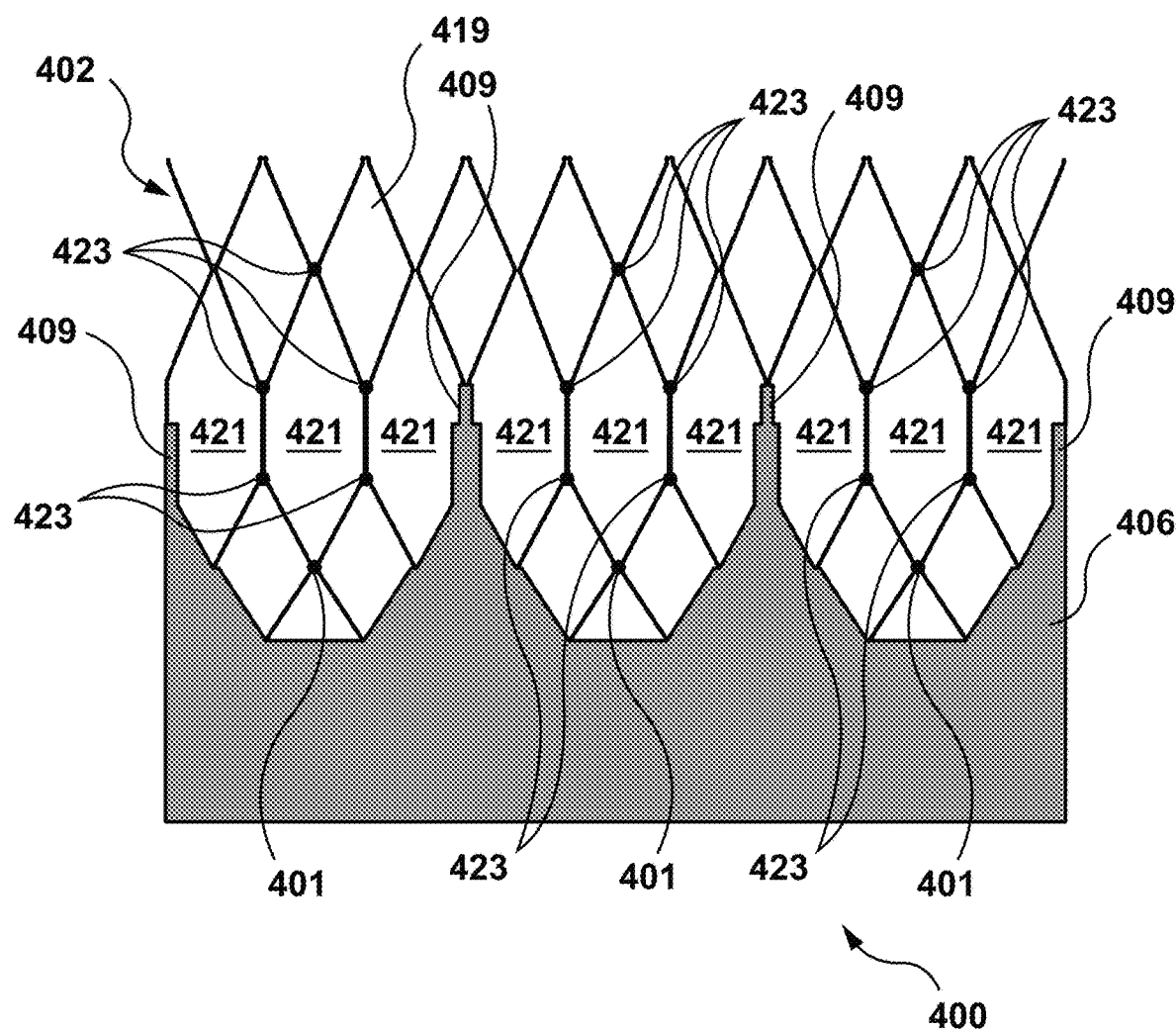

FIGS. 31A-31B show an embodiment of a transcatheter heart valve prosthesis 400 including a frame 402 and a valve structure 404. Details of the transcatheter heart valve prosthesis 400 are not described herein as they are similar to the transcatheter heart valve prostheses 100 and 200, except for access cells 421 which are enlarged as compared to other cells 419 of the frame 402, and are explained in detail in U.S. patent application Ser. No. 17/540,304, filed Dec. 2, 2021, which is incorporated by reference herein in its entirety. As shown in FIGS. 31A-31B, a nadir marker 401 is coupled to the frame 402 at an inflow end of each of the three access cells 421 that is the middle access cell 421 between each commissure 409. As shown in FIG. 31B, circumferentially between adjacent commissures 409 of the valve structure 404 there are three access cells 421 disposed circumferentially adjacent to each other. In the embodiment of FIGS. 31A-31B, the nadir markers 401 are coupled to the middle access cell 421. In the embodiment of FIGS. 31A-31B, the access cells 421 are generally elongated hexagons and the nadir markers 401 are disposed at the inflow point of the elongated hexagon. In other embodiments, as discussed above, only two of the access cells 421 have nadir markers 401. The nadir markers 401 in FIGS. 31A-31B are axially aligned with the nadirs of the leaflets 406 of the valve structure 404, or axially aligned with a mid-point between the commissures 409 of the leaflets 406 of the valve structure 404. The nadir markers 401 can be used as described above to rotationally align the transcatheter heart valve prosthesis 400 such that one of the access cells 421 is rotationally aligned with the left coronary ostia LCO and another one of the access cells 421 is rotationally aligned with the right coronary ostia RCO.

Further, the location of the nadir markers 401 at the inflow ends of the access cells 421 may also serve as a guide for a post-implantation procedure. In other words, after implantation of the transcatheter heart valve prosthesis 400, if a future transcatheter procedure is needed, such as angioplasty and/or stent implantation, for which access to one of the coronary ostia is needed, the nadir marker 401 may serve as a guide. In particular, the nadir marker 401 at the coronary ostium to which access is needed will appear on the fluoroscopic image and inform the clinician that the access cell 421 is downstream of the nadir marker 401 (vertically upward for an aortic valve). This will assist the clinician in guiding the catheter for the post-implantation procedure through the access cell 421. In embodiments, shown in FIGS. 31A-31B as optional, additional markers 423 may be included to mark the boundaries of the middle access cells 421. In the embodiment shown in FIGS. 31A-31B, the markers 423 are located at the other angles of the elongated hexagon shaped access cells 421. However, this is not meant to be limiting, and other locations, fewer locations, or more locations may be used for the markers 423.

Figure 32A:
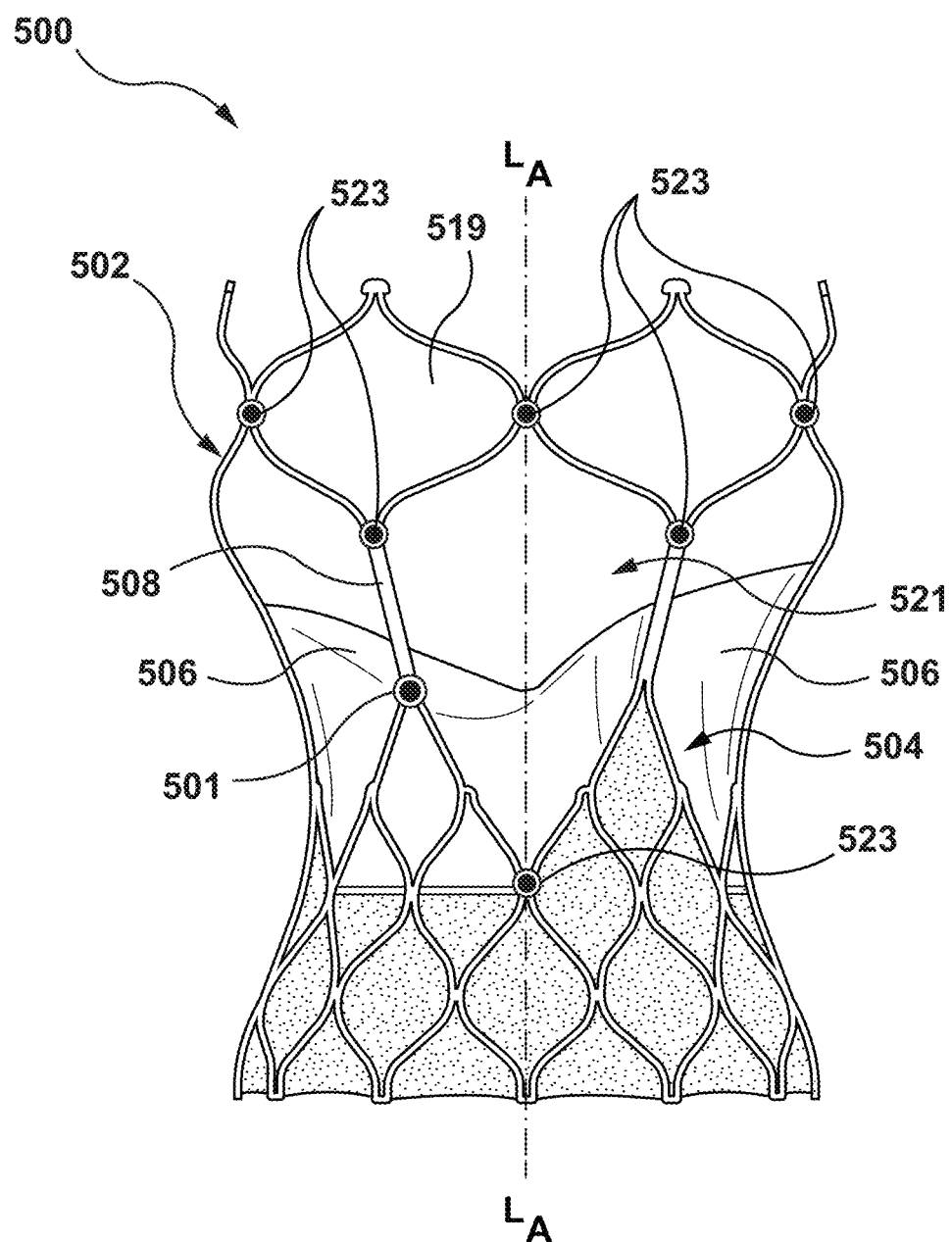
FIGS. 32A-32B depict an illustration of a transcatheter heart valve prosthesis in accordance with embodiments hereof.
Figure 32B:
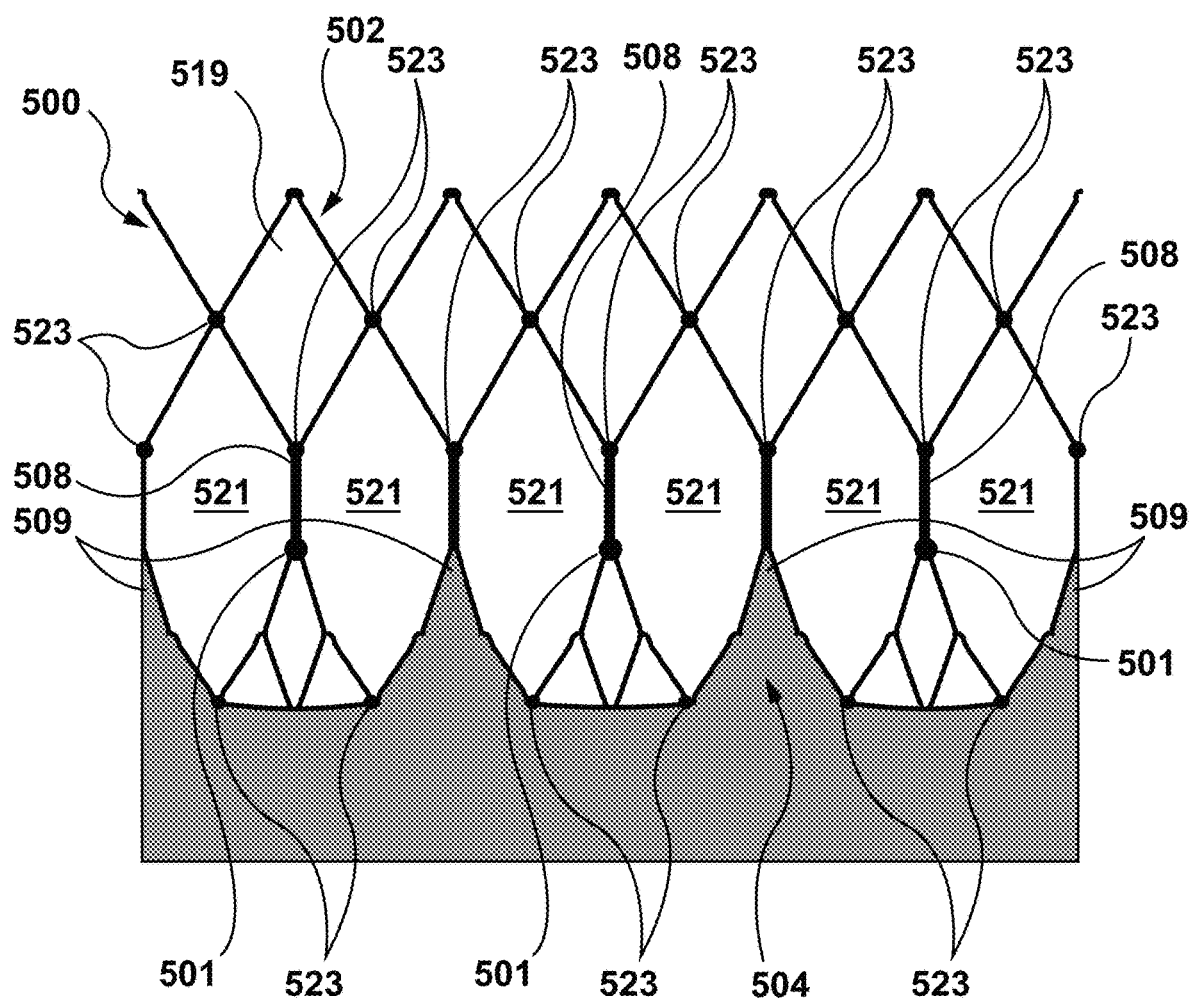

FIGS. 32A-32B show an embodiment of a transcatheter heart valve prosthesis 500 including a frame 502 and a valve structure 504. Details of the transcatheter heart valve prosthesis 500 are not described herein as they are similar to the transcatheter heart valve prostheses 100 and 200, except for access cells 521 which are enlarged as compared to other cells 519 of the frame 502, and are explained in detail in U.S. patent application Ser. No. 17/540,304, filed Dec. 2, 2021, which is incorporated by reference herein in its entirety. As shown in FIGS. 31A-31B, a nadir marker 501 is coupled to the frame 502 at a location on the frame 502 that is a circumferential mid-point between circumferentially adjacent commissures 509 of the valve structure 504. In the embodiment of FIGS. 31A-31B, there are two access cells 521 between each circumferentially adjacent commissure 509. Therefore, in the embodiment of FIGS. 32A-32B, the nadir markers 501 are located at a strut 508 that is shared by both of the access cells 521 between the adjacent commissures 509. In the embodiment shown in FIGS. 32A-32B, the nadir markers 501 are located at the inflow ends of each strut 508, but this is not meant to be limiting. The nadir markers 501 could be located anywhere along the length of the strut 508. In the embodiment of FIGS. 32A-32B, the access cells 521 are generally elongated hexagons that are larger than the access cells 521 of FIGS. 31A-31B; hence there are two access cells 521 circumferentially between circumferentially adjacent commissures 509, rather than three access cells as in FIGS. 31A-31B. In other embodiments, as discussed above, only two of the struts 508 shared by access cells 521 have nadir markers 501. The nadir markers 501 in FIGS. 32A-32B are axially aligned with the nadirs of the leaflets 506 of the valve structure 504, or axially aligned with a mid-point between the commissures 509 of the leaflets 506 of the valve structure 504. The nadir markers 501 can be used as described above to rotationally align the transcatheter heart valve prosthesis 500 such that access cells 521 are rotationally aligned with the left coronary ostia LCO and the right coronary ostia RCO.

Further, the nadir markers 501 may also serve as a guide for a post-implantation procedure. In other words, after implantation of the transcatheter heart valve prosthesis 500, if a future transcatheter procedure is needed, such as angioplasty and/or stent implantation, for which access to one of the coronary ostia is needed, the nadir marker 501 may serve as a guide. In particular, the nadir marker 501 at the coronary ostium to which access is needed will appear on the fluoroscopic image and inform the clinician that the access cells 521 are adjacent to the nadir marker 501. This will assist the clinician in guiding the catheter for the post-implantation procedure through one of the access cells 521. In embodiments, shown in FIGS. 32A-32B as optional, additional markers 523 may be included to mark the boundaries of the access cells 521. In the embodiment shown in FIGS. 32A-32B, the markers 523 are located at several of the other angles of the elongated hexagon shaped access cells 521. However, this is not meant to be limiting, and other locations, fewer locations, or more locations may be used for the markers 523.

Figure 33A:
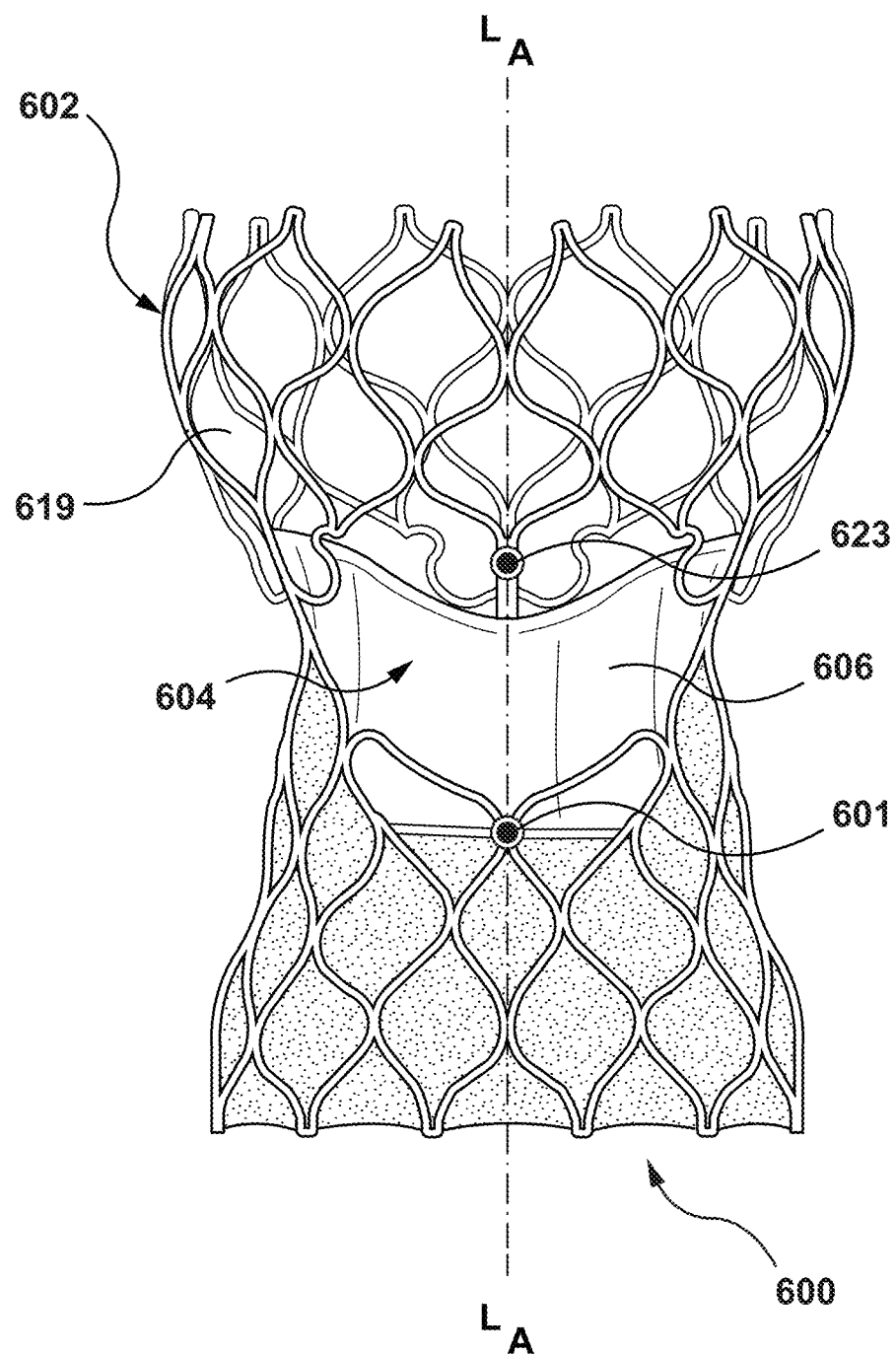
FIGS. 33A-33B depict an illustration of a transcatheter heart valve prosthesis in accordance with embodiments hereof.
Figure 33B:
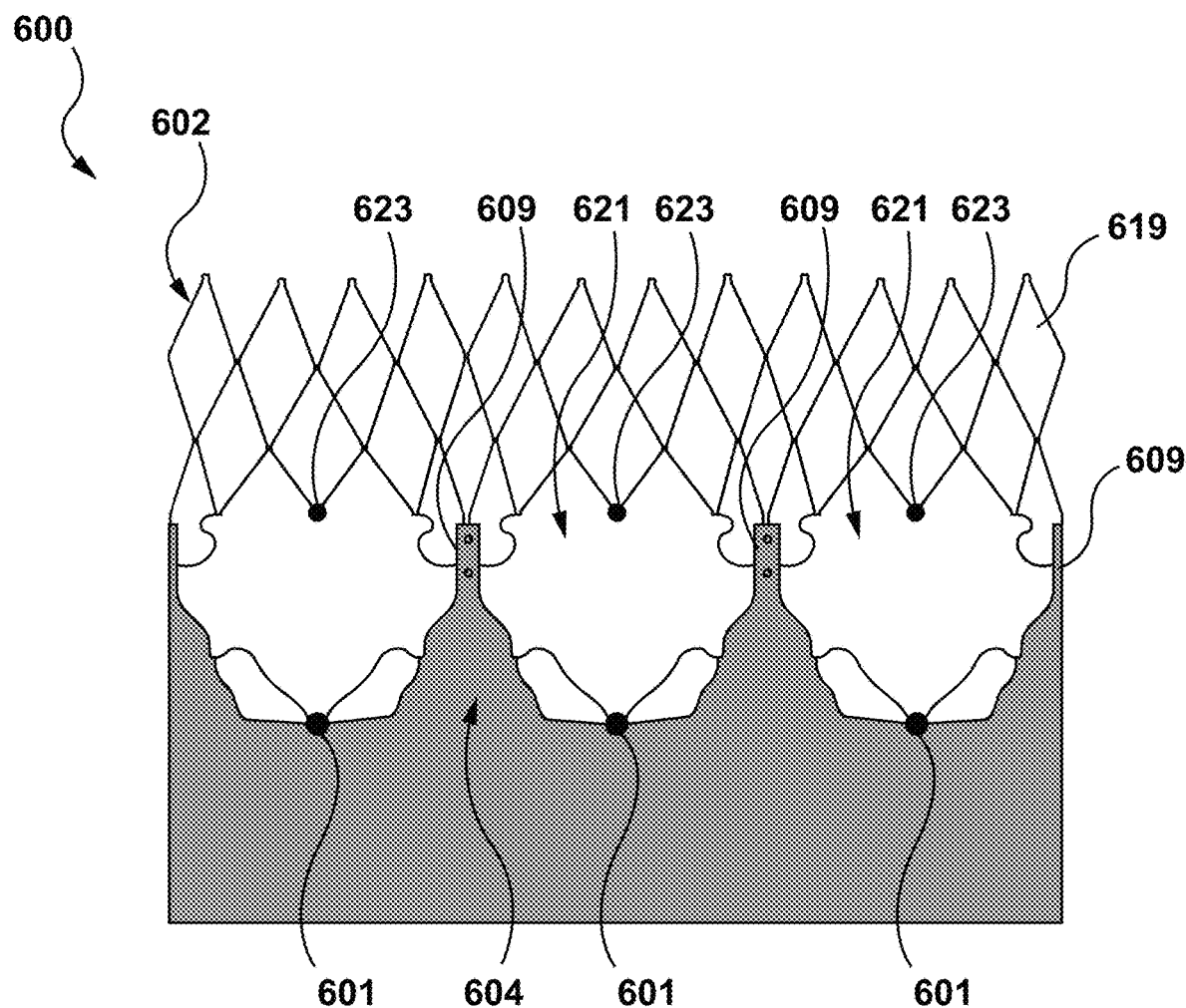

FIGS. 33A-33B show an embodiment of a transcatheter heart valve prosthesis 600 including a frame 602 and a valve structure 604. Details of the transcatheter heart valve prosthesis 600 are not described herein as they are similar to the transcatheter heart valve prostheses 100 and 200, except for access cells 621 which are enlarged as compared to other cells 619 of the frame 602, and are explained in detail in U.S. patent application Ser. No. 17/540,304, filed Dec. 2, 2021, which is incorporated by reference herein in its entirety. As shown in FIGS. 33A-33B, a nadir marker 601 is coupled to the frame 602 at an inflow end of each access cell 621. In other embodiments, as discussed above, only two of the access cells 621 have nadir markers 601. The nadir markers 601 in FIGS. 33A-33B are axially aligned with the nadirs of the leaflets 606 of the valve structure 604, or axially aligned with a mid-point between the commissures 609 of the leaflets 606 of the valve structure 604. The nadir markers 601 can be used as described above to rotationally align the transcatheter heart valve prosthesis 600 such that one of the access cells 621 is rotationally aligned with the left coronary ostia LCO and another one of the access cells 621 is rotationally aligned with the right coronary ostia RCO. The nadir markers 601 in FIGS. 33A-33B are axially aligned with the nadirs of the leaflets 606 of the valve structure 604, or axially aligned with a mid-point between the commissures 609 of the leaflets 606 of the valve structure 604. The nadir markers 601 can be used as described above to rotationally align the transcatheter heart valve prosthesis 600 such that access cells 621 are rotationally aligned with the left coronary ostia LCO and the right coronary ostia RCO.

Further, the nadir markers 601 may also serve as a guide for a post-implantation procedure. In other words, after implantation of the transcatheter heart valve prosthesis 600, if a future transcatheter procedure is needed, such as angioplasty and/or stent implantation, for which access to one of the coronary ostia is needed, the nadir marker 601 may serve as a guide. In particular, the nadir marker 601 at the coronary ostium to which access is needed will appear on the fluoroscopic image and inform the clinician that the access cell 621 is downstream of the nadir marker 601. This will assist the clinician in guiding the catheter for the post-implantation procedure through the access cell 621. In embodiments, shown in FIGS. 33A-33B as optional, additional markers 623 may be included to mark the boundaries of the access cells 621. In the embodiment shown in FIGS. 32A-32B, the markers 623 are at the outflow end of each access cell 621 axially aligned with the nadir markers 601. Thus, the additional markers 623 are also axially aligned with the nadirs of the leaflets 606 and thus could serve as nadir markers. The location of the additional marker 623 at each access cell 621 is not meant to be limiting, and other locations, fewer locations, or more locations may be used for the markers 623.

As explained above, the nadir markers 301, 401, 501, 601 in each of examples above need not be immediately adjacent the access cells. In other words, as explained with respect to the embodiment of FIG. 22, nadir markers need only be substantially axially aligned with the nadirs of the prosthetic valve leaflets to rotationally align the heart valve prosthesis. However, the nadir markers 301, 401, 501, 601 in their respective embodiments are serving the dual purpose of rotational alignment and marking the location of the access cells. As explained above, the nadir markers 201 that are substantially axially aligned with the nadirs, but not located at the access cells, could be used instead to rotationally align the transcatheter heart valve prostheses 300, 400, 500, 600 such that the access cells thereof are aligned with the coronary ostia. Further, in other embodiments, the markers 101 described above could be used to rotationally align the transcatheter heart valve prostheses 300, 400, 500, 600 such that the commissures thereof are rotationally aligned with the native commissures, as explained above, resulting in the access cells thereof being rotationally aligned with the coronary ostia.

Further, as noted above, the additional markers explained above for marking the location of the access cells are optional. Further, more or fewer additional markers may be utilized. Therefore, for example, embodiments that show, for example, three additional markers for an access cell, include a single additional marker, two additional markers, three additional markers, and more than three additional markers. This applies to embodiments in the same manner to embodiments that show one additional marker or five additional markers for each access cell.

As explained above, based on pre-procedure imaging and the known orientation of the transcatheter heart valve prosthesis within the delivery system 800, the delivery system 800 can be oriented to achieve alignment of the prosthetic valve commissures with the native valve commissures to the extent possible and/or two of the prosthetic valve nadirs with two of the coronary ostia. As explained above, the markers and methods described herein can be used to confirm that the proper rotational orientation has been achieved, or to adjust the position of the delivery system 800, and hence the transcatheter heart valve prosthesis therein, if the proper rotational orientation has not been achieved. However, the known relationship between the transcatheter heart valve prosthesis and the delivery system 800 is only achieved if the transcatheter heart valve prosthesis is properly loaded into the delivery system 800. For example, in the embodiments above, the transcatheter heart valve prostheses include two paddles, such as the two paddles 150 in the transcatheter heart valve prosthesis 100. As explained above, one of the paddles 150 (with the C-shape) is aligned with one of the commissures 109 of the valve structure 104, and the other paddle 150 is spaced 180° around the circumference of the frame from the C-shaped paddle 150. With three commissures in the embodiments above, the non-C-shaped paddle 150 is not aligned with one of the three commissures. In such a situation, if the transcatheter heart valve prosthesis 100 is not loaded in the delivery system 800 in the rotational orientation as intended, then the known relationship between parts of the delivery system 800 and parts of the transcatheter heart valve prosthesis, such as the relationship between the location of the flush port 816 and the commissures of the leaflets of the valve structure, is not maintained. Accordingly, embodiments of transcatheter heart valve prostheses hereof include features to ensure proper rotational alignment of the transcatheter heart valve prosthesis and the delivery system 800, and in particular, with the retainer or spindle 810 thereof. FIGS. 34-37 show embodiments of heart valve prostheses with paddle configurations to ensure proper placement within retainers/spindles of a delivery system. The embodiments of FIGS. 34-37 will be described using the reference numerals for the transcatheter heart valve prosthesis 100 described above. However, this is not meant to be limiting, and the features described with respect to FIGS. 34-37 may be applied to any of the transcatheter heart valve prostheses described herein.

Figure 34:
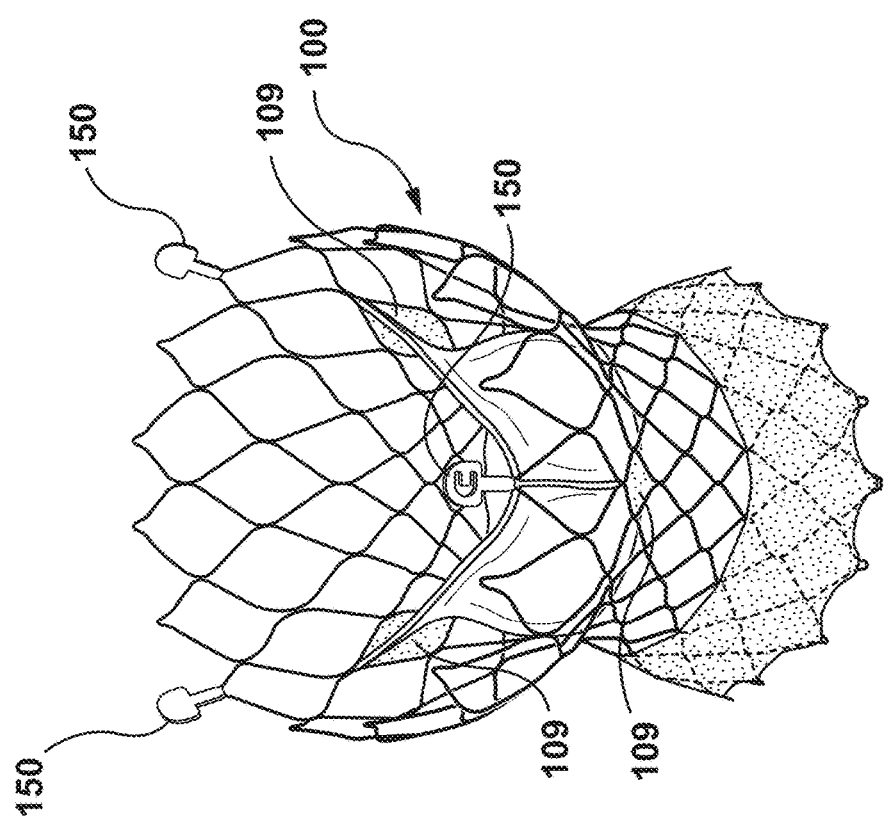

FIG. 34 shows an embodiment wherein the transcatheter heart valve prosthesis 100 includes exactly three paddles 150 instead of two paddles 150, with each paddle 150 axially aligned with one of the commissures 109 of the valve structure 104. The paddles 150 are distributed evenly around a circumference of the transcatheter heart valve prosthesis 100. The retainer 810 of the delivery system is modified to include exactly three paddle pockets 818 to receive the three paddles 150. Thus, because the paddles 150 are distributed evenly around the circumference of the transcatheter heart valve prosthesis 100 and each paddle 150 is aligned with a feature of interest (a commissure), any of the three paddles 150 can be retained within any of the three paddle pockets 818. Thus, rotational orientation of the transcatheter heart valve prosthesis 100 with respect to the delivery system 800 not dependent on properly loading the transcatheter heart valve prosthesis 100. In other words, any rotational orientation of the transcatheter heart valve prosthesis 100 including exactly three paddles 150, with each axially aligned with one of three commissures, disposed in corresponding three paddle pockets 818 will be properly rotationally aligned with the delivery system 800, provided that the spindle 810 is properly oriented, which can be controlled at manufacture.

Figure 35:
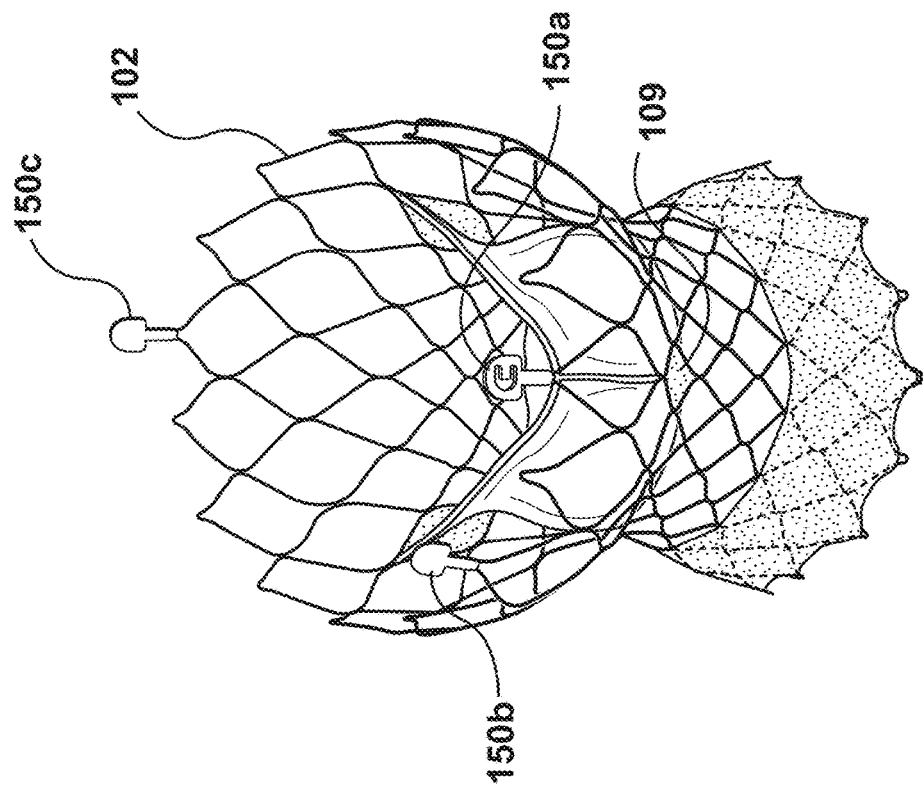
FIGS. 34-37 depict illustrations paddles of a transcatheter heart valve prosthesis in accordance with embodiments hereof.

FIG. 35 shows another embodiment wherein the transcatheter heart valve prosthesis 100 includes three paddles 150a-150c that are unevenly distributed around the circumference of the transcatheter heart valve prosthesis 100. The retainer 810 of the delivery system 800 would include three paddle pockets 818 to receive the three paddles 150a-150c matching the pattern of the paddles 150. In the embodiment of FIG. 35, the paddles 150a and 150b are close to each other, with the paddle 150c spaced at a greater distance around to circumference of the frame 102 than the two paddles 150a, 150b are to each other. In the example shown, the paddle 150a is axially aligned with one of the commissures 109 of the valve structure 104. The paddle 150b is spaced two cells or about 48° from the paddle 150a around the circumference of the frame 102. The paddle 150c is spaced about 180° from the paddle 150a around the circumference of the frame 102 and 6 cells or about 144° from the paddle 150b around the circumference of the frame 102. With this asymmetrical pattern of the paddles 150a-150c and the corresponding asymmetrical pattern of paddle pockets 818 in the retainer or spindle 810 of the delivery system, the transcatheter heart valve prosthesis 100 cannot be coupled to the spindle 810 in an incorrect rotational orientation.

Figures 36, 37:
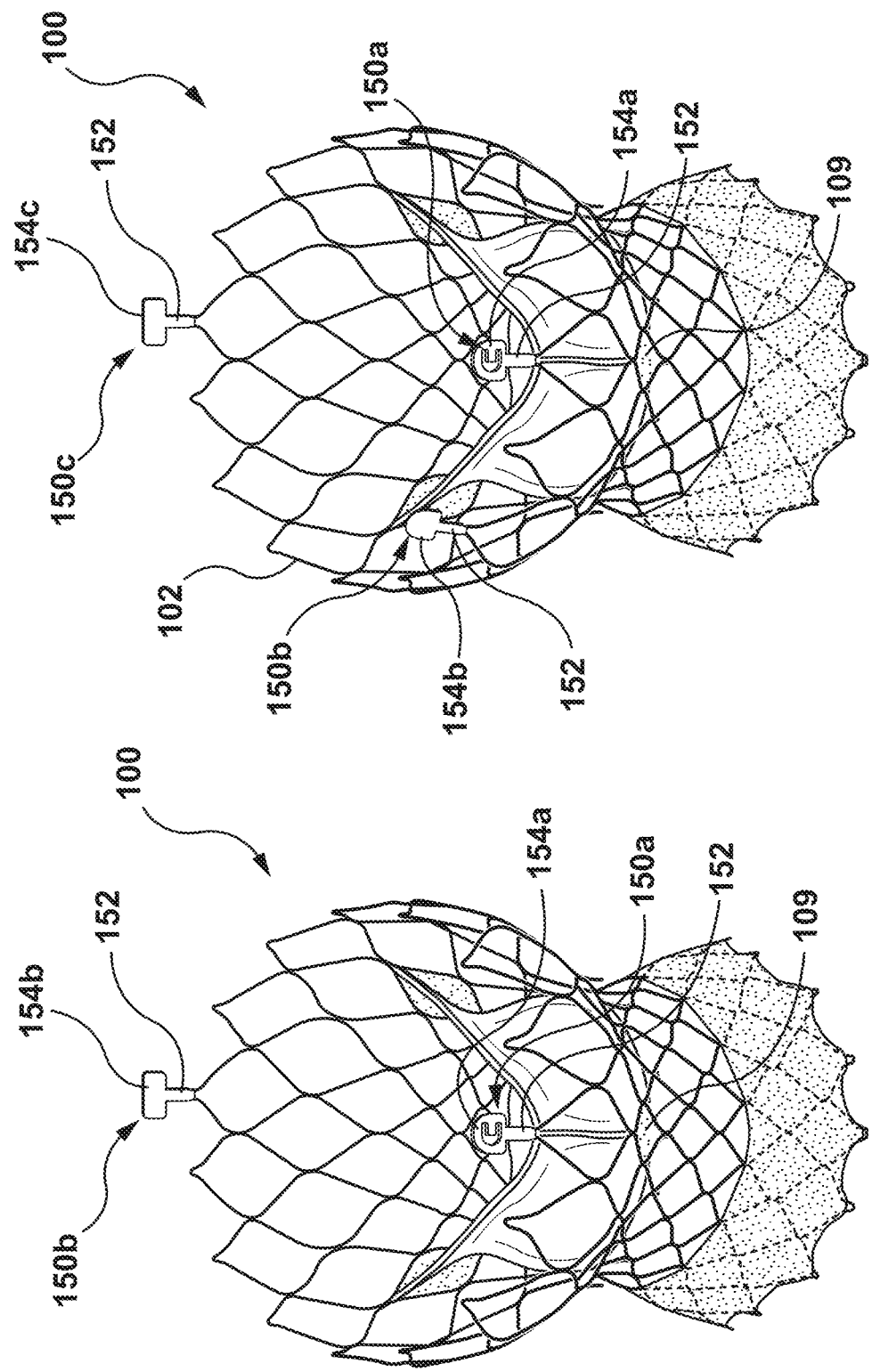

FIG. 36 shows another embodiment wherein the transcatheter heart valve prosthesis 100 includes two paddles 150a and 150b spaced 180° apart from each other around the circumference of the frame 102. The paddle 150a is axially aligned with one of the commissures of the valve structure 104, as described above. In the embodiment of FIG. 36, to ensure proper rotational alignment of the transcatheter heart valve prosthesis with the delivery system 800, the paddles 150a and 150b have different shapes. Further, the two paddle pockets 818 of the spindle 810 are modified such that each has a shape to match only one of the paddles 150a and 150b. In the example of FIG. 46, each paddle 150a, 150b includes a stem 152 and a top 154a and 154b. In the example of FIG. 46, the top 154a of the paddle 150a is generally rounded or circular, whereas the top 154b of the paddle 154b is generally rectangular. With two paddle pockets 818 in the spindle 810, one matching each of the tops 154a and 154b the transcatheter heart valve prosthesis 100 must be loaded in the properly rotational orientation for the proper paddle to fit in the corresponding paddle pocket. It is understood that the shapes shown and described with respect to FIG. 36 are examples only, and any shapes may be used provided that they are different shapes and that the shapes can only fit into the correspondingly shaped paddle pocket of the spindle.

FIG. 37 shows another embodiment that combines the concepts of FIGS. 35 and 36. Thus, in the embodiment of FIG. 37, the transcatheter heart valve prosthesis 100 includes three paddles 150a-150c that are unevenly distributed around the circumference of the transcatheter heart valve prosthesis 100. The retainer 810 of the delivery system 800 includes three paddle pockets 818 to receive the three paddles 150a-150c matching the pattern of the paddles 150. In the embodiment of FIG. 37, as in FIG. 35, the paddles 150a and 150b are close to each other, with the paddle 150c spaced at a greater distance around to circumference of the frame 102 than the two paddles 150a, 150b are to each other. In the example shown, the paddle 150a is axially aligned with one of the commissures 109 of the valve structure 104. The paddle 150b is spaced two cells or about 48° from the paddle 150a around the circumference of the frame 102. The paddle 150c is spaced about 180° from the paddle 150a around the circumference of the frame 102 and 6 cells or about 144° from the paddle 150b around the circumference of the frame 102. Each of the paddles 150a-150c includes a stem 152 and a top 154a-15c. The paddles 150a and 150b include tops 154a, 154b that are generally rounded or circular, whereas the paddle 150c includes a top 154c that is generally rectangular. Therefore, between the asymmetrical pattern of the paddles 150a-150c around the circumference of the frame 102 with the matching asymmetrical pattern of the paddle pockets 818, and the different shape of at least one of the paddles with the matching shapes of the paddle pockets 818, the transcatheter heart valve prosthesis 100 must be loaded in the properly rotational orientation for the paddles to fit in the paddle pockets.

FIGS. 34-37 provide four examples of structures of the paddles and paddle pockets to ensure proper rotational orientation of the paddles with respect to the delivery system. These are not meant to be limiting, and any number of patterns and/or shapes of paddles and paddle pockets may be utilized to ensure proper rotational orientation of the paddles with respect to the delivery system.

As noted above, the systems and methods described above are not limited to transcatheter heart valve prostheses with three (3) markers disposed adjacent the inflow end of the prosthesis. In particular, for rotational alignment, the markers can be disposed anywhere along the length of the transcatheter heart valve prosthesis. However, as explained above, an advantage of locating the markers adjacent the inflow end of the transcatheter heart valve prosthesis is that the markers can also be used for longitudinal or depth alignment such that the inflow portion of the transcatheter heart valve prosthesis can be aligned with the native valve annulus. Another advantage of locating the markers used for rotational orientation adjacent the inflow end of the transcatheter heart valve prosthesis for a self-expanding stent wherein the inflow end of the transcatheter heart valve prosthesis is exposed first is that less of the transcatheter heart valve prosthesis has to be exposed to determine rotational orientation.

Further, as explained above, it is not necessary for the markers 101 to be substantially aligned with the commissures 109 of the transcatheter heart valve prosthesis 100. In other embodiments, the markers may be offset from the commissures. Provided that the relationship between the markers and the commissures is known, the cusp overlap view and/or the coronary overlap view may be used to determine the desired rotational orientation of the transcatheter heart valve prosthesis. In a particular example, markers may be located at the nadirs of the leaflets of the valve structure of the transcatheter heart valve prosthesis. In such an example, in the coronary overlap view, two of the markers located in the overlap area would indicate that the nadirs of the prosthetic heart valve structure 104 are aligned with the coronary ostia, as desired. Also in such an example, using a single marker at one of the nadirs may indicate that the ostia are not blocked because the coronary artery ostia are aligned in the coronary overlap view. Thus, one nadir marker within the overlap area would indicate that both coronary artery ostia are unblocked. Also in the example of markers located at the nadirs, the markers have the additional benefit of guiding a clinician to open areas of the frame post-implantation for access to the coronary arteries.

Figure 10I:
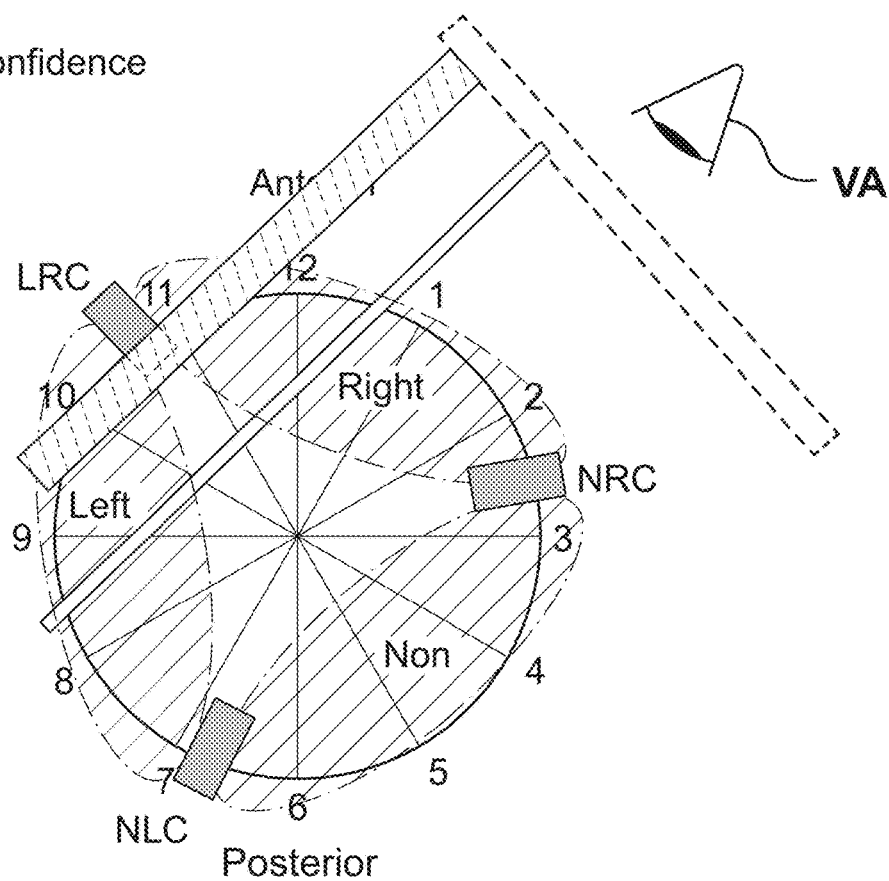
FIG. 10I depicts an illustration of the native aortic valve as viewed from the aorta showing acceptable placement of a single marker of a transcatheter heart valve prosthesis.
Figure 10J:
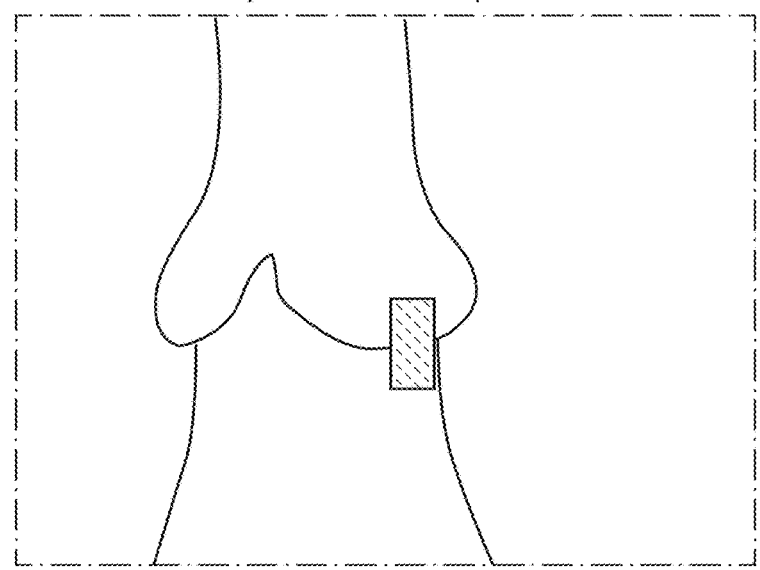
FIG. 10J illustrates a schematic representation of a fluoroscopic image of a native aortic valve using the cusp overlap view and including a transcatheter heart valve prosthesis disposed therein in a partially expanded configuration.

Further, as generally explained above, although three markers 101 are shown and described, the systems and methods described above may be used with more or fewer markers. In particular, in an exemplary embodiment, two (2) markers 101 may be used that are substantially aligned with the commissures 109, and oriented within the delivery system such that the desired rotational alignment of the transcatheter heart valve prosthesis would result in the markers 101 being substantially aligned and towards the left side of the native valve annulus in the cusp overlap view, such as shown in FIGS. 10A-10D but without the marker to the right. In another embodiment, a single marker 101 can be used. The transcatheter heart valve prosthesis is in the desired rotational orientation when the marker 101 is to the right side of the native annulus, as seen in the fluoroscopy image in the cusp overlap view, and within a zone of confidence, as shown in FIGS. 10I and 10J.

Further, in other embodiments, a delivery system such as delivery system 800, or other delivery systems for delivering a transcatheter heart valve prosthesis, such as the transcatheter heart valve prostheses 100, 200, 300, 400, 500, or other transcatheter heart valve prostheses including at least one imaging marker, may further include instructions for use for depth and/or rotational alignment of the transcatheter heart valve prosthesis within the native valve.

For example, and not by way of limitation, in embodiments, the instructions for use may include instructions for rotationally aligning a transcatheter heart valve prosthesis with at least one imaging marker within a native heart valve, the instructions including receiving a cusp overlap viewing angle image and/or a coronary overlap viewing angle image of the transcatheter heart valve prosthesis within the native heart valve, determining, based on the cusp overlap viewing angle image and/or the coronary overlap viewing angle image and the at least one imaging marker, whether the transcatheter heart valve prosthesis is in a desired rotational orientation, and if the at least one imaging marker in the cusp overlap viewing angle image and/or the coronary overlap viewing angle indicates that the transcatheter heart valve prosthesis is not in the desired rotational orientation, rotating the transcatheter heart valve prosthesis until the transcatheter heart valve prosthesis is in the desired rotational orientation.

In some embodiments, there may be three imaging markers substantially axially aligned with a commissure of the valve structure of the transcatheter heart valve prosthesis, and the instructions for use may include instructions to determine, based on the cusp overlap viewing angle image and the three imaging markers, whether two of the imaging markers are substantially aligned on a left side of the cusp overlap viewing angle image.

In some embodiments, the instructions for use may further include instructions to determine an anterior marker and a posterior marker of the two markers on the left side of the cusp overlap viewing angle image. In some embodiments, the instructions for use may further include instructions to determine the anterior marker and the posterior marker by moving a viewing angle of an imaging system from the cusp overlap view to a left anterior oblique viewing angle and determining direction of movement of the two markers. In other embodiments, the instructions for use may further include instructions to determine the anterior marker and the posterior marker by the anterior marker and the posterior marker comprises moving a viewing angle of an imaging system from the cusp overlap view to a right anterior oblique viewing angle and determining direction of movement of the two markers. In other embodiments, the instructions for use may include instructions to determine the anterior marker and the posterior marker by moving a viewing angle of an imaging system from the cusp overlap view to a caudal viewing angle and determining direction of movement of the two markers.

In some embodiments, the transcatheter heart valve prosthesis includes two imaging markers substantially axially aligned with the commissures of the valve structure of the transcatheter heart valve prosthesis, and the instructions for use may include instructions to determine whether the transcatheter heart valve prosthesis in in the desired rotational orientation by determining, based on the cusp overlap viewing angle image and the two imaging markers, whether two of the imaging markers are substantially aligned on a left side of the cusp overlap viewing angle image.

In some embodiments, the transcatheter heart valve prosthesis includes a single imaging marker substantially axially aligned with a commissure of the valve structure of the transcatheter heart valve prosthesis, and the instructions for use may include instructions to determine whether the transcatheter heart valve prosthesis is in the desired rotational orientation by determining, based on the cusp overlap viewing angle image and the single imaging marker, whether the single imaging marker is on a right side of the cusp overlap viewing angle image and within a zone of confidence.

In some embodiments, there may be three markers with each imaging marker substantially axially aligned with a commissure of a valve structure of the transcatheter heart valve prosthesis, and the instructions for use may include instructions to determine whether the transcatheter heart valve prosthesis is in the desired rotational orientation by determining, based on the coronary overlap viewing angle image and the three imaging markers, whether any of the imaging markers are substantially aligned within an overlap area of the coronary artery ostia of the coronary overlap viewing angle image.

In some embodiments, there may be a single imaging marker substantially axially aligned with a commissure of a valve structure of the transcatheter heart valve prosthesis, and the instructions for use may include instructions to determine whether the transcatheter heart valve prosthesis is in the desired rotational orientation by determining, based on the coronary overlap viewing angle image and the single imaging marker, whether the single imaging marker is on a right side of the coronary overlap viewing angle image and outside of an overlap area of the coronary artery ostia of the coronary overlap viewing angle image.

In some embodiments, there may be three imaging markers substantially axially aligned with a respective nadir of a valve structure of the transcatheter valve prosthesis, wherein the instructions for use further include instructions to determine whether the transcatheter heart valve prosthesis is in the desired rotational orientation by determining, based on the coronary overlap viewing angle image and the three imaging markers, whether two of the imaging markers are substantially aligned. The instructions for use may further include instruction to determine whether the transcatheter heart valve prosthesis is in the desired rotational orientation by further determining if the two imaging markers that are substantially aligned are disposed adjacent a common coronary axis in the coronary overlap viewing angle image.

In some embodiments, there may be two imaging markers substantially axially aligned with a respective nadir of a valve structure of the transcatheter valve prosthesis, wherein the instructions for use further include instructions to determine whether the transcatheter heart valve prosthesis is in the desired rotational orientation by determining, based on the coronary overlap viewing angle image and the two imaging markers, whether the two imaging markers are substantially aligned adjacent a common coronary axis in the coronary overlap viewing angle image.

In some embodiments, there may be three imaging markers substantially axially aligned with a respective nadir of a valve structure of the transcatheter valve prosthesis, wherein the instructions for use further include instructions to determine whether the transcatheter heart valve prosthesis is in the desired rotational orientation by determining, based on the coronary overlap viewing angle image and the three imaging markers, whether two of the imaging markers are on a right side of the coronary overlap viewing angle and at least one of the imaging markers is within an overlap area of the coronary artery ostia of the coronary overlap viewing angle image.

In some embodiments, there may be a imaging marker substantially axially aligned with a nadir of a valve structure of the transcatheter valve prosthesis, wherein the instructions for use further include instructions to determine whether the transcatheter heart valve prosthesis is in the desired rotational orientation by determining, based on the coronary overlap viewing angle image and the single imaging marker, whether the single imaging marker is within an overlap area of the coronary artery ostia of the coronary overlap viewing angle image.

Other instructions for use in keeping with the transcatheter heart valve prostheses, delivery systems, and the methods described above may also be provided. Therefore, instructions for use are hereby incorporated for any of the transcatheter heart valve prostheses, delivery systems, and the methods described above, and combinations thereof.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a medical device.

What is claimed is:

1. A method for rotationally aligning a transcatheter heart valve prosthesis within a native heart valve, the method comprising:
   percutaneously delivering the transcatheter heart valve prosthesis to the native heart valve, wherein the transcatheter heart valve prosthesis includes at least one imaging marker;
   receiving a coronary overlap viewing angle image of the transcatheter heart valve prosthesis within the native heart valve;
   determining, based on the coronary overlap viewing angle image and the at least one imaging marker, whether the transcatheter heart valve prosthesis is in a desired rotational orientation; and
   if the at least one imaging marker in the coronary overlap viewing angle indicates that the transcatheter heart valve prosthesis is not in the desired rotational orientation, rotating the transcatheter heart valve prosthesis until the transcatheter heart valve prosthesis is in the desired rotational orientation.

2. The method of claim 1, wherein the at least one imaging marker is substantially axially aligned with a commissure of a valve structure of the transcatheter heart valve prosthesis.

3. The method of claim 1,
   wherein the at least one imaging marker comprises three markers with each imaging marker substantially axially aligned with a commissure of a valve structure of the transcatheter valve prosthesis, and
   wherein determining whether the transcatheter heart valve prosthesis is in the desired rotational orientation comprises determining, based on the coronary overlap viewing angle image and the three imaging markers, whether any two of the imaging markers are substantially aligned within an overlap area of the coronary artery ostia of the coronary overlap viewing angle image.

4. The method of claim 1,
   wherein the at least one imaging marker comprises a single imaging marker substantially axially aligned with a commissure of a valve structure of the transcatheter valve prosthesis, and
   wherein determining whether the transcatheter heart valve prosthesis is in the desired rotational orientation comprises determining, based on the coronary overlap viewing angle image and the single imaging marker, whether the single imaging marker is on a right side of the coronary overlap viewing angle image and outside of an overlap area of the coronary artery ostia of the coronary overlap viewing angle image.

5. The method of claim 1,
   wherein the at least one imaging marker comprises three imaging markers, each of the three imaging markers substantially axially aligned with a nadir of a valve structure of the transcatheter valve prosthesis, and
   wherein determining whether the transcatheter heart valve prosthesis is in the desired rotational orientation comprises determining, based on the coronary overlap viewing angle image and the three imaging markers, whether two of the imaging markers are substantially aligned.

6. The method of claim 5, wherein determining whether the transcatheter heart valve prosthesis is in the desired rotational orientation further comprises determining if the two imaging markers that are substantially aligned are disposed adjacent a common coronary axis in the coronary overlap viewing angle image.

7. The method of claim 1,
   wherein the at least one imaging marker comprises two imaging markers, each of the two imaging markers substantially axially aligned with a nadir of a valve structure of the transcatheter valve prosthesis, and
   wherein determining whether the transcatheter heart valve prosthesis is in the desired rotational orientation comprises determining, based on the coronary overlap viewing angle image and the two imaging markers, whether the two imaging markers are substantially aligned adjacent a common coronary axis in the coronary overlap viewing angle image.

8. The method of claim 1,
wherein the at least one imaging marker comprises three imaging markers, each of the three imaging markers substantially aligned with a nadir of a valve structure of the transcatheter valve prosthesis, and
wherein determining whether the transcatheter heart valve prosthesis is in the desired rotational orientation comprises determining, based on the coronary overlap viewing angle image and the three imaging markers, whether two of the imaging markers are on a right side of the coronary overlap viewing angle and at least one of the imaging markers is within an overlap area of the coronary artery ostia of the coronary overlap viewing angle image.

9. The method of claim 1,
wherein the at least one imaging marker comprises a single imaging marker substantially aligned with a nadir of a valve structure of the transcatheter valve prosthesis, and
wherein determining whether the transcatheter heart valve prosthesis is in the desired rotational orientation comprises determining, based on the coronary overlap viewing angle image and the single imaging marker, whether the single imaging marker is within an overlap area of the coronary artery ostia of the coronary overlap viewing angle image.

10. A method for rotationally aligning a transcatheter heart valve prosthesis within a native heart valve, the method comprising:
percutaneously delivering the transcatheter heart valve prosthesis to the native heart valve, wherein the transcatheter heart valve prosthesis comprises three imaging markers with each imaging marker substantially axially aligned with a commissure of a valve structure of the transcatheter valve prosthesis;
receiving a cusp overlap viewing angle image of the transcatheter heart valve prosthesis within the native heart valve;
determining whether the transcatheter heart valve prosthesis is in a desired rotational orientation by determining, based on the cusp overlap viewing angle image and the three imaging markers, whether two of the imaging markers are substantially aligned on a left side of the cusp overlap viewing angle image; and
if the two imaging markers in the cusp overlap viewing angle image are not substantially aligned on the left side of the cusp overlap viewing angle, rotating the transcatheter heart valve prosthesis until the transcatheter heart valve prosthesis is in the desired rotational orientation.

11. The method of claim 10, further comprising determining an anterior marker and a posterior marker of the two markers on the left side of the cusp overlap viewing angle image.

12. The method of claim 11, wherein determining the anterior marker and the posterior marker comprises moving a viewing angle of an imaging system from the cusp overlap view to a left anterior oblique viewing angle and determining direction of movement of the two markers.

13. The method of claim 11, wherein determining the anterior marker and the posterior marker comprises moving a viewing angle of an imaging system from the cusp overlap view to a right anterior oblique viewing angle and determining direction of movement of the two markers.

14. The method of claim 11, wherein determining the anterior marker and the posterior marker comprises moving a viewing angle of an imaging system from the cusp overlap view to a caudal viewing angle and determining direction of movement of the two markers.

15. A method for rotationally aligning a transcatheter heart valve prosthesis within a native heart valve, the method comprising:
percutaneously delivering the transcatheter heart valve prosthesis to the native heart valve, wherein the transcatheter heart valve prosthesis comprises two imaging markers with each imaging marker substantially axially aligned with a commissure of a valve structure of the transcatheter valve prosthesis;
receiving a cusp overlap viewing angle image of the transcatheter heart valve prosthesis within the native heart valve;
determining whether the transcatheter heart valve prosthesis is in a desired rotational orientation by determining, based on the cusp overlap viewing angle image and the two imaging markers, whether the two imaging markers are substantially aligned on a left side of the cusp overlap viewing angle image; and
if the two imaging markers in the cusp overlap viewing angle image are not substantially aligned on the left side of the cusp overlap viewing angle, rotating the transcatheter heart valve prosthesis until the transcatheter heart valve prosthesis is in the desired rotational orientation.

16. The method of claim 15, further comprising determining an anterior marker and a posterior marker of the two imaging markers on the left side of the cusp overlap viewing angle image.

17. A method for rotationally aligning a transcatheter heart valve prosthesis within a native heart valve, the method comprising:
percutaneously delivering the transcatheter heart valve prosthesis to the native heart valve, wherein the transcatheter heart valve prosthesis comprises a single imaging marker substantially axially aligned with a commissure of a valve structure of the transcatheter valve prosthesis;
receiving a cusp overlap viewing angle image of the transcatheter heart valve prosthesis within the native heart valve;
determining whether the transcatheter heart valve prosthesis is in a desired rotational orientation by determining, based on the cusp overlap viewing angle image and the single imaging marker, whether the single imaging marker is on a right side of the cusp overlap viewing angle image and within a zone of confidence; and
if the single imaging marker in the cusp overlap viewing angle image is not on the right side of the cusp overlap viewing angle and within the zone of confidence, rotating the transcatheter heart valve prosthesis until the transcatheter heart valve prosthesis is in the desired rotational orientation.

* * * * *